US008445558B2

(12) United States Patent
Karim et al.

(10) Patent No.: US 8,445,558 B2
(45) Date of Patent: May 21, 2013

(54) DENTAL COMPOSITIONS INCLUDING ORGANOGELATORS, PRODUCTS, AND METHODS

(75) Inventors: Naimul Karim, Maplewood, MN (US); Todd D. Jones, St. Paul, MN (US); Kevin M. Lewandowski, Inver Grove Heights, MN (US); Bradley D. Craig, Cottage Grove, MN (US); Sumita B. Mitra, West St. Paul, MN (US); Jie Yang, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 455 days.

(21) Appl. No.: 12/441,011

(22) PCT Filed: Sep. 12, 2007

(86) PCT No.: PCT/US2007/078257
§ 371 (c)(1),
(2), (4) Date: Aug. 5, 2009

(87) PCT Pub. No.: WO2008/033911
PCT Pub. Date: Mar. 20, 2008

(65) Prior Publication Data
US 2009/0305196 A1 Dec. 10, 2009

Related U.S. Application Data

(60) Provisional application No. 60/825,491, filed on Sep. 13, 2006.

(51) Int. Cl.
*A61K 6/083* (2006.01)
*A61C 5/09* (2006.01)
*A61C 5/08* (2006.01)
*A61K 6/06* (2006.01)

(52) U.S. Cl.
CPC .................. *A61C 5/08* (2013.01); *A61K 6/0662* (2013.01); *A61K 6/083* (2013.01); *Y10S 977/919* (2013.01)
USPC ........... 523/116; 523/118; 524/186; 524/493; 433/218; 433/228.1; 977/919

(58) Field of Classification Search
USPC .......... 523/116, 118; 524/186, 493; 433/218, 433/228.1; 977/919
See application file for complete search history.

(56) References Cited

U.S. PATENT DOCUMENTS

| 2,776,951 | A | 1/1957 | Melamed |
| 3,541,068 | A | 11/1970 | Taylor |
| 4,298,738 | A | 11/1981 | Lechtken et al. |
| 4,324,744 | A | 4/1982 | Lechtken et al. |
| 4,356,296 | A | 10/1982 | Griffith et al. |
| 4,385,109 | A | 5/1983 | Lechtken et al. |
| 4,503,169 | A | 3/1985 | Randklev |
| 4,507,466 | A | 3/1985 | Tomalia et al. |
| 4,558,120 | A | 12/1985 | Tomalia et al. |
| 4,568,737 | A | 2/1986 | Tomalia et al. |
| 4,587,329 | A | 5/1986 | Tomalia et al. |
| 4,631,337 | A | 12/1986 | Tomalia et al. |
| 4,642,126 | A | 2/1987 | Zador et al. |
| 4,648,843 | A | 3/1987 | Mitra |
| 4,652,274 | A | 3/1987 | Boettcher et al. |
| 4,694,064 | A | 9/1987 | Tomalia et al. |
| 4,695,251 | A | 9/1987 | Randklev |
| 4,710,523 | A | 12/1987 | Lechtken et al. |
| 4,713,975 | A | 12/1987 | Tomalia et al. |
| 4,737,550 | A | 4/1988 | Tomalia |
| 4,737,593 | A | 4/1988 | Ellrich et al. |
| 4,857,599 | A | 8/1989 | Tomalia et al. |
| 4,871,779 | A | 10/1989 | Killat et al. |
| 4,872,936 | A | 10/1989 | Engelbrecht |
| 4,978,007 | A | 12/1990 | Jacobs et al. |
| 5,015,180 | A | 5/1991 | Randklev |
| 5,063,255 | A | 11/1991 | Hasegawa et al. |
| 5,063,257 | A | 11/1991 | Akahane et al. |
| 5,076,844 | A | 12/1991 | Fock et al. |
| 5,130,347 | A | 7/1992 | Mitra |
| 5,154,762 | A | 10/1992 | Mitra et al. |
| 5,227,413 | A | 7/1993 | Mitra |
| 5,328,363 | A | 7/1994 | Chester et al. |
| 5,367,002 | A | 11/1994 | Huang et al. |
| 5,418,301 | A | 5/1995 | Hult et al. |
| 5,501,727 | A | 3/1996 | Wang et al. |
| 5,520,725 | A | 5/1996 | Kato et al. |
| 5,545,676 | A | 8/1996 | Palazzotto et al. |
| 5,731,474 | A | 3/1998 | Scrivens et al. |
| 5,814,407 | A | 9/1998 | Richard |

(Continued)

FOREIGN PATENT DOCUMENTS

| EP | 0115410 | 8/1984 |
| EP | 0 173 567 | 3/1986 |

(Continued)

OTHER PUBLICATIONS

Rice et al.; "N,N-Dialkyloxamides" Journal of the American Chemical Society, vol. 75, No. 1, Jan. 1953, pp. 242-243 (XP007914534).
ANSI/ ADA Specification No. 27 (1993).
Antonucci et al., "1642 Effect of an Organogelator on a HEMA-Based Adhesive System," Abstract 2006 AADR and ADEA Annual Meeting, (full cite?).
Bertini et al., "Monomers Containing Substrate or Inhibitor Residues for Copper Amine Oxidases and their Hydrophilic Beaded Resins Designed for Enzyme Interatction Studies", *Tetrahedron*, 2004; 60:11407.
de Loos et al., "Remarkable Stabilization of a Self-Assembled Organogels by Polymerization," *J. Am. Chem. Soc.*, 1997; 119: 12675-12676.
George et al., "Urea and Thiourea Derivatives as Low Molecular-Mass Organogelators", *Chem. Eur. J.*, 2005; 11:3243.
Gronwald et al., "Sugar-Integrated Gelators of Organic Solvents", *Chem. Eur. J.*, 2001; 7:4329-4334.
Makarevic et al., "Bis(Amino Acid) Oxalyl Amides as Ambidextrous Gelators of Water and Organic Solvents: Supramolecular Gels with Temperature Dependent Assembly/Dissolution Equilibrium", *Chem. Eur. J.*, 2001; 7:3328-3341.

(Continued)

*Primary Examiner* — Tae H Yoon
(74) *Attorney, Agent, or Firm* — Carolyn A. Fischer

(57) ABSTRACT

A hardenable dental composition that includes a polymerizable component and an organogelator.

28 Claims, No Drawings

U.S. PATENT DOCUMENTS

| | | | |
|---|---|---|---|
| 5,830,986 | A | 11/1998 | Merrill et al. |
| 5,856,373 | A | 1/1999 | Kaisaki et al. |
| 5,859,089 | A | 1/1999 | Qian |
| 5,859,148 | A | 1/1999 | Borggreve et al. |
| 5,871,360 | A | 2/1999 | Kato |
| 5,919,870 | A | 7/1999 | Letchford et al. |
| 5,925,715 | A | 7/1999 | Mitra |
| 5,962,550 | A | 10/1999 | Akahane et al. |
| 5,965,632 | A | 10/1999 | Orlowski et al. |
| 6,030,606 | A | 2/2000 | Holmes |
| 6,084,004 | A | 7/2000 | Weinmann et al. |
| 6,187,833 | B1 | 2/2001 | Oxman et al. |
| 6,187,836 | B1 | 2/2001 | Oxman et al. |
| 6,251,963 | B1 | 6/2001 | Köhler et al. |
| 6,252,014 | B1 | 6/2001 | Knauss |
| 6,306,926 | B1 | 10/2001 | Bretscher et al. |
| 6,387,981 | B1 | 5/2002 | Zhang et al. |
| 6,506,816 | B1 | 1/2003 | Ario et al. |
| 6,624,211 | B2 | 9/2003 | Karim et al. |
| 6,730,156 | B1 | 5/2004 | Windisch et al. |
| 6,765,036 | B2 | 7/2004 | Dede et al. |
| 6,765,038 | B2 | 7/2004 | Mitra |
| 6,964,985 | B2 | 11/2005 | Karim et al. |
| 6,982,288 | B2 | 1/2006 | Mitra et al. |
| 7,393,882 | B2 | 7/2008 | Wu et al. |
| 2003/0114553 | A1 | 6/2003 | Karim et al. |
| 2003/0119932 | A1* | 6/2003 | Al-Akhdar et al. .............. 522/18 |
| 2003/0166740 | A1 | 9/2003 | Mitra et al. |
| 2003/0207179 | A1 | 11/2003 | Uetani et al. |
| 2004/0065227 | A1 | 4/2004 | Breton et al. |
| 2005/0040551 | A1 | 2/2005 | Biegler et al. |
| 2005/0252413 | A1 | 11/2005 | Kangas et al. |
| 2006/0122308 | A1* | 6/2006 | Wermter et al. .............. 524/445 |
| 2006/0256223 | A1 | 11/2006 | Lee |
| 2008/0242759 | A1 | 10/2008 | Wu et al. |
| 2009/0032989 | A1 | 2/2009 | Karim et al. |
| 2010/0130445 | A1 | 5/2010 | Yang |
| 2010/0150847 | A1 | 6/2010 | Yang |

FOREIGN PATENT DOCUMENTS

| | | |
|---|---|---|
| EP | 0 201 031 | 11/1986 |
| EP | 0 201 778 | 12/1988 |
| EP | 0383023 | 8/1990 |
| EP | 0 461 586 | 12/1991 |
| EP | 0 373 384 | 10/1992 |
| EP | 0650974 | 5/1995 |
| EP | 0709402 | 5/1996 |
| EP | 0 907 680 | 1/2000 |
| EP | 1 591 098 | 11/2005 |
| GB | 2 225 333 | 5/1990 |
| GB | 2306473 | 5/1997 |
| JP | 2003-277723 | 10/2003 |
| WO | WO 99/64563 | 12/1999 |
| WO | WO 00/38619 A2 | 7/2000 |
| WO | WO 00/38619 A3 | 7/2000 |
| WO | WO 00/42092 A1 | 7/2000 |
| WO | WO 01/07444 A1 | 2/2001 |
| WO | WO 01/30304 A1 | 5/2001 |
| WO | WO 01/30305 A1 | 5/2001 |
| WO | WO 01/30306 A1 | 5/2001 |
| WO | WO 01/30307 A1 | 5/2001 |
| WO | WO 01/92271 A1 | 12/2001 |
| WO | WO 03/015720 A1 | 2/2003 |
| WO | WO 2012/036838 | 3/2012 |

OTHER PUBLICATIONS

Mathis et al., "Properties of a New Glass Ionomer/Composite Resin Hybrid Restorative," Abstract No. 51, *J. Dent. Res.*, 66:113 (1987).

Plate et al., "Comb-Like Polymers. Structure and Properties," *Journal of Polymer Science, Macromolecular Reviews*, 1974; 8:117-253.

Rice et al., "N,N-Dialkyloxamides", *J. Chem. Soc.*, 1953; 75:242-243.

Suzuki et al., "New Low-Molecular Weight Gelators Based on L-Valine and IL Isoleucine With Various Terminal Groups", *Tet. Lett.*, 2005; 46:2741.

Terech et al., "Low Molecular Mass Gelators of Organic Liquids and the Properties of Their Gels," *Chem. Rev.*, 1997; 97:3133-3159.

Wang et al., "Synthesis and Self-Assembling Properties of Polymerizable Organogelators", *Chem. Eur. J.*, 2002; 8:1954-1961.

Wilder et al., "Effect of an Organogelator on the Properties of Dental Composites," *Chem. Mater.*, 2005; 17:2946-2952.

Wilder et al., "Improved Dental Composites Utilizing Dibenzylidene Sorbitol Networks," *Macromol. Symp.*, 2005; 227:255-263.

Larpent, et al., "Macrocyclic sugar-based surfactants: block molecules combining self-aggregation and complexation properties", (2004) Abstract, 3 pgs.

Furhop et al., "Two polymeric micellar fibers with gluconamide head groups", (1991) abstract, 2 pgs.

Melamed, Amides of Vinyl Ethers Containing Hydroxyl Groups, and Polymers Thereof, (1957), abstract, 2 pgs.

Hamade et al., "D-gluconamide derivatives for preparing lipid-coated enzymes and antifouling marine paint compositions", (1997), abstract, 5 pgs.

* cited by examiner

DENTAL COMPOSITIONS INCLUDING ORGANOGELATORS, PRODUCTS, AND METHODS

CROSS REFERENCE TO RELATED APPLICATIONS

This application is a national stage filing under 35 U.S.C. 371 of PCT/US2007/078257, filed Sep. 12, 2007, which claims the benefit of U.S. Provisional Application No. 60/825,491, filed Sep. 13, 2006, the disclosures of which is incorporated by reference in their entirety herein.

BACKGROUND

This invention relates to materials, particularly dental materials, including polymerizable resins, including photopolymerizable, and methods of making and using. Currently available polymerizable resins are typically free radically polymerizable monomers (e.g., acrylates, methacrylates, and acrylamides). These are used together with initiator systems that typically include reducing agents, such as tertiary amines, and oxidizing agents, such as peroxides, as accelerators or activators. Additional materials of this type are needed for a variety of applications, particularly dental applications.

SUMMARY

The present invention is directed toward compositions containing organogelators and organic polymerizable components that can be used in a variety of dental applications.

In one embodiment, the present invention provides a dental composition that includes an organic polymerizable component, an organogelator, and a crystalline material.

In another embodiment, the present invention provides a hardenable dental composition that includes an organic polymerizable component, an organogelator, and 60% or more filler material.

In another embodiment, the present invention provides a hardenable dental composition that includes an organic polymerizable component, an organogelator, and filler material comprising nanoscopic particles.

In another embodiment, the present invention provides a hardenable dental composition that includes an organic polymerizable component and a polymerizable organogelator.

In certain embodiments, the hardenable composition can be flowable. A flowable material is of a lower viscosity, such that it can be dispensed from a narrow-tip syringe, typically 20 gauge or similar, under hand pressure. Flowable dental compositions often have lower loadings of filler than other nonflowable dental compositions.

In certain embodiments, the hardenable compositions can be packable. A packable material has handling characteristics similar to a dental amalgam. In particular, it is typically carvable, and is more viscous than standard universal composites. Packable dental compositions often have higher viscosities, and filler loadings, than flowable dental compositions.

In certain embodiments, the hardenable composition can be in the form of a hardenable, self-supporting (i.e., freestanding) structure having a first shape. The self-supporting structure has sufficient malleability to be reformed into a second shape, thereby providing for simplified customization of a device, e.g., simplified customized fitting of a dental prosthetic device. Once reformed into a second shape, the composition can be hardened using, for example, a free radical curing mechanism under standard photopolymerization conditions to form a hardened composition with improved mechanical properties. Significantly, for the compositions of the present invention upon hardening the structure in the second shape, the hardened structure does not need an additional veneering material.

In another embodiment, the present invention provides orthodontic adhesives, i.e., adhesives that can be applied to orthodontic appliances (including, but not limited to, orthodontic brackets, buccal tubes, lingual tubes, and cleats) to bond the appliances to teeth.

In certain embodiments, the hardenable composition includes an organogelator of the general formula (Formula I):

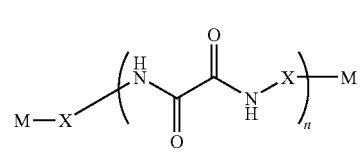

wherein: each M is independently hydrogen or a polymerizable group; each X is independently an alkylene group, cycloalkylene group, arylene group, arenylene group, or a combination thereof, and n is 1 to 3. Such organogelators are also provided by the present invention.

In certain embodiments, the hardenable dental composition includes an amino sugar organogelator.

In certain embodiments, the organogelator is an amino sugar organogelator of the general formula LXXV:

wherein: $R^1$ and $R^2$ are independently selected from the group consisting of a hydrogen atom, an alkyl group, $C(O)R^3$, and $SO_2R^4$; $R^3$ and $R^4$ are independently selected from the group consisting of an alkyl group, an aryl group, and an aralkyl group; and n is an integer from about 2 to about 5. In certain embodiments, the organogelator is selected from the group consisting of compounds of the formulas:

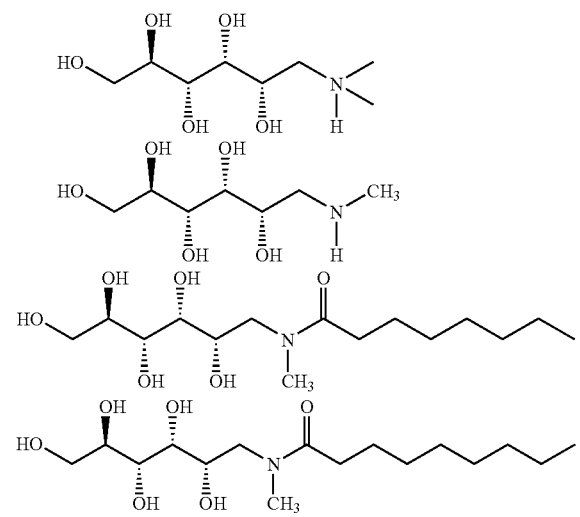

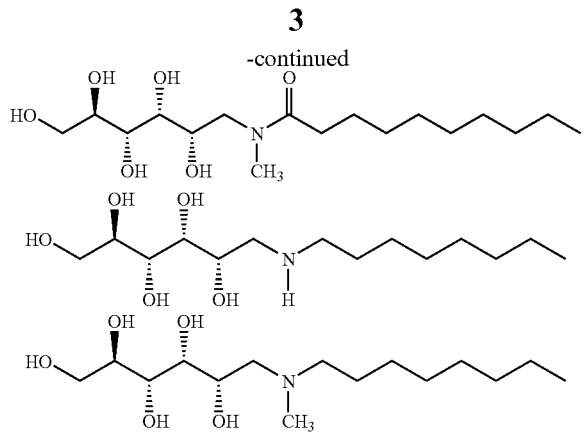

and mixtures thereof.

In certain embodiments, the organogelator is an amino sugar organogelator of the general formula LXXXIII:

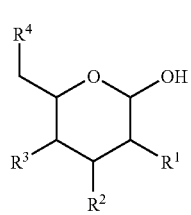

LXXXIII wherein: $R^1$, $R^2$, and $R^3$ are independently selected from the group consisting of OH and $NR^5R^6$; $R^4$ is selected from the group consisting of OH, $OP(O)(OH)_2$, $OSO_3H$, and $NR^5R^6$; $R^5$ and $R^6$ are independently selected from the group consisting of a hydrogen atom, an alkyl group, $C(O)R^7$, and $SO_2R^8$; and $R^7$ and $R^8$ are independently selected from the group consisting of an alkyl group, an aryl group, or an aralkyl group; provided that at least one of $R^1$, $R^2$, $R^3$, and $R^4$ is $NR^5R^6$. In certain embodiments, the organogelator is selected from the group consisting of compounds of the formulas:

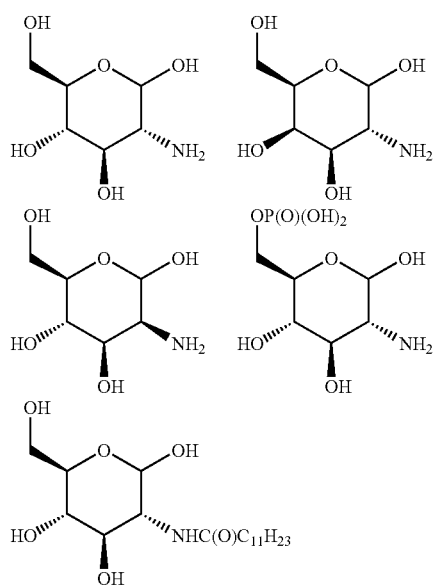

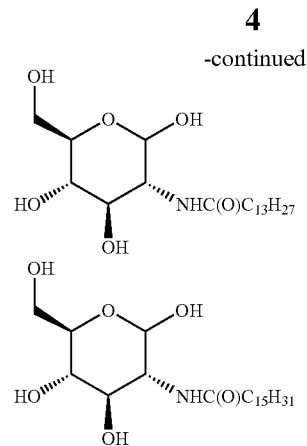

and mixtures thereof.

The present invention also provides dental products and methods of making dental products, particularly crowns. The present invention also provides methods of using the hardenable dental compositions and dental products.

Herein, an "organogelator" is a generally low molecular weight organic compound (generally no greater than 3000 g/mol) that forms a three-dimensional network structure when dissolved in an organic fluid, thereby immobilizing the organic fluid and forming a non-flowable gel that exhibits a thermally reversible transition between the liquid state and the gel state when the temperature is varied above or below the gel point of the mixture.

Herein, the "polymerizable component" can include one or more resins, each of which can include one or more monomers, oligomers, and/or polymerizable polymers.

The term "self-supporting" means that the composition is dimensionally stable and will maintain its shape (e.g., preformed shape of a crown) without significant deformation at room temperature for at least two weeks when free-standing (i.e., without the support of packaging or a container). Preferably, such self-supporting compositions of the present invention are dimensionally stable at room temperature for at least one month, and more preferably, for at least six months. This definition applies in the absence of conditions that activate the initiator system and in the absence of an external force other than gravity.

The term "sufficient malleability" means that the self-supporting structure is capable of being custom shaped and fitted, for example, to a patient's mouth, under a moderate force (i.e., a force that ranges from light finger pressure to that applied with manual operation of a small hand tool, such as a dental composite instrument).

The term "hardenable" refers to a composition that can undergo polymerization and/or crosslinking reactions including, for example, photopolymerization reactions and chemical polymerization techniques (e.g., redox reactions) involving one or more materials included in the composition.

Compositions of the present invention have numerous potential applications. These applications include, but are not limited to, dental restoratives and dental prostheses, including, but not limited to, temporary, intermediate/interim, and permanent crowns and bridges, inlays, onlays, veneers, implants, dentures, and artificial teeth, as well as dental impression trays, orthodontic appliances (e.g., retainers, night guards), orthodontic adhesives, tooth facsimiles or splints, maxillofacial prostheses, and other customized structures. The compositions of the present invention can also be used as filling materials (particularly packable materials and flowable composites), for example.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a composition that comprises "an" organogelator can be interpreted to mean that the composition includes "one or more" organogelators.

The term "and/or" means one or all of the listed elements or a combination of any two or more of the listed elements (e.g., a composition that is flowable, packable, and/or self-supporting means that the composition is flowable, packable, or self-supporting, the composition may be both packable and self-supporting, for example).

Also herein, the recitations of numerical ranges by endpoints include all numbers subsumed within that range (e.g., 1 to 5 includes 1, 1.5, 2, 2.75, 3, 3.80, 4, 5, etc.).

When a group is present more than once in a formula described herein, each group is "independently" selected, whether specifically stated or not. For example, when more than one M group is present in a formula, each M group is independently selected.

As used herein, the term "room temperature" refers to a temperature of 20° C. to 25° C. or 22° C. to 25° C.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention is directed toward hardenable dental compositions containing organogelators and polymerizable components that can be used in a variety of dental applications having a variety of properties. For example, the hardenable compositions of the present invention can be flowable, packable, and/or self-supporting.

Preferred hardenable dental compositions of the present invention are organic based. That is, hardenable organic dental compositions of the present invention include less than 50 wt-% water, preferably less than 45 wt-%, more preferably less than 25 wt-%, even more preferably less than 10 wt-%, even more preferably less than 5 wt-%, and even more preferably less than 1 wt-%, based on the total weight of the composition.

The hardened dental material can be any of a wide variety of materials that are prepared from polymerizable materials. They can be used in a variety of applications, including oral prosthetic devices such as inlays, onlays, veneers, crowns (temporary, intermediate/interim, or permanent), bridges, implants, dentures, artificial teeth, filling materials (particularly packable materials and flowable composites), orthodontic appliances (e.g., retainers, night guards), orthodontic adhesives, tooth facsimiles or splints, dental impression trays, maxillofacial prostheses, as well as other customized structures.

Hardenable dental compositions of the present invention can be flowable, packable, or self-supporting, for example. It will be understood by one of skill in the art that such terms are not necessarily mutually exclusive. That is, there may be some overlap such that a packable composition may be self-supporting to some degree and vice versa, for example. Generally, pre-cure rheological characteristics of packable and self-supporting compositions are very similar (if not identical). Generally, the level of packability, flowability, and ability to be self-supporting can relate to the level and type of filler, although it is the overall combination of components that controls rheology. Generally, flowable materials have a lower level of filler (e.g., 60 percent by weight or less) than packable or self-supporting compositions, and may use higher levels of uniparticulate (i.e., unagglomerated) fillers than packable or self-supporting compositions. Self-supporting compositions may use higher levels of agglomerated fillers. It should be understood, however, that these are not necessary requirements.

In certain embodiments, a hardenable dental composition is in the form of a hardenable self-supporting (i.e., free-standing) structure having a first shape, preferably the shape of a dental crown. For such embodiments, the components are chosen such that: the composition can be relatively easily molded to form the initial self-supporting structure; the self-supporting structure maintains its first shape at room temperature for at least two weeks (in the absence of conditions that activate the initiator system and in the absence of an external force other than gravity); and the self-supporting structure has sufficient malleability to be reformed into a second shape (preferably at a temperature of 15° C. to 38° C., more preferably, at a temperature of 20° C. to 38° C., and most preferably, at room temperature).

Such self-supporting compositions of the present invention are particularly well suited for preformed dental products. As used herein, a preformed dental product is one that is provided to the dentist in the desired semi-finished shape (a first shape), which can then be modified (e.g., molded, adapted, trimmed) for fit in a patient (a second shape). Herein, a semi-finished shape of a preformed article is the facsimile of what the final shaped article is to be, and is not the shape of a rope, globule, or sheet. Typically, this means that self-supporting compositions of the present invention have been formed into a shape, preferably using a mold with a positive and negative impression, and the resultant shaped material released from the shaping device, preferably a mold, without significant deformation.

Although certain compositions of the present invention are particularly useful for preformed crowns and other preformed dental products having a complex shape, the same or other compositions can be used as materials for preparing fillings, etc. The requirements for the latter are less stringent when it comes to molding, removal from a mold, packaging, transportation, and the like, than is required for preformed crowns or other preformed dental articles of a complex shape, typically because filling materials are provided to the dentist in, for example, a rope form, or in discrete pieces, like chunks, tablets, and the like.

Generally, hardenable self-supporting compositions of the present invention have rheological properties similar to waxes below the waxes' melting points in that they can be relatively easily deformed (i.e., they are malleable) and exhibit low elastic recovery. However, hardenable self-supporting compositions of the present invention are not free-flowing fluids (i.e., liquids) above their softening points. That is, hardenable self-supporting compositions of the present invention display appreciable mass flow under moderate (e.g., hand) pressure, but not liquid flow above their softening points.

The desired self-supporting (i.e., free-standing) structure of certain hardenable compositions of the present invention can be maintained by creating a morphology that includes a noncovalent structure, which may be a three-dimensional network (continuous or discontinuous) structure.

Preferably, resultant hardened compositions (i.e., hardened structures) formed from hardenable self-supporting compositions have a flexural strength of at least 25 megapascals (MPa), more preferably, at least 40 MPa, even more preferably, at least 50 MPa, and most preferably, at least 60 MPa.

For certain applications (e.g., crowns or fillings), resultant hardened compositions (i.e., hardened structures) formed from hardenable self-supporting compositions are enamel-like solids, preferably having a compressive strength of at least 100 MPa. For other applications, such as dental impression trays, materials with lower compressive strengths can be used.

For certain applications (e.g., crowns or fillings), resultant hardened compositions (i.e., hardened structures) formed from hardenable self-supporting compositions are enamel-like solids, preferably having a diametral tensile strength of at least 20 MPa. For other applications, such as dental impression trays, materials with lower diametral tensile strengths can be used.

For certain applications (e.g., crowns or fillings), resultant hardened compositions (i.e., hardened structures) formed from hardenable self-supporting compositions are enamel-like solids, preferably having a flexural modulus of at least 1000 MPa. For other applications, such as dental impression trays, materials with lower flexural modulus can be used.

Organogelators

A wide variety of organogelators can be used in the hardenable compositions of the present invention. Organogelators are generally low molecular weight organic compounds (i.e., compounds with organic-containing moieties), including organometallic compounds. By "generally low molecular weight" is meant that the compounds have a molecular weight of generally no greater than 3000, preferably no greater than 2000, and even more preferably no greater than 1000 grams per mole (g/mol). They form a three-dimensional network structure when dissolved in an organic fluid (e.g., one or more fluid polymerizable components), thereby immobilizing the organic fluid and forming a non-flowable gel.

A material is considered an organogelator relative to the system it is in. That is, for example, one material may function as an organogelator in one particular hardenable composition such that a three-dimensional network structure and a resultant a non-flowable gel is formed; however, the same material may not function as an organogelator in another hardenable composition. Based on the teachings herein, one of skill in the art can readily determine whether a material is an organogelator or not without undue experimentation. For example, a prospective organogelator can be subjected to the Gelation Test in a hardenable composition of interest to determine if the material is an organogelator in this system.

A non-flowable gel typically includes a solid-like phase and a liquid phase in coexistance, wherein the solid-like phase forms a three-dimensional network structure throughout the liquid phase and prevents the liquid phase from flowing at a macroscopic level. The mixture of organogelator and polymerizable component (without the filler material and optional additives) exhibit a thermally reversible transition between the liquid state and the gel state when the temperature is varied above or below the gel point of the mixture.

While not intending to be bound by theory, it is believed that the gel formation results when the organogelators self-assemble to fiber-like structures, which then entangle to form a network. The driving force for the molecular aggregation may be physical, noncovalent interactions, such as hydrogen-bonding, aromatic interactions, ionic bonding, coordination bonding, London dispersion interactions, π stacking, solvophobic effects, or other physical interactions.

It should be understood that organogelators do not include thickeners such as fumed silica, although fumed silica can be used as the filler material as described herein.

Organogelators can be polymerizable or not. Preferred organogelators for dental compositions are polymerizable so that they can be incorporated into a resin system during hardening. This may reduce the amount of leaching of the organogelator under use conditions in the mouth.

Exemplary organogelators are described in U.S. Pat. Pub. Nos. 2004/0065227 (Breton et al.) and 2003/0207179 (Uetani et al.), as well as Terech et al., *Chem. Rev.,* 97, 3133-3159 (1997), de Loos et al., *J. Am. Chem. Soc.,* 119, 12675-12676 (1997), Makarevic et al., *Chem. Eur. J.,* 7, 3328-3341 (2001), Wang et al., *Chem. Eur. J.,* 8, 1954-1961 (2002), and Japan Pat. Pub. No. 2003-277723. Various combinations of organogelators can be used if desired.

Suitable such compounds include, for example: sugar-based compounds such as dibenzylidene sorbitol and alpha-manno(methyl 4,6-O-benzylidene-alpha-D-mannopyranoside); substituted fatty acids and monovalent, divalent, or trivalent metal salts of fatty acids such as the lithium salt of 12-hydroxyoctadecanoic acid; and steroid-based compounds such as deoxycholic, apocholic, and lithocholic acids, and their salts, as well as cholesteric esters and derivatives thereof.

Other suitable organogelators include anthryl-based (i.e., anthracene-based) compounds and anthryl- and anthraquinone-appended steroid-based compounds with the general formulas (Formulas II and III):

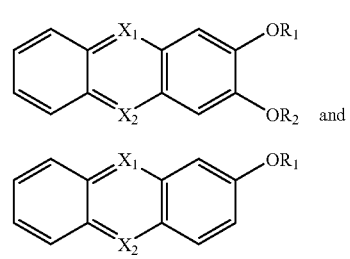

wherein: $X_1$ and $X_2$ each, independently of the other is a nitrogen atom, a —CH-group, or a —C(O)-group; and $R_1$ and $R_2$ each, independently of the other, can be an alkyl group (including linear, branched, saturated, unsaturated, cyclic, unsubstituted, and substituted alkyl groups, and wherein heteroatoms, such as oxygen, nitrogen, sulfur, silicon, phosphorus, and/or functional groups, such as carbonyl groups, may or may not be present in the alkyl group), an aryl group (including substituted or unsubstituted aryl groups, and wherein heteroatoms, such as oxygen, nitrogen, sulfur, silicon, phosphorus, and/or functional groups, such as carbonyl groups, may or may not be present in the aryl group), or a combination thereof. Some specific examples of suitable anthracene compounds, anthraquinone compounds, and phenazine compounds include, but are not limited to (Formulas IV through XIV, respectively):
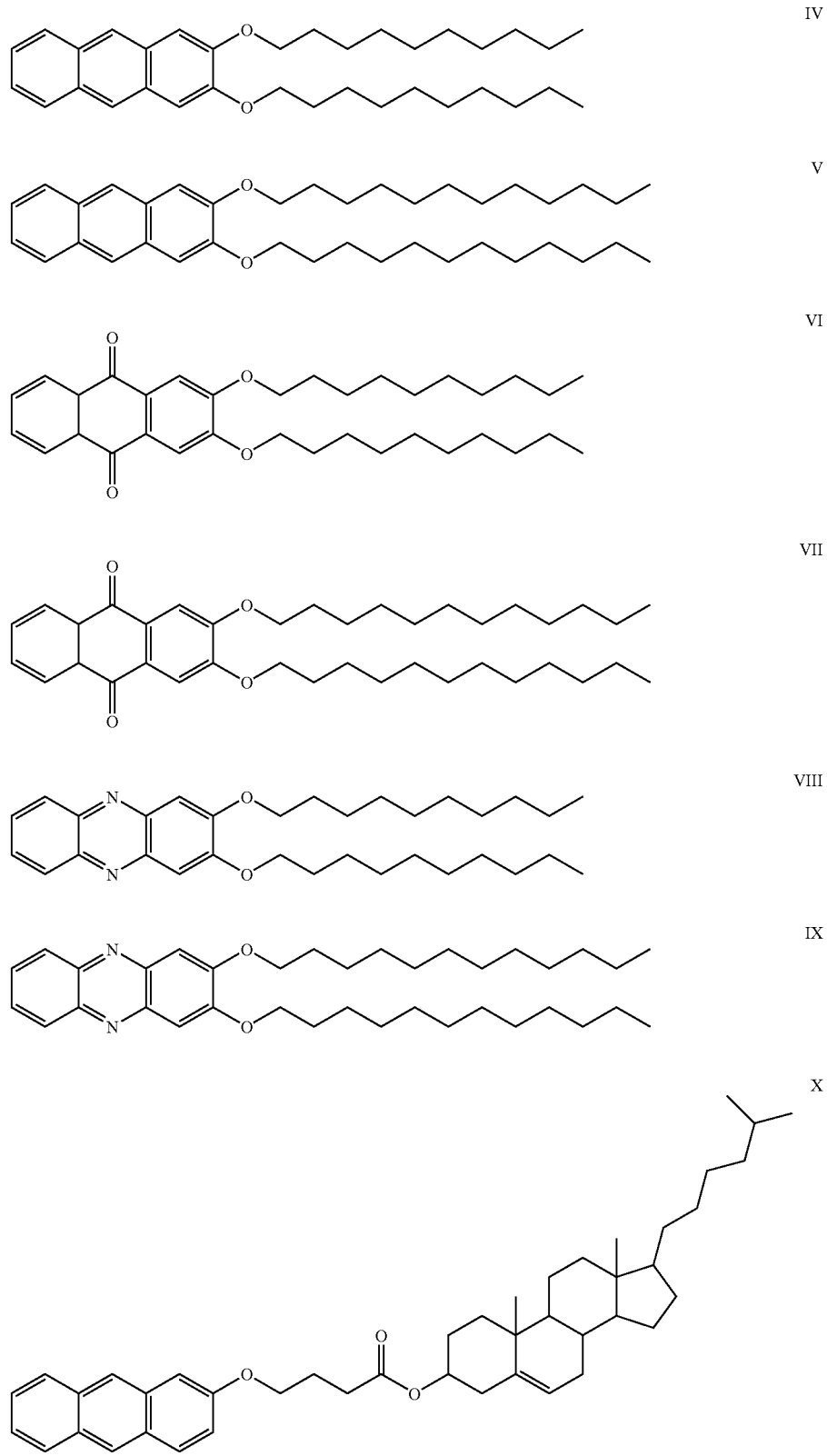

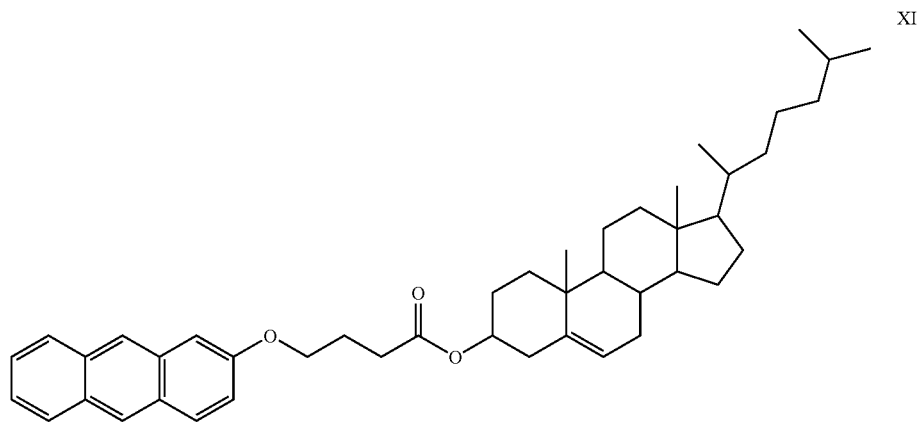
XI
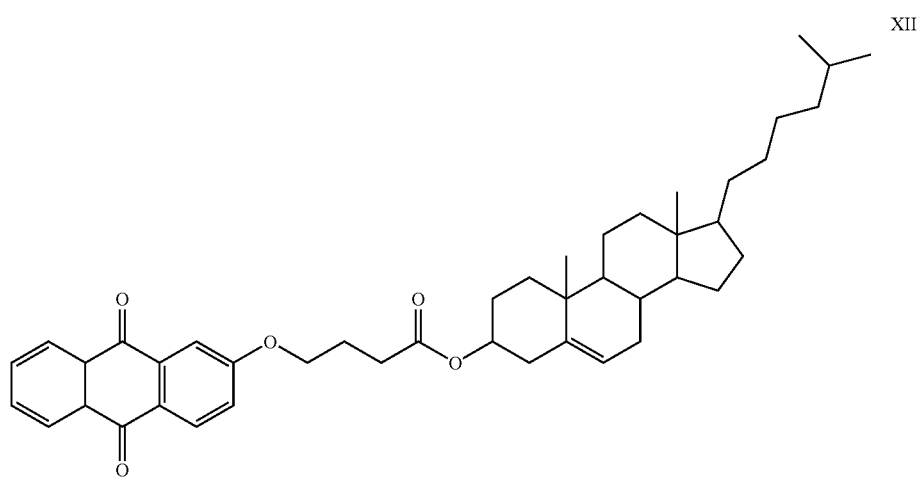
XII
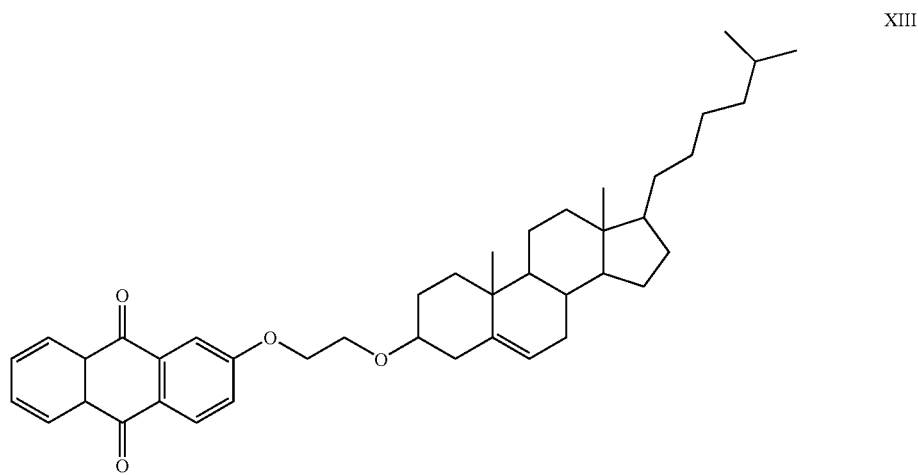
XIII

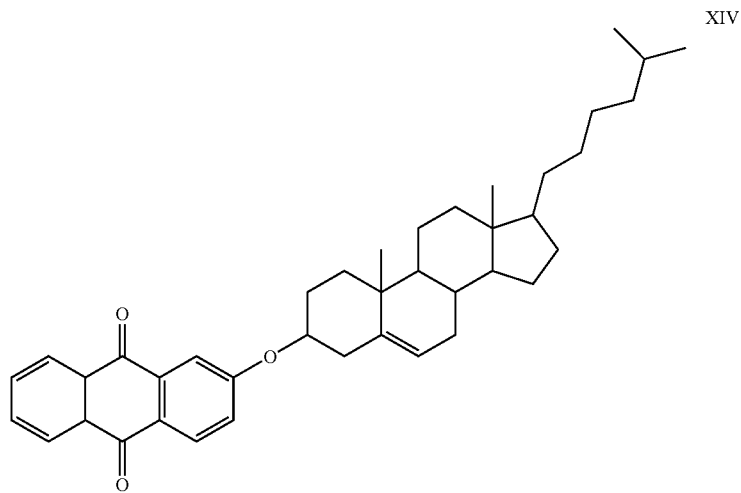 [SMILES: CC(C)CCCCC1CCC2C3CC=C4CC(Oc5ccc6c(c5)C(=O)C5C=CC=CC5C6=O)CCC4(C)C3CCC12C]
XIV
Other suitable organogelators include azobenzene steroid-based compounds such as molecules having a highly polar azobenzene group linked at C3 of a steroidal moiety. Some specific examples of suitable azobenzene steroid-based compounds include (but are not limited to) those of the formulas (Formulas XV through XVIII, respectively):
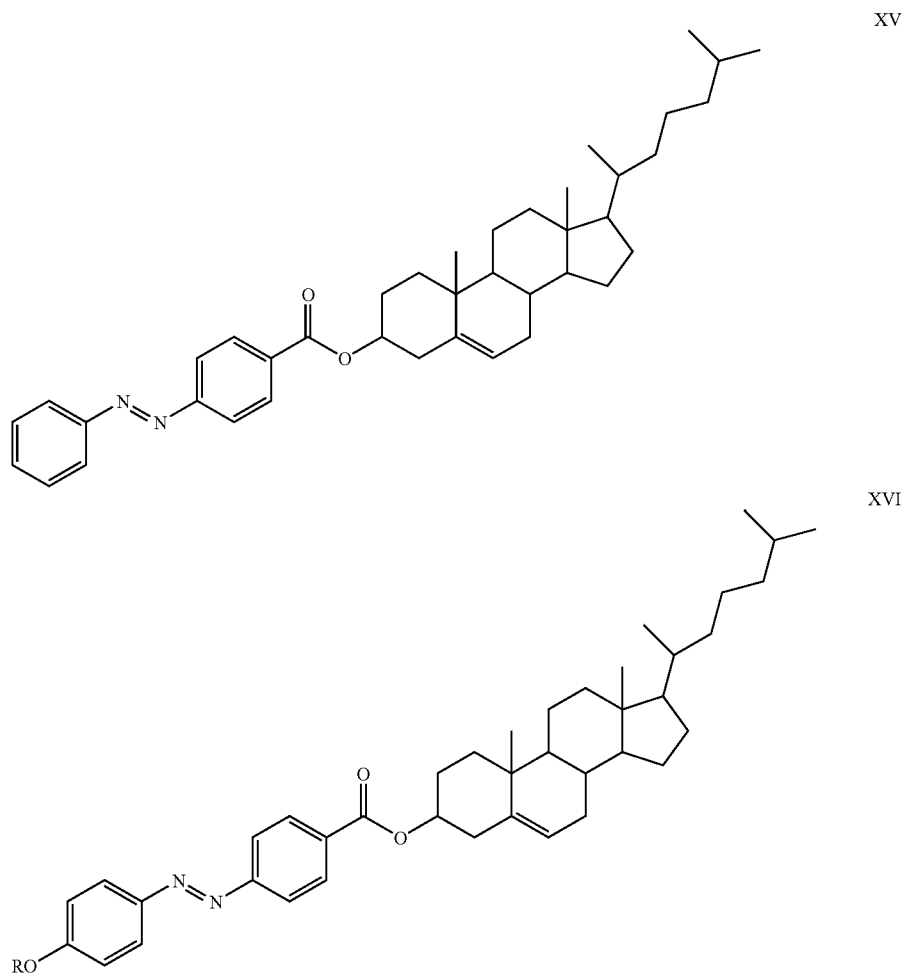

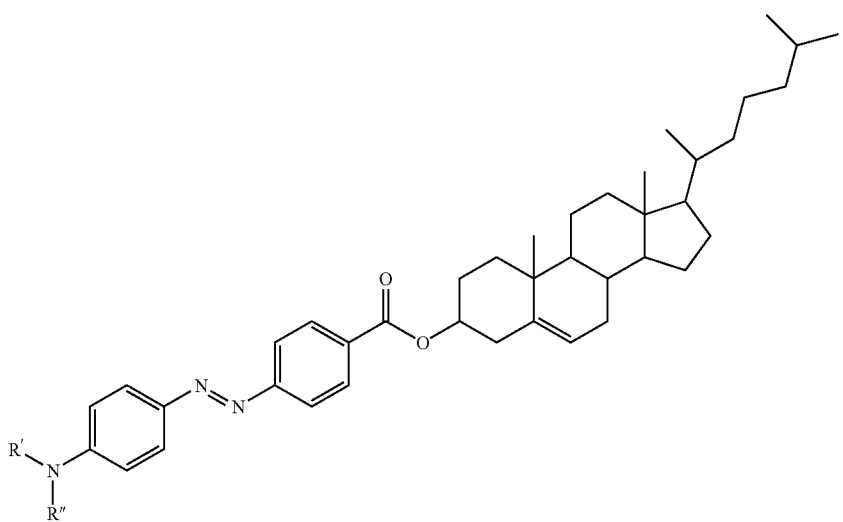

XVII

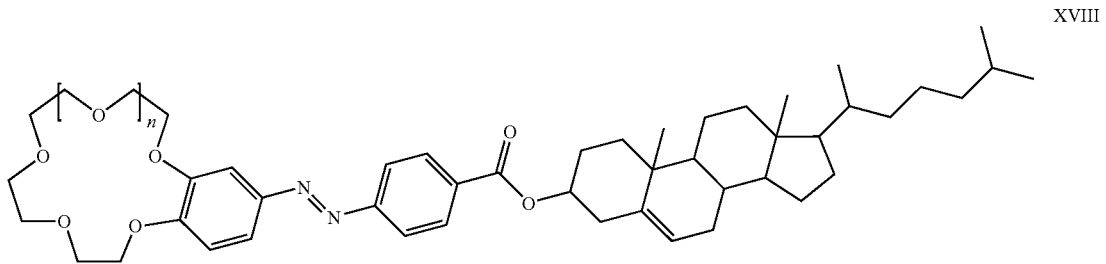

XVIII wherein: R (in Formula XVI) is a linear or branched alkyl group with 1 to 18 carbon atoms; R' and R" (in Formula XVII), each independently of each other, is a linear or branched alkyl group with 1 to 18 carbon atoms; and n (in Formula XVIII) is an integer of 1 to 4.

Other examples of suitable organogelators include amino acid-based compounds such as 2-octyldodecyl 4-[[[(1-naphthylamino)carbonyl]amino]benzoate; organometallic compounds such as 2,3,6,7,10,11-hexapentoxytriphenylene- and hexakis(n-hexyloxy)triphenylene-substituted metalloporphyrins, such as a long-chain ester of meso-tetrakis(p-carboxyphenyl)porphyrin, of metals such as Cu, Mn, Co, and Zn, for example; and macrocyclic compounds such as calyx[n] arenes (where n=4-8) with long alkanoyl chains at the para positions of the phenolic rings.

Other examples of suitable organogelators include partially fluorinated high molecular weight alkanes. In this context, "high molecular weight" means a molecular weight of at least 400 g/mol, and in some instances molecular weights of at least 800 g/mole, and in some instances at least 1,500 g/mol. Suitable partially fluorinated high molecular weight alkanes include those of the general formula (Formula XIX):

$F(CF_2)_n(CH_2)_mH$ wherein n is an integer of 6 to 24 representing the number of repeat —$CF_2$-units, and m is an integer of 6 to 20 representing the number of repeat —$CH_2$-units. Some specific examples of suitable partially fluorinated high molecular weight alkanes include, but are not limited to the following (Formulas XX through XXIII, respectively): $F(CF_2)_8(CH_2)_{12}H$; $F(CF_2)_{10}(CH_2)_{12}H$; $F(CF_2)_{15}(CH_2)_{12}H$; and $F(CF_2)_{12}(CH_2)_8H$.

Other examples of suitable organogelators include: high molecular weight alkanes with one heteroatom (i.e., an atom other than carbon or hydrogen) covalently bonded thereto. In this context, "high molecular weight" means compounds with at least 10 carbon atoms, and in some instances 14 carbon atoms or more. A counterion is not considered a heteroatom for the purposes of this definition; for example, if the compound is a quaternary ammonium compound having one nitrogen atom, the anion associated with the positively charged nitrogen atom is not considered a heteroatom. Some specific examples of suitable high molecular weight alkanes with one heteroatom include, but are not limited to the following (Formulas XXIV through XXVIII, respectively):

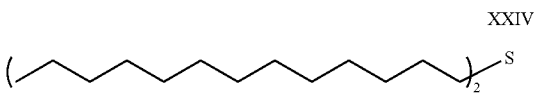

XXIV

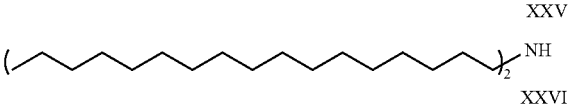

XXV

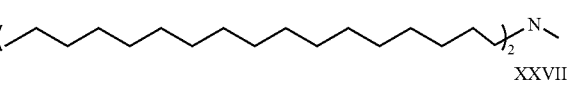

XXVI

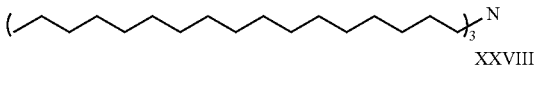

XXVII

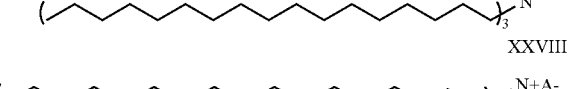

XXVIII wherein A– (of Formula XXVIII) is an anion that may be, for example, a halogen, a pseudohalogen, $PF_6$, $BF_4$, $ClO_4$, a carboxylate, or a mixture thereof.

Other examples of suitable organogelators include chiral tartrate compounds. Suitable chiral tartrate compounds include those of the general formula XXIX:

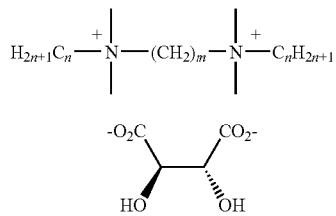
XXIX wherein (in Formula XXIX): n is an integer of 4 to 20 and m is an integer of 2 to 6. Some specific examples of chiral tartrate compounds include N,N'-dihexadecyl-N,N,N',N'-tetramethyl-1,2-ethanediammonium-L-tartrate, N,N'-dihexadecyl-N,N,N',N'-tetramethyl-1,2-ethanediammonium-D-tartrate, N,N'-dioctadecyl-N,N,N',N'-tetramethyl-1,2-ethanediammonium-L-tartrate, and N,N'-dioctadecyl-N,N,N',N'-tetramethyl-1,2-ethanediammonium-L-tartrate.

Other examples of suitable organogelators include chiral butenolide-based compounds. Some specific examples of chiral butenolide-based compounds include those of the following formula (Formula XXXI):

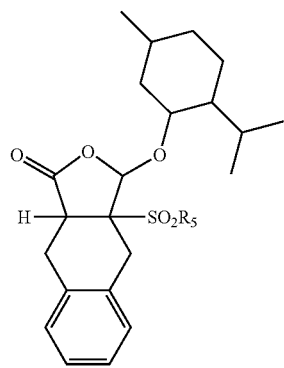
XXXI wherein $R_5$ of Formula XXXI is any one of the following groups (Formulas XXXII through XXXVIII, respectively):

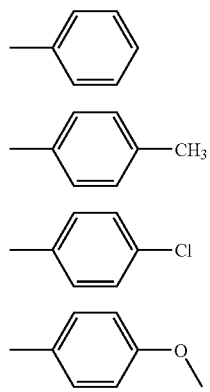

XXXII

XXXIII

XXXIV

XXXV

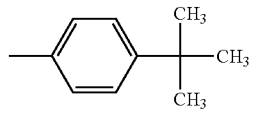
XXXVI

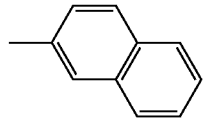
XXXVII

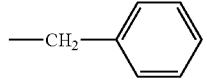
XXXVIII

These chiral materials exist in various stereoisomeric forms.

Other examples of suitable organogelators include urea-based compounds. Suitable urea-based compounds include those of the general formulas (Formulas XXXIX through XLII, respectively):

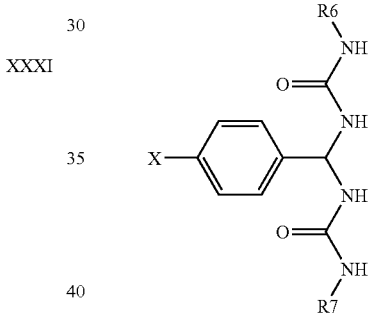
XXXIX

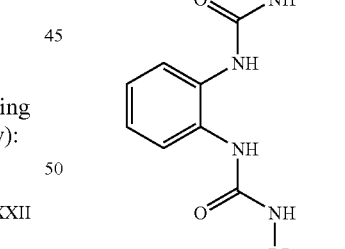
XL

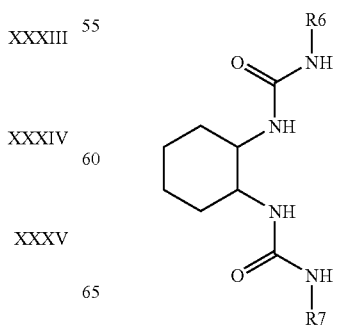
XLI

-continued

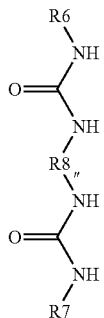

XLII wherein: X (of Formula XXXIX) is a hydrogen atom, a halogen atom, a nitro group, an alkoxy group, an amino group, or the like; R6 and R7 (of each of the formulas), each independently of the other, can be a hydrogen atom, an alkyl group (including linear, branched, saturated, unsaturated, cyclic, unsubstituted, and substituted alkyl groups, and wherein heteroatoms, such as oxygen, nitrogen, sulfur, silicon, phosphorus, and/or functional groups, such as carbonyl groups, may or may not be present in the alkyl group), an aryl group (including substituted or unsubstituted aryl groups, and wherein heteroatoms, such as oxygen, nitrogen, sulfur, silicon, phosphorus, and/or functional groups, such as carbonyl groups, may or may not be present in the aryl group), or a combination of alkyl and aryl groups; and R8 (of Formula XLII) can be an alkylene group (including linear, branched, saturated, unsaturated, cyclic, unsubstituted, and substituted alkylene groups, and wherein heteroatoms, such as oxygen, nitrogen, sulfur, silicon, phosphorus, and/or functional groups, such as carbonyl groups, may or may not be present in the alkylene group), an arylene group (including substituted or unsubstituted arylene groups, and wherein heteroatoms, such as oxygen, nitrogen, sulfur, silicon, phosphorus, and/or functional groups, such as carbonyl groups, may or may not be present in the arylene group), or a combination thereof. Some specific examples of urea-based compounds include the following (Formulas XLIII through XLIX, respectively):

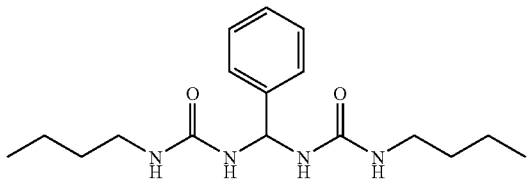

XLIII

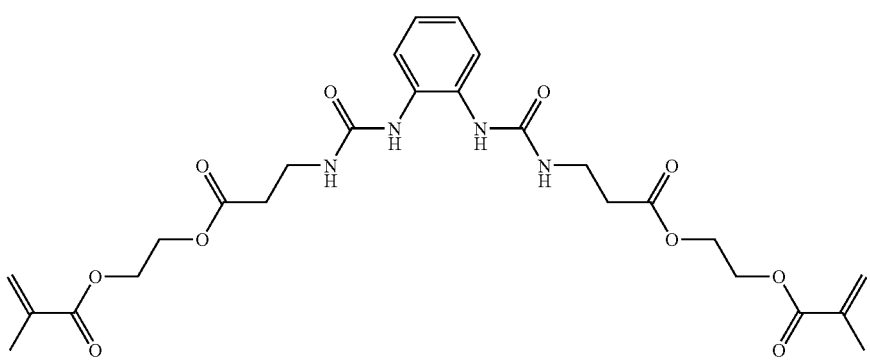

XLIV

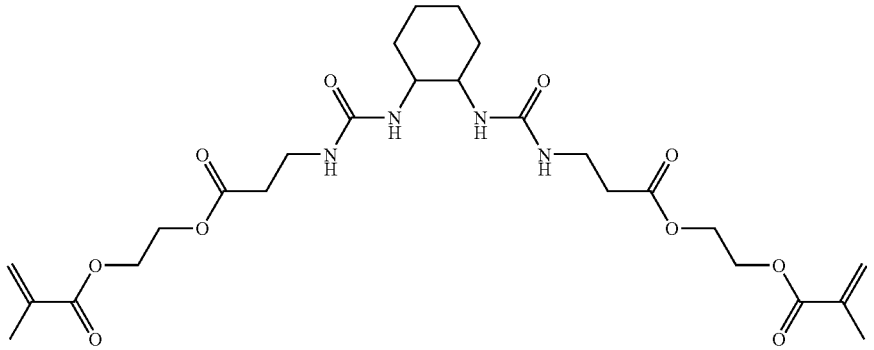

XLV

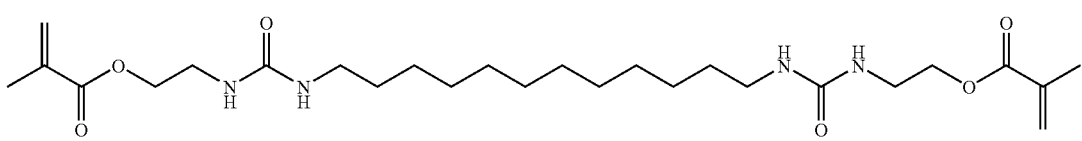

XLVI

XLVII

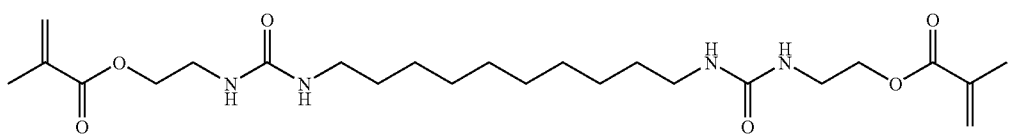

XLVIII

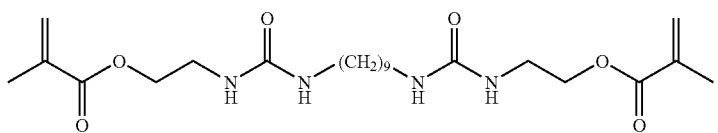

XLIX

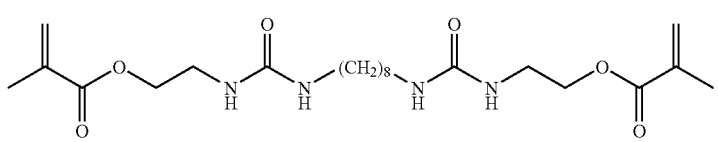

Other examples of suitable organogelators include barbiturates. Suitable barbiturates include those of the general formula (Formula L):

L

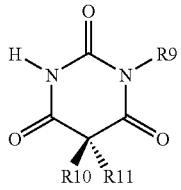

wherein R9, R10, and R11, each independently of the other, can be a hydrogen atom, an alkyl group (including linear, branched, saturated, unsaturated, cyclic, unsubstituted, and substituted alkyl groups, and wherein heteroatoms, such as oxygen, nitrogen, sulfur, silicon, phosphorus, and/or functional groups, such as carbonyl groups, may or may not be present in the alkyl group), an aryl group (including substituted or unsubstituted aryl groups, and wherein heteroatoms, such as oxygen, nitrogen, sulfur, silicon, phosphorus, and/or functional groups, such as carbonyl groups, may or may not be present in the aryl group), or a combination of alkyl and aryl groups. Some specific examples of barbiturates include the following (Formulas LI and LII):

LI

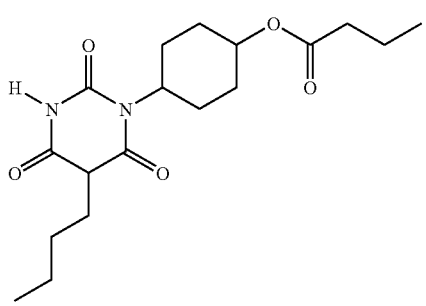

LII

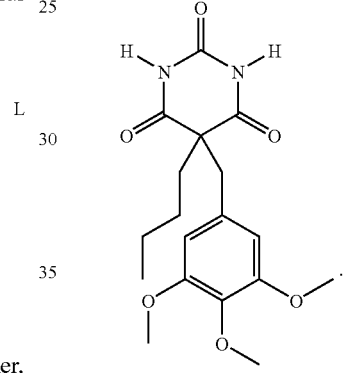

Other examples of suitable organogelators includes chiral amide-based compounds. Suitable chiral amide-based compounds include those of the general formulas (Formulas LIII and LIV):

LIII

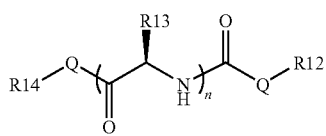

LIV

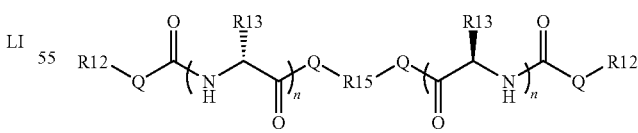

wherein: R12, R13, and R14 (of each formula), each independently of the other, can be a hydrogen atom, an alkyl group (including linear, branched, saturated, unsaturated, cyclic, unsubstituted, and substituted alkyl groups, and wherein heteroatoms, such as oxygen, nitrogen, sulfur, silicon, phosphorus, and/or functional groups, such as carbonyl groups, may or may not be present in the alkyl group), an aryl group (including substituted or unsubstituted aryl groups, and wherein heteroatoms, such as oxygen, nitrogen, sulfur, silicon, phosphorus, and/or functional groups, such as carbonyl groups, may or may not be present in the aryl group), or a combination of alkyl and aryl groups; n (of each formula) is 1, 2, or 3; Q (of each formula) is a bond, O, S, NH, or alkyl-substituted nitrogen; and R15 (of Formula LIV) is an alkylene group (including linear, branched, saturated, unsaturated, cyclic, unsubstituted, and substituted alkylene groups, and wherein heteroatoms, such as oxygen, nitrogen, sulfur, silicon, phosphorus, and/or functional groups, such as carbonyl groups, may or may not be present in the alkylene group), an arylene group (including substituted or unsubstituted arylene groups, and wherein heteroatoms, such as oxygen, nitrogen, sulfur, silicon, phosphorus, and/or functional groups, such as carbonyl groups, may or may not be present in the arylene group), or a combination thereof. In formulas LIII and LIV, the dashed and wedged bonds do not imply that the amino acid is of a specific chirality; thus, the structures could include isomers of either D or L configuration.

Some specific examples of chiral amide-based compounds include the following (Formulas LV through LVII, respectively):

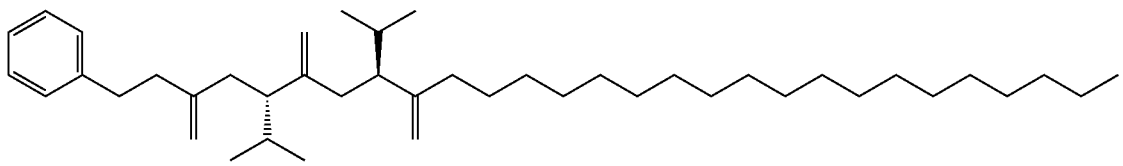

wherein: each M is independently hydrogen or a polymerizable group (particularly groups polymerizable via a free radical mechanism, such as methacrylate, acrylate, vinyl, styryl, etc.); each X is independently an alkylene group, cycloalkylene group, arylene group, arenylene group, or a combination thereof; and n is 1 to 3. The alkylene, cycloalkylene, arylene, or arenylene groups can be substituted (e.g., with halogens) or be unsubstituted and may or may not include heteroatoms, such as oxygen, nitrogen, sulfur, silicon, phosphorus, and/or functional groups, such as carbonyl groups, etc. Preferably, in Formula I if M is other than hydrogen, it includes no more than 8 carbon atoms, and more preferably no more than 4 carbon atoms (e.g., a methacrylate). Preferably, in Formula I, X includes no more than 20 carbon atoms. Both X and M preferably independently include at least 3 carbon atoms, and in some instances at least 4 carbon atoms.

LV

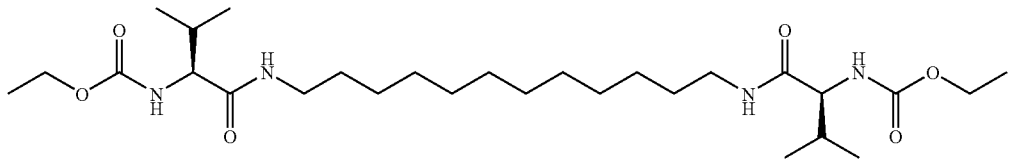

LVI

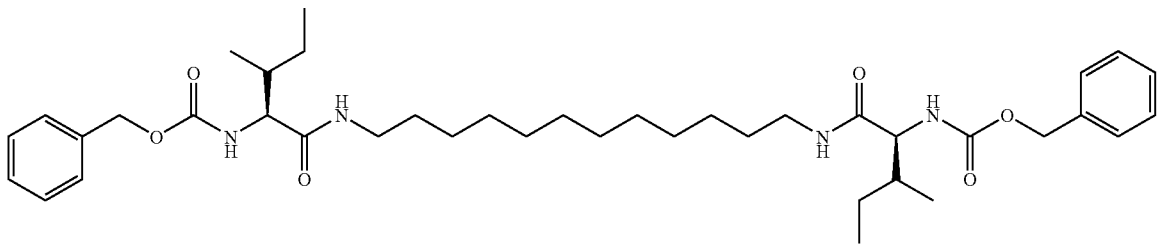

LVII

An example of a particularly useful nonpolymerizable organogelator is dibenzilidine sorbitol (DBS), which is commercially available under the trade designation MILLITHIX 925S from Milliken & Co., Spartanburg, S.C.

One suitable, and preferred, class of organogelators is that of oxamide compounds. Examples of this class of materials include those of the general formula (Formula I):

Some specific examples of suitable oxamide organogelators include, but are not limited to, those of the formulas (Formulas LVIII through LXV, respectively):

LVIII

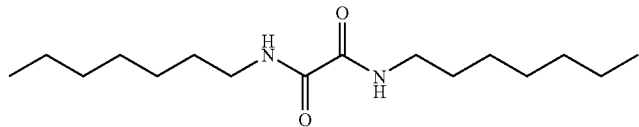

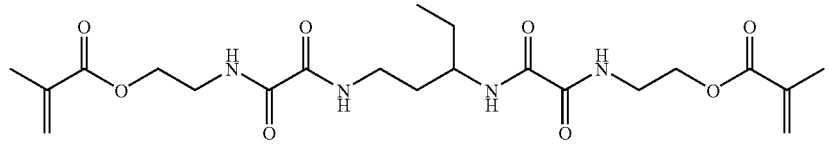

LIX

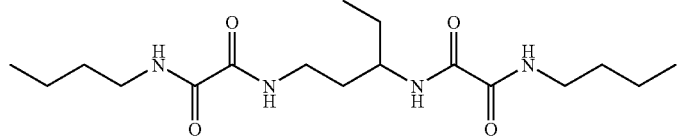

LX

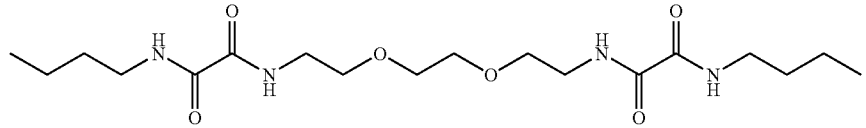

LXI

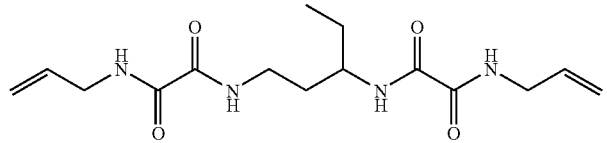

LXII

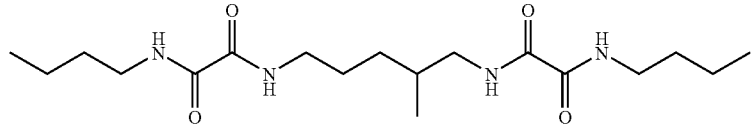

LXIII

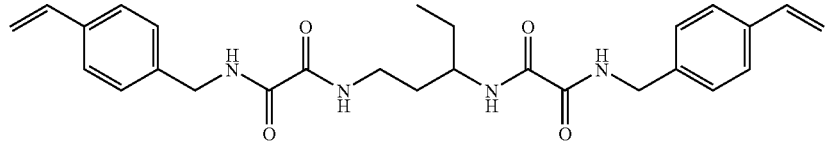

LXIV

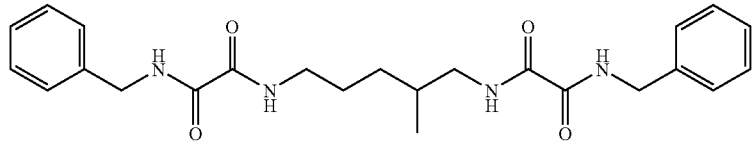

LXV

Compounds of this class can be prepared by reacting a dialkyloxalate with two equivalents of an amine. Tetraamides (n=2) can be prepared by a two step sequence. In the first step, an excess of a dialkyloxalate is reacted with a diamine to prepare an intermediate derivative. This intermediate is then reacted with an amine to give the final oxamide organogelator (Formula LXVI) as shown:

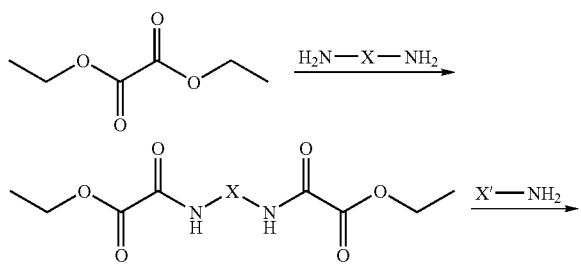

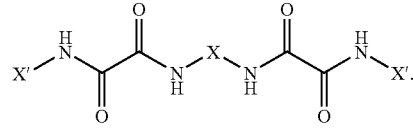

LXVI wherein X is independently an alkylene group, cycloalkylene group, arylene group, arenylene group, or a combination thereof (wherein the alkylene, cycloalkylene, arylene, or arenylene groups can be substituted (e.g., with halogens) or be unsubstituted and may or may not include heteroatoms, such as oxygen, nitrogen, sulfur, silicon, phosphorus, and/or functional groups, such as carbonyl groups, etc.); and X' is independently an alkyl group, cycloalkyl group, aryl group, arenyl group, or a combination thereof (wherein the alkyl, cycloalkyl, aryl, or arenyl groups can be substituted (e.g., with halogens) or be unsubstituted and may or may not include heteroatoms, such as oxygen, nitrogen, sulfur, silicon, phosphorus, and/or functional groups, such as carbonyl groups, etc.). Further details regarding the preparation of oxamides can be found in L. M. Rice et al., *J. Chem. Soc.*, 75, 242-243 (1953).

Preferred polymerizable organogelators include alkyl diureamono- and multi-methacylates, acrylated amino acid derivatives, and methacrylated or styryl sugar derivatives. Examples of such materials are shown below (Formulas LXVII through LXXIII):

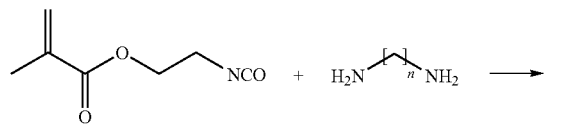

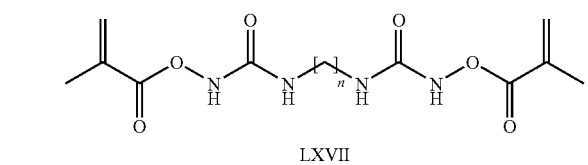

LXVII

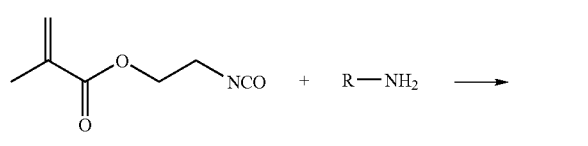

LXVIII

LXIX

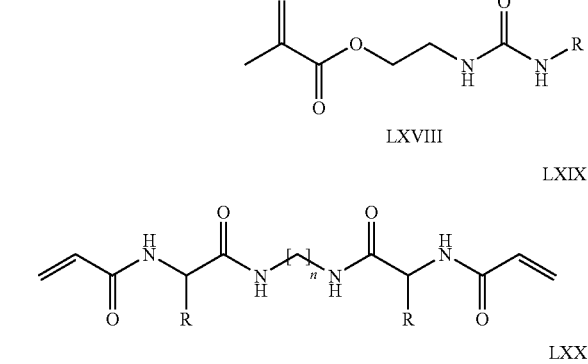

LXX

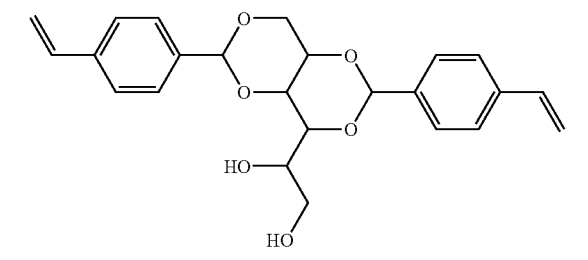

LXXI

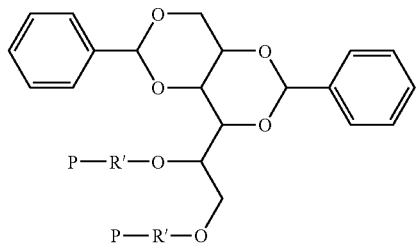

LXXII

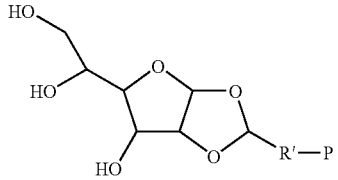

LXXIII wherein: n (of Formulas LXVII and LXIX) is an integer of 1 to 20; R (of Formulas LXVIII and LXIX) can be an alkyl group (including linear, branched, saturated, unsaturated, cyclic, unsubstituted, and substituted alkyl groups, and wherein heteroatoms, such as oxygen, nitrogen, sulfur, silicon, phosphorus, and/or functional groups, such as carbonyl groups, may or may not be present in the alkyl group), an aryl group (including substituted or unsubstituted aryl groups, and wherein heteroatoms, such as oxygen, nitrogen, sulfur, silicon, phosphorus, and/or functional groups, such as carbonyl groups, may or may not be present in the aryl group), or a combination thereof, R' (of Formulas LXXI, LXXII, and LXXIII) can be an alkylene group (including linear, branched, saturated, unsaturated, cyclic, unsubstituted, and substituted alkylene groups, and wherein heteroatoms, such as oxygen, nitrogen, sulfur, silicon, phosphorus, and/or functional groups, such as carbonyl groups, may or may not be present in the alkylene group), an arylene group (including substituted or unsubstituted arylene groups, and wherein heteroatoms, such as oxygen, nitrogen, sulfur, silicon, phosphorus, and/or functional groups, such as carbonyl groups, may or may not be present in the arylene group), or a combination thereof; and P (of Formulas LXXI, LXXII, and LXXIII) is a polymerizable group (particularly a group polymerizable via a free radical mechanism such as methacrylate, acrylate, vinyl, styryl).

Another suitable, and preferred, class of organogelators is that of amino sugars, including linear amino sugars and cyclic amino sugars.

In one aspect, the organogelator is a linear amino sugar of Formula LXXV or a pharmaceutically acceptable salt thereof:

LXXV wherein $R^1$ and $R^2$ are independently selected from the group consisting of a hydrogen atom, an alkyl group, $C(O)R^3$, and $SO_2R^4$; $R^3$ and $R^4$ are independently selected from the group consisting of an alkyl group, an aryl group, and an aralkyl group; and n is an integer from about 2 to about 5.

In Formula LXXV, the groups $R^1$ and $R^2$ are independently selected from the group consisting of a hydrogen atom, an alkyl group, $C(O)R^3$, and $SO_2R^4$. Each of $R^1$ and $R^2$ may be a hydrogen atom, each of $R^1$ and $R^2$ may be an alkyl group, each of $R^1$ and $R^2$ may be $C(O)R^3$, or each of $R^1$ and $R^2$ may be $SO_2R^4$. In some embodiments, $R^1$ may be a hydrogen atom and $R^2$ may be an alkyl group, $C(O)R^3$, or $SO2R^4$. In other embodiments, $R^1$ may be an alkyl group, and $R^2$ may be $C(O)R^3$, or $SO_2R^4$. In still other embodiments, $R^1$ may be $C(O)R^3$, and $R^2$ may be $SO_2R^4$. When either or both of $R^1$ and $R^2$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. When each of $R^1$ and $R^2$ comprises an alkyl group, $R^1$ and $R^2$ may comprise the same alkyl group, or $R^1$ and $R^2$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

In Formula LXXV, the groups $R^3$ and $R^4$ are independently selected from the group consisting of an alkyl group, an aryl group, and an aralkyl group. When either or both of $R^3$ or $R^4$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. In compounds of Formula LXXV or pharmaceutically acceptable salts thereof, when both $R^3$ and $R^4$ groups are present, and when each of $R^3$ and $R^4$ comprises an alkyl group, $R^3$ and $R^4$ may comprise the same alkyl group, or $R^3$ and $R^4$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

In Formula LXXV, when either or both of $R^3$ or $R^4$ are an aryl group, the aryl group may comprise one arene ring or more than one arene ring. Arene rings may comprise up to six carbon atoms, up to eight carbon atoms, up to ten carbon atoms, up to twelve carbon atoms, up to fourteen carbon atoms, up to sixteen carbon atoms, or up to eighteen carbon atoms. Arene rings may comprise a heteroatom, for example, nitrogen, oxygen, or sulfur. If more than one arene ring is present, the arene rings may be fused together, or they may be joined by a chemical bond. In compounds of Formula LXXV or pharmaceutically acceptable salts thereof, when both $R^3$ and $R^4$ groups are present, and when each of $R^3$ and $R^4$ comprises an aryl group, $R^3$ and $R^4$ may comprise the same aryl group, or $R^3$ and $R^4$ may comprise different aryl groups. Non-limiting examples of aryl groups include substituted and unsubstituted phenyl, 1-naphthyl, 2-naphthyl, 9-anthracenyl.

In Formula LXXV, when either or both of $R^3$ or $R^4$ are an aralkyl group, the aralkyl group may comprise one arene ring or more than one arene ring. The aralkyl group may comprise up to six carbon atoms, up to eight carbon atoms, up to ten carbon atoms, up to twelve carbon atoms, up to fourteen carbon atoms, up to sixteen carbon atoms, up to eighteen carbon atoms, or up to twenty carbon atoms. If more than one arene ring is present in the aralkyl group, the arene rings may be fused together, or they may be joined by a chemical bond. Arene rings may comprise a heteroatom, for example, nitrogen, oxygen, or sulfur. In compounds of Formula LXXV or pharmaceutically acceptable salts thereof, when both $R^3$ and $R^4$ groups are present, and when each of $R^3$ and $R^4$ comprises an aralkyl group, $R^3$ and $R^4$ may comprise the same aralkyl group, or $R^3$ and $R^4$ may comprise different aralkyl groups. Non-limiting examples of aralkyl groups include benzyl, 1-phenylethyl, 2-phenylethyl, 3-phenylpropyl, 2-naphthylethyl, and 9-anthracenylmethyl.

In Formula LXXV, n is an integer from about 2 to about 5. In some embodiments, the dental composition comprises a compound of Formula LXXV, or a pharmaceutically acceptable salt thereof, wherein n is an integer having a value of about 5, about 4, about 3, or about 2. In some embodiments, n is an integer having a value of 5, or 4, or 3, or 2. It is understood that a dental composition of the present invention may comprise more than one compound of Formula LXXV, or a pharmaceutically acceptable salt thereof, and that the compounds may be represented by Formula LXXV with different integer values of n. In these embodiments, the average value of n of a composition may be a non-integer.

In some embodiments, $R^1$ and $R^2$ are each a hydrogen atom. In some embodiments, pharmaceutically acceptable salts comprise ammonium halides. In certain embodiments, the dental composition comprises a compound of Formula LXXVI or a pharmaceutically acceptable salt thereof. In some embodiments, the salt comprises an ammonium halide. In a specific embodiment, the ammonium halide comprises an ammonium chloride.

LXXVI

In some embodiments of Formula LXXV, $R^1$ comprises an alkyl group and $R^2$ is $C(O)R^3$, where $R^3$ comprises an alkyl group. In certain embodiments, $R^1$ comprises an alkyl group having from about one to about four carbon atoms, and $R^3$ comprises an alkyl group having from about four to about sixteen carbon atoms. In some embodiments, $R^1$ comprises a methyl group, and $R^3$ comprises an alkyl group having seven, eight, or nine carbon atoms. In some embodiments, the dental composition comprises a compound of Formula LXXVII, Formula LXXVIII, or Formula LXXIX.

LXXVII

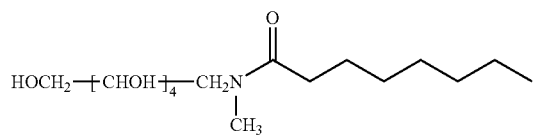

-continued

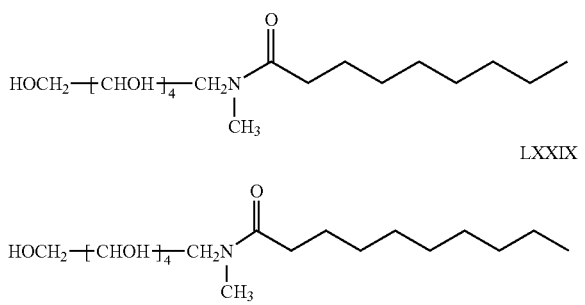

LXXVIII

LXXIX

In some embodiments of Formula LXXV, $R^1$ is a hydrogen atom and $R^2$ comprises an alkyl group. In some embodiments pharmaceutically acceptable salts comprise ammonium halides. In some embodiments, the alkyl group comprises from about one to about eight carbon atoms. In certain embodiments, the dental composition comprises a compound of Formula LXXX or a pharmaceutically acceptable salt thereof. The salt may comprise an ammonium halide. In some embodiments, the ammonium halide comprises an ammonium chloride. In certain embodiments, the dental composition comprises a compound of Formula LXXXI or a pharmaceutically acceptable salt thereof. The salt may comprise an ammonium halide. In some embodiments, the ammonium halide comprises an ammonium chloride. In some embodiments, $R^1$ and $R^2$ independently comprise an alkyl group having from about one to about eight carbon atoms. In certain embodiments, the dental composition comprises a compound of Formula LXXXII or a pharmaceutically acceptable salt thereof. The salt may comprise an ammonium halide. In some embodiments, the ammonium halide comprises an ammonium chloride.

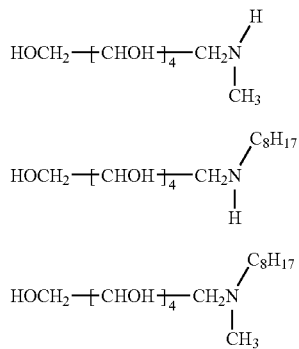

LXXX

LXXXI

LXXXII

It is recognized that the compounds of Formulas LXXV through LXXXII comprise chiral carbon atoms. For simplicity, in these formulas, the stereochemical configuration about each of the chiral carbon atoms is not specified. It is intended that such formulas, however, as used in this description and in the claims, represents each of the compounds having any of the possible stereochemical configurations. In some embodiments, the compounds of Formulas LXXVI though LXXXII are amino sugar alcohols and derivatives having the common names D-glucamine, N-methyl-N-octanoyl-D-glucamine, N-methyl-N-nonanoyl-D-glucamine, N-methyl-N-decanoyl-D-glucamine, N-octyl-D-glucamine, and N-methyl-N-octyl-D-glucamine, respectively.

In another aspect, the organogelator is a cyclic amino sugar of Formula LXXXIII or a pharmaceutically acceptable salt thereof:

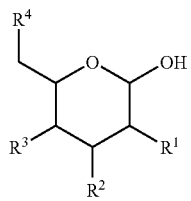

LXXXIII wherein: $R^1$, $R^2$, and $R^3$ are independently selected from the group consisting of OH and $NR^5R^6$; $R^4$ is selected from the group consisting of OH, $OP(O)(OH)_2$, $OSO_3H$, and $NR^5R^6$; $R^5$ and $R^6$ are independently selected from the group consisting of a hydrogen atom, an alkyl group, $C(O)R^7$, and $SO_2R^8$; $R^7$ and $R^8$ are independently selected from the group consisting of an alkyl group, an aryl group, or an aralkyl group; provided that at least one of $R^1$, $R^2$, $R^3$, and $R^4$ is $NR^5R^6$.

It is recognized that the compounds of Formula LXXXIII comprise chiral carbon atoms. For simplicity, in Formula LXXXIII the stereochemical configuration about each of the chiral carbon atoms is not specified. It is intended that Formula LXXXIII, as used in this description and in the claims, represents each of the compounds having any of the possible stereochemical configurations.

In Formula LXXXIII, at least one of $R^1$, $R^2$, $R^3$, and $R^4$ is $NR^5R^6$. $R^1$, $R^2$, and $R^3$ are independently selected from the group consisting of OH and $NR^5R^6$. Each of $R^1$, $R^2$, and $R^3$ may be OH, any two of $R^1$, $R^2$, and $R^3$ may be OH, or any one of $R^1$, $R^2$, and $R^3$ may be OH. Each of $R^1$, $R^2$, and $R^3$ may be $NR^5R^6$, any two of $R^1$, $R^2$, and $R^3$ may be $NR^5R^6$, or any one of $R^1$, $R^2$, and $R^3$ may be $NR^5R^6$. $R^4$ is selected from the group consisting of OH, $OP(O)(OH)_2$, $OSO_3H$, and $NR^5R^6$. In some embodiments, $R^4$ is OH. In other embodiments, $R^4$ is $OP(O)(OH)_2$. In other embodiments, $R^4$ is $OSO_3H$. In other embodiments, $R^4$ is $NR^5R^6$.

In Formula LXXXIII, $R^5$ and $R^6$ are independently selected from the group consisting of a hydrogen atom, an alkyl group, $C(O)R^7$, and $SO_2R^8$. Each of $R^5$ and $R^6$ may be a hydrogen atom, each of $R^5$ and $R^6$ may be an alkyl group, each of $R^5$ and $R^6$ may be $C(O)R^7$, or each of $R^5$ and $R^6$ may be $SO_2R^8$. In some embodiments, $R^5$ may be a hydrogen atom and $R^6$ may be an alkyl group, $C(O)R^7$, or $SO_2R^8$. In other embodiments, $R^5$ may be an alkyl group, and $R^6$ may be $C(O)R^7$, or $SO_2R^8$. In still other embodiments, $R^5$ may be $C(O)R^7$, and $R^6$ may be $SO_2R^8$. When either or both of $R^5$ and $R^6$ is an alkyl group, the alkyl group may comprise about one carbon atom, more than about one carbon atom, more than about two carbon atoms, more than about four carbons atoms, more than about six carbon atoms, more than about eight carbon atoms, more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. When each of $R^5$ and $R^6$ comprises an alkyl group, $R^5$ and $R^6$ may comprise the same alkyl group, or $R^5$ and $R^6$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

In Formula LXXXIII, $R^7$ and $R^8$ are independently selected from the group consisting of an alkyl group, an aryl group, or an aralkyl group. When either or both of $R^7$ or $R^8$ is an alkyl group, the alkyl group may comprise about one carbon atom, more than about one carbon atom, more than about two carbon atoms, more than about four carbons atoms, more than about six carbon atoms, more than about eight carbon atoms, or more than about ten carbon atoms, more than about twelve carbon atoms, more than about fourteen carbon atoms, more than about sixteen carbon atoms, or more than about eighteen carbon atoms. In some embodiments, the alkyl group comprises less than about thirty carbon atoms, less than about twenty-six carbon atoms, less than about twenty-two carbon atoms, or less than about twenty carbon atoms. In some embodiments, the alkyl group comprises a straight chain alkyl group. In other embodiments, the alkyl group comprises a branched alkyl group. In still other embodiments, the alkyl group comprises a cyclic alkyl group. In compounds of Formula I or pharmaceutically acceptable salts thereof, when both $R^7$ and $R^8$ groups are present, and when each of $R^7$ and $R^8$ comprises an alkyl group, $R^7$ and $R^8$ may comprise the same alkyl group, or $R^7$ and $R^8$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

In Formula LXXXIII, when either or both of $R^7$ or $R^8$ are an aryl group, the aryl group may comprise one arene ring or more than one arene ring. Arene rings may comprise up to six carbon atoms, up to eight carbon atoms, up to ten carbon atoms, up to twelve carbon atoms, up to fourteen carbon atoms, up to sixteen carbon atoms, or up to eighteen carbon atoms. Arene rings may comprise a heteroatom, for example, nitrogen, oxygen, or sulfur. If more than one arene ring is present in an aryl group, the arene rings may be fused together, or they may be joined by a chemical bond. In compounds of Formula LXXXIII or pharmaceutically acceptable salts thereof, when both $R^7$ and $R^8$ groups are present, and when each of $R^7$ and $R^8$ comprises an aryl group, $R^7$ and $R^8$ may comprise the same aryl group, or $R^7$ and $R^8$ may comprise different aryl groups. Non-limiting examples of aryl groups include substituted and unsubstituted phenyl, 1-naphthyl, 2-naphthyl, 9-anthracenyl, and biphenyl.

In Formula LXXXIII, when either or both of $R^7$ or $R^8$ are an aralkyl group, the aralkyl group may comprise one arene ring or more than one arene ring. The aralkyl group may comprise up to six carbon atoms, up to eight carbon atoms, up to ten carbon atoms, up to twelve carbon atoms, up to fourteen carbon atoms, up to sixteen carbon atoms, up to eighteen carbon atoms, or up to twenty carbon atoms. If more than one arene ring is present in the aralkyl group, the arene rings may be fused together, or they may be joined by a chemical bond. Arene rings may comprise a heteroatom, for example, nitrogen, oxygen, or sulfur. In compounds of Formula LXXXIII or pharmaceutically acceptable salts thereof, when both $R^7$ and $R^8$ groups are present, and when each of $R^7$ and $R^8$ comprises an aralkyl group, $R^7$ and $R^8$ may comprise the same aralkyl group, or $R^7$ and $R^8$ may comprise different aralkyl groups. Non-limiting examples of aralkyl groups include benzyl, 1-phenylethyl, 2-phenylethyl, 3-phenylpropyl, 2-naphthylethyl, and 9-anthracenylmethyl.

In some embodiments of Formula LXXXIII, $R^1$ is $NR^5R^6$, where $R^5$ and $R^6$ are each a hydrogen atom, and $R^2$, $R^3$, and $R^4$ are each OH. In some embodiments of Formula LXXXIII, pharmaceutically acceptable salts are selected from ammonium chlorides and ammonium sulfates. In some embodiments, the dental composition comprises a compound of Formula LXXXIV, Formula LXXXV, or Formula LXXXVI, or a pharmaceutically acceptable salt thereof. In some embodiments the salt comprises ammonium chlorides or ammonium sulfates.

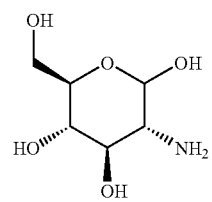

LXXXIV

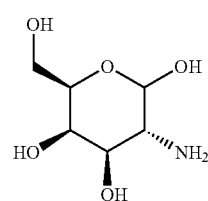

LXXXV

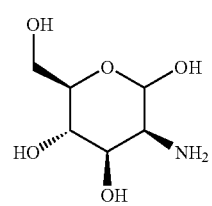

LXXXVI

In some embodiments of Formula LXXXIII, $R^1$ is $NR^5R^6$, where $R^5$ and $R^6$ are each a hydrogen atom, $R^2$ and $R^3$ are each OH, and $R^4$ is $OP(O)(OH)_2$. In a specific embodiment, the dental composition comprises a compound of Formula LXXXVII or a pharmaceutically acceptable salt thereof. The pharmaceutically acceptable salt may comprise a zwitterion.

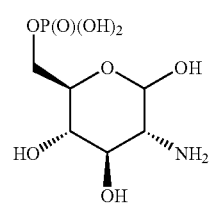

LXXXVII

In some embodiments of Formula LXXXIII, $R^1$ is $NR^5R^6$, where $R^5$ is $C(O)R^7$, and where $R^7$ is an alkyl group having twelve carbon atoms, an alkyl group having fourteen carbon atoms, or an alkyl group having sixteen carbon atoms, and $R^6$ is a hydrogen atom. In specific embodiments, the dental composition comprises a compound of Formula LXXXVIII, Formula LXXXIX, or Formula LXL.

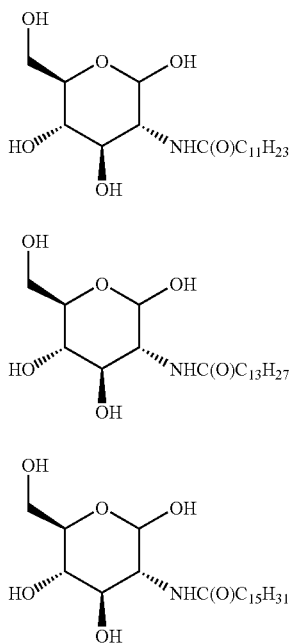

In Formulas LXXIV-LXL, the stereochemical configuration about four of the five chiral carbon atoms in each ring are specified using the conventional notation for the bonds. The stereochemical configuration about one chiral carbon atom in each ring is not specified. It is intended that these formulas, as used in this description and in the claims, represent each of the compounds having any of the possible stereochemical configurations. Among the useful compounds are compounds having the common names D-glucosamine, D-galactosamine, D-mannosamine, D-glucosamine-6-phosphate, N-dodecanoyl-D-glucosamine, N-tetradecanoyl-D-glucosamine, and N-hexadecanoyl-D-glucosamine.

Of the amino sugars, preferred compounds include the following:

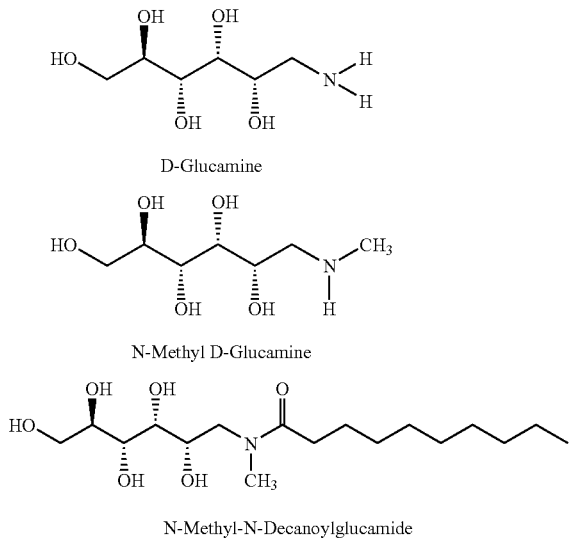

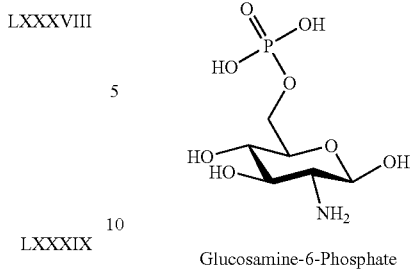

Glucosamine-6-Phosphate

Of the many classes of organogelators described herein, preferred ones are the urea-type or oxamides, and more preferred are polymerizable urea-type or oxamide organogelators. The most preferred derivatives are dibenzylidene sorbitol, the urea methacrylates, and the oxamide methacrylates. Preferred organogelators include those described in the Examples Section.

One or more organogelators can be included in hardenable compositions of the present invention preferably in an amount of at least 0.01 weight percent (wt-%), more preferably in an amount of at least 0.1 wt-%, even more preferably in an amount of at least 0.2 wt-%, and even more preferably in an amount of at least 0.4 wt-%, based on the total weight of the organogelator plus polymerizable component (e.g., the hardenable composition without filler material, crystalline material, and/or optional additives). One or more organogelators can be included in hardenable compositions of the present invention preferably in an amount of no greater than 10 wt-%, and more preferably in an amount of no greater than 5 wt-%, based on the total weight of the organogelator plus polymerizable component (e.g., the hardenable composition without filler material, crystalline material, and/or optional additives).

Organic Polymerizable Component

The hardenable dental compositions of the present invention can also include an organic polymerizable component, thereby forming polymerizable compositions. Such polymerizable components are selected such that they are compatible with the organogelators.

In certain embodiments, the compositions are photopolymerizable, i.e., the compositions contain a photoinitiator (i.e., a photoinitiator system) that upon irradiation with actinic radiation initiates the polymerization (or hardening) of the composition. Such photopolymerizable compositions can be free radically polymerizable or cationically polymerizable.

In certain embodiments, the compositions are chemically polymerizable. Chemically polymerizable systems (e.g., redox systems) are viable for the flowable and the packable compositions of the present invention, but not particularly desirable for the self-supporting/malleable compositions. This is because chemically polymerizable systems are typically in two parts, which is not necessarily desirable for self-supporting/malleable preformed articles. Chemically polymerizable systems typically include an ethylenically unsaturated compound, which can undergo free-radical or cationic polymerization, for example.

Photopolymerizable Materials

Suitable photopolymerizable compositions may include epoxy resins (which contain cationically active epoxy groups), vinyl ether resins (which contain cationically active vinyl ether groups), ethylenically unsaturated compounds (which contain free radically active unsaturated groups), and combinations thereof. Examples of useful ethylenically unsaturated compounds include acrylic acid esters, methacrylic acid esters, hydroxy-functional acrylic acid esters, hydroxy-functional methacrylic acid esters, and combinations thereof. Also suitable are polymerizable materials that contain both a cationically active functional group and a free radically active functional group in a single compound. Examples include epoxy-functional acrylates, epoxy-functional methacrylates, and combinations thereof.

Photopolymerizable compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include (meth)acrylates (i.e., acrylates and methacrylates) and (meth)acrylamides (i.e., acrylamides and methacrylamides), for example. Specific examples include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, and similar compounds described in U.S. Pat. No. 4,648,843; the bis-acrylates and bis-methacrylates of polyethylene glycols of molecular weight 200-500; copolymerizable mixtures of acrylated monomers such as those in U.S. Pat. No. 4,652,274 (Boettcher et al.); acrylated oligomers such as those of U.S. Pat. No. 4,642,126 (Zador et al.); and vinyl compounds such as styrene, diallyl phthalate, divinyl succinate, divinyl adipate and divinyl phthalate. Suitable ethylenically unsaturated compounds are also available from a wide variety of commercial sources, such as Sigma-Aldrich, St. Louis, Mo. and Rhom and Tech, Inc., Darmstadt, Germany. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.); and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

Photopolymerizable compositions may include compounds having cationically active functional groups such as cationically polymerizable epoxy resins. Such materials include organic compounds having an oxirane ring that is polymerizable by ring opening. These materials include monomeric epoxy compounds and epoxides of the polymeric type and can be aliphatic, cycloaliphatic, aromatic, or heterocyclic. These compounds generally have, on the average, at least 1 polymerizable epoxy group per molecule, preferably at least 1.5 and more preferably at least 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from 58 to 100,000 or more.

Suitable epoxy-containing materials useful in the present invention are listed in U.S. Pat. Nos. 6,187,836 (Oxman et al.) and 6,084,004 (Weinmann et al.).

Blends of various epoxy-containing materials are also contemplated. Examples of such blends include two or more weight average molecular weight distributions of epoxy-containing compounds, such as low molecular weight (below 200), intermediate molecular weight (200 to 10,000), and higher molecular weight (above 10,000). Alternatively or additionally, the epoxy resin may contain a blend of epoxy-containing materials having different chemical natures, such as aliphatic and aromatic, or functionalities, such as polar and non-polar.

Other types of useful materials having cationically active functional groups include vinyl ethers, oxetanes, spiro-orthocarbonates, spiro-orthoesters, and the like.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the CYCLOMER series, such as CYCLOMER M-100, M-101, or A-200 available from Daicel Chemical, Japan, and EBECRYL-3605 available from Radcure Specialties, UCB Chemicals, Atlanta, Ga.

The cationically curable compositions may further include a hydroxyl-containing organic material. Suitable hydroxyl-containing materials may be any organic material having hydroxyl functionality of at least 1, and preferably at least 2. Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight (MW) of the hydroxyl-containing organic material can vary from very low (e.g., 32 grams per mole) to very high (e.g., one million or more grams per mole). Suitable hydroxyl-containing materials can have low molecular weights, i.e., from 32 to 200 grams per mole, intermediate molecular weights, i.e., from 200 to 10,000 grams per mole, or high molecular weights, i.e., above 10,000 grams per mole. As used herein, all molecular weights are weight average molecular weights.

Suitable molecular weights may be less than one million grams per mole, less than 500,000 grams per mole, less than 200,000 grams per mole, less than 100,000 grams per mole, less than 50,000 grams per mole, less than 25,000 grams per mole, less then 15,000 grams per mole, less than 12,500 grams per mole, or less than 10,000 grams per mole.

The hydroxyl-containing materials may be non-aromatic in nature or may contain aromatic functionality. The hydroxyl-containing material may optionally contain heteroatoms in the backbone of the molecule, such as nitrogen, oxygen, sulfur, and the like. The hydroxyl-containing material may, for example, be selected from naturally occurring or synthetically prepared cellulosic materials. The hydroxyl-containing material should be substantially free of groups which may be thermally or photolytically unstable; that is, the material should not decompose or liberate volatile components at temperatures below 100° C. or in the presence of actinic light which may be encountered during the desired photopolymerization conditions for the polymerizable compositions.

Suitable hydroxyl-containing materials useful in the present invention are listed in U.S. Pat. No. 6,187,836 (Oxman et al.).

The amount of hydroxyl-containing organic material used in the polymerizable compositions may vary over broad ranges, depending upon factors such as the compatibility of the hydroxyl-containing material with the cationically and/or free radically polymerizable component, the equivalent weight and functionality of the hydroxyl-containing material, the physical properties desired in the final composition, the desired speed of polymerization, and the like.

Blends of various hydroxyl-containing materials may also be used. Examples of such blends include two or more molecular weight distributions of hydroxyl-containing compounds, such as low molecular weight (below 200), intermediate molecular weight (200 to 10,000), and higher molecular weight (above 10,000). Alternatively, or additionally, the hydroxyl-containing material may contain a blend of hydroxyl-containing materials having different chemical natures, such as aliphatic and aromatic, or functionalities, such as polar and non-polar. As an additional example, one may use mixtures of two or more poly-functional hydroxy materials or one or more monofunctional hydroxy materials with poly-functional hydroxy materials.

The polymerizable material(s) may also contain hydroxyl groups and free radically active functional groups in a single molecule. Examples of such materials include hydroxyalkylacrylates and hydroxyalkylmethacrylates such as hydroxyethylacrylate, hydroxyethylmethacrylate; glycerol mono- or di-(meth)acrylate; trimethylolpropane mono- or di-(meth)acrylate, pentaerythritol mono-, di-, or tri-(meth)acrylate; sorbitol mono-, di-, tri-, tetra-, or penta-(meth)acrylate; and 2,2-bis[4-(2-hydroxy-3 methacryloxypropoxy)phenyl]propane.

The polymerizable material(s) may also contain hydroxyl groups and cationically active functional groups in a single molecule. An example is a single molecule that includes both hydroxyl groups and epoxy groups.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, and diphenyliodonium tetrafluoroborate. Preferred photosensitizers are monoketones and diketones that absorb some light within a range of 450 nm to 520 nm (preferably, 450 nm to 500 nm). More preferred compounds are alpha diketones that have some light absorption within a range of 450 nm to 520 nm (even more preferably, 450 nm to 500 nm). Preferred compounds are camphorquinone, benzil, furil, 3,3,6,6-tetramethylcyclohexanedione, phenanthraquinone and other cyclic alpha diketones. Most preferred is camphorquinone. Preferred electron donor compounds include substituted amines, e.g., ethyl dimethylaminobenzoate.

Suitable photoinitiators for polymerizing cationically photopolymerizable compositions include binary and tertiary systems. Typical tertiary photoinitiators include an iodonium salt, a photosensitizer, and an electron donor compound as described in U.S. Pat. Nos. 5,856,373 (Kaisaki et al.), 6,084,004 (Weinmann et al.), 6,187,833 (Oxman et al.), 6,187,836 (Oxman et al.), and 6,765,036 (Dede et al). Preferred iodonium salts, photosensitizers, and electron donor compounds are for photoinitiator systems for polymerizing free radically photopolymerizable compositions.

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. Nos. 4,298,738 (Lechtken et al.), 4,324,744 (Lechtken et al.), 4,385,109 (Lechtken et al.), 4,710,523 (Lechtken et al.), 4,737,593 (Ellrich et al.), 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 percent by weight (wt-%) to 5.0 wt-%, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 wt-% to 5.0 wt-%, based on the total weight of the composition.

Chemically Polymerizable Materials

For chemically polymerizable compositions, typically, free radical polymerizable compositions, an initiation system can be selected from systems that initiate polymerization via radiation, heat, or redox/auto-cure chemical reaction.

The hardenable resins of the present invention can include redox cure systems that include a polymerizable component (e.g., an ethylenically unsaturated polymerizable component) and redox systems that include an oxidizing agent and a reducing agent. Suitable polymerizable components and redox systems that are useful in the present invention are described in U.S. Pat. Nos. 6,624,211 (Karim et al.) and 6,964,985 (Karim et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system to permit ready dissolution in (and discourage separation from) the other components of the polymerizable composition.

Useful reducing agents include, for example, ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and combinations thereof. Preferably, the reducing agent is an amine.

Suitable oxidizing agents will also be familiar to those skilled in the art, and include, for example, persulfuric acid and salts thereof, such as sodium, potassium, ammonium, cesium, and alkyl ammonium salts. Additional oxidizing agents include, for example, peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and combinations thereof.

It may be desirable to use more than one oxidizing agent or more than one reducing agent. Small quantities of transition metal compounds may also be added to accelerate the rate of redox cure.

The reducing and oxidizing agents are present in amounts sufficient to permit an adequate free-radical reaction rate. This can be evaluated by combining all of the ingredients of the hardenable composition except for the filler, and observing whether or not a hardened mass is obtained.

Preferably, the reducing agent is present in an amount of at least 0.01% by weight, and more preferably at least 0.1 wt-%, based on the total weight of the components of the hardenable composition. Preferably, the reducing agent is present in an amount of no greater than 10 wt-%, and more preferably no greater than 5 wt-%, based on the total weight of the components of the hardenable composition.

Preferably, the oxidizing agent is present in an amount of at least 0.01 wt-%, and more preferably at least 0.10 wt-%, based on the total weight of the components of the hardenable composition. Preferably, the oxidizing agent is present in an amount of no greater than 10 wt-%, and more preferably no greater than 5 wt-%, based on the total weight of the components of the hardenable composition.

The reducing or oxidizing agents can be microencapsulated. This will generally enhance shelf stability of the hardenable composition, and if necessary permit packaging the reducing and oxidizing agents together. For example, through appropriate selection of an encapsulant, the oxidizing and reducing agents can be combined with an acid-functional component and optional filler and kept in a storage-stable state.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. and at most 150° C. under normal conditions or at elevated pressure. This procedure is preferred for initiating polymerization of materials occurring outside of the oral environment.

Yet another alternative class of initiators capable of initiating polymerization of free radically active functional groups in the hardenable resin are those that include free radical-generating thermal initiators. Examples include peroxides (e.g., benzoyl peroxide and lauryl peroxide) and azo compounds (e.g., 2,2-azobis-isobutyronitrile (AIBN)).

Crystalline Material

In certain embodiments, the hardenable composition includes a crystalline material to impart a noncovalent three-dimensional structure for maintaining an initial preformed shape. This crystalline material may or may not have a reactive group capable of polymerizing (also including crosslinking). Preferably, the crystalline material is polymerizable. Preferably, the crystalline material is polymeric (including oligomeric). More preferably, the crystalline material is a polymerizable polymeric material.

By "crystalline" it is meant that the material displays a crystalline melting point at 20° C. or above when measured in the composition by differential scanning calorimetry (DSC). The peak temperature of the observed endotherm is taken as the crystalline melting point.

The crystalline melting point is preferably less than 100° C., more preferably less than 90° C., and even more preferably less than 80° C.

The crystalline phase may include multiple lattices in which the material assumes a conformation in which there is an ordered structure in adjacent chemical moieties of which the material is composed. The packing arrangement within the lattice may be highly regular in both its chemical and structural aspects.

A crystalline material may be in a "semicrystalline state" in that long segments of polymer chains appear in both amorphous and crystalline states or phases at 20° C. or above. The amorphous phase may be considered to be a randomly tangled arrangement of polymer chains. The X-ray diffraction pattern of an amorphous polymer is a diffuse halo, which is indicative of very low or no ordering of the polymer structure. Amorphous polymers show softening behavior at the glass transition temperature, but not melting behavior. A material in a semicrystalline state shows characteristic melting points, above which the crystalline lattices become disordered. The X-ray diffraction pattern of such "semicrystalline" materials generally may be distinguished by either concentric rings or a symmetrical array of spots, which are indicative of the nature of the crystalline order. Thus, herein, a "crystalline" component encompasses semicrystalline materials.

The crystalline material includes at least one material that crystallizes, preferably above room temperature. Such crystallinity, that may be provided by the aggregation of crystallizable moieties present in the component (e.g., when the component is a polymer, in the backbone (i.e., main chain) or pendant substituents (i.e., side chains) of the component), can be determined by well known crystallographic, calorimetric, or dynamic/mechanical methods. For the purposes of the present invention, this component imparts to the hardenable composition at least one melting temperature ($T_m$) as measured experimentally (for example by DSC) of greater than 20° C. Preferably, this component imparts a $T_m$ to the hardenable composition of 30° C.-100° C. If more than one crystalline material is used in the hardenable composition, more than one distinct melting point may be seen.

The number average molecular weight of the crystalline material may vary over a broad range. Preferably, the molecular weight is less than 10,000 grams per mole (g/mol), and preferably no greater than 5000 g/mol. Preferably, the molecular weight is at least 150 g/mol, and more preferably at least 400 g/mol. The crystalline monomers suitable for use in the resin system include monomers containing urethane, ether, ester, amide, or imide groups, or combinations thereof. Preferred crystalline monomers contain reactive groups capable of polymerizing and/or crosslinking. Especially preferred are monomers with a reactive functionality greater than one.

The crystalline polymers (including oligomers) suitable for use in the resin system can have crystalline main chain (i.e., linear) or pendant (i.e., side chain) segments. Preferred materials also contain reactive groups capable of polymerizing and/or crosslinking. Especially preferred are crystalline oligomers or prepolymers with a reactive functionality of at least two.

Examples of suitable crystalline materials having crystallizable main chain or backbone segments include, but are not limited to, polyesters (including polycaprolactones), polyethers, polythioethers, polyarylalkylenes, polysilanes, polyamides, polyolefins (preferably, formed from lower, e.g., $C_2$-$C_3$, olefins), polyurethanes, and combinations thereof.

Preferred crystalline materials are saturated, linear, aliphatic polyester polyols (particularly diols) containing primary hydroxyl end groups. Examples of commercially available materials useful as the crystalline material in the resin systems of the invention include some resins available under the trade designation LEXOREZ from Inolex Chemical Co., Philadelphia, Pa. Examples of other polyester polyols useful in the compositions of the invention are those available under the trade designation RUCOFLEX from Ruco Polymer Corp., Hicksville, N.Y. Examples of polycaprolactones that are useful in the invention include those available under the trade designations TONE 0230, TONE 0240, and TONE 0260 from Dow Chemical Co., Midland, Mich., and those available under the trade designation CAPA from Solvay Co., Warrington, Cheshire, UK. Especially preferred materials are saturated, linear, aliphatic polyester polyols that are chemically modified or reacted (e.g., through primary hydroxyl end groups) to introduce polymerizable, unsaturated functional groups, e.g., polycaprolactone diol reacted with 2-isocyanatoethyl methacrylate, methacryloyl chloride, or methacrylic anhydride.

The crystalline materials may also have a dendritic, hyperbranched, or star-shaped structure, for example, with varying degrees of branching. Dendritic polymers are polyfunctional compounds and include any of the known dendritic architectures including dendrimers, regular dendrons, dendrigrafts, and hyperbranched polymers. Dendritic polymers are polymers with densely branched structures having a large number of end reactive groups. A dendritic polymer includes several layers or generations of repeating units which all contain one or more branch points. Dendritic polymers, including dendrimers and hyperbranched polymers, can be prepared by condensation, addition, or ionic reactions of monomeric units having at least two different types of reactive groups.

Dendritic polymers are comprised of a plurality of dendrons that emanate from a common core, which core usually comprises a group of atoms. Dendritic polymers generally consist of peripheral surface groups, interior branch junctures having branching functionalities greater than or equal to two, and divalent connectors that covalently connect neighboring branching junctures.

Dendrons and dendrimers may be ideal or non-ideal, i.e., imperfect or defective. Imperfections are normally a consequence of either incomplete chemical reactions or unavoidable competing side reactions.

Hyperbranched polymers are dendritic polymers that contain high levels of non-ideal irregular branching arrays as compared with the more nearly perfect regular structure dendrimers. Specifically, hyperbranched polymers contain a relatively high number of irregular branching arrays in which not every repeat unit contains a branch juncture. Consequently, hyperbranched polymers may be viewed as intermediate between linear polymers and dendrimers. Yet they are dendritic because of their relatively high branch-juncture content per individual macromolecule.

Star-shaped polymers typically consist of polymer chains emanating from a central core.

The preparation and characterization of dendrimers, dendrons, dendrigrafts, hyperbranched polymers, and star-shaped are well known. Examples of dendrimers and dendrons, and methods of synthesizing the same are set forth in U.S. Pat. Nos. 4,507,466 (Tomalia et al.), 4,558,120 (Tomalia et al.), 4,568,737 (Tomalia et al.), 4,587,329 (Tomalia et al.), 4,631,337 (Tomalia et al.), 4,694,064 (Tomalia et al.), 4,713,975 (Tomalia et al.), 4,737,550 (Tomalia), 4,871,779 (Killat et al.), and 4,857,599 (Tomalia et al.). Examples of hyperbranched polymers and methods of preparing the same are set forth, for example, in U.S. Pat. No. 5,418,301 (Hult et al.). Some dendritic polymers are also commercially available. For example, 3- and 5-generation hyperbranched polyester polyols may be obtained from Perstorp Polyols, Inc., Toledo, Ohio. Examples of star polymers and methods of preparing the same are set forth, for example, in U.S. Pat. Nos. 5,830,986 (Merrill et al.), 5,859,148 (Borggreve et al.), 5,919,870 (Letchford et al.), and 6,252,014 (Knauss).

The dendritic polymers useful in this invention may include any number of generations, preferably three to five generations.

Generally, any of the known dendritic polymers having crystalline peripheral groups, or having peripheral groups that can be reacted with another compound to crystalline peripheral groups are suitable for use in the resin system in the compositions of this invention. Examples of suitable dendritic polymers include polyethers, polyesters, polythioether, polyarylalkylenes, polysilanes, polyamides, polyurethanes, and any other condensation polymers.

Examples of suitable crystalline polymeric materials having crystallizable pendant moieties (i.e., side chains) include, but are not limited to polymeric materials prepared by the polymerization of monomers containing the pendant (side chain) crystallizable moieties or by the introduction of pendant crystallizable moieties by chemical modification of a polyacrylate, polymethacrylate, polyacrylamide, polymethacrylamide, polyvinyl ester, or poly-alpha-olefin polymers or copolymers. As long as the crystalline oligomer or polymer has a crystalline melting point, it can include non-crystallizable monomers. The preparation and morphology/conformational properties that determine the crystalline character of such side chain crystallizable or "comb-like" polymers are reviewed by Plate and Shibaev, "Comb-Like Polymers. Structure and Properties," *Journal of Polymer Science, Macromolecular Reviews*, 8, 117-253 (1974).

Another crystalline material includes compounds of the formula (Formula LXXIV):

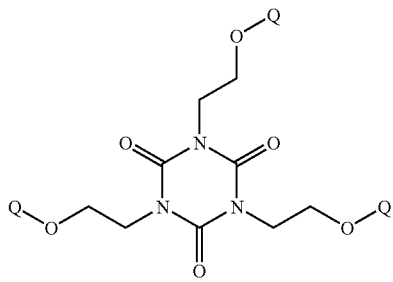

LXXIV wherein each Q independently includes polyester segments, polyamide segments, polyurethane segments, polyether segments, or combinations thereof. Preferably, each Q independently includes poly(caprolactone) segments. More preferably, such crystalline compounds include polymerizable groups, such as epoxy, acid, alcohol, and ethylenically unsaturated reactive sites. Particularly preferred such materials include unsaturated polymerizable groups, such as methacrylic, acrylic, vinyl, and styryl groups.

Filler Material

The hardenable compositions of the present invention can also contain fillers. Fillers may be selected from one or more of a wide variety of materials suitable for incorporation in compositions used for dental applications, such as fillers currently used in dental restorative compositions, and the like.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

The filler is preferably finely divided. The filler can have a unimodal or polymodal (e.g., bimodal) particle size distribution. Preferred particulate filler has an average particle size (preferably, diameter) of less than 10 micrometers (i.e., microns), which includes micron-size and nanoscopic particles.

Micron-size particles are very effective for improving post-cure wear properties. Preferred micron-size particulate filler has an average particle size of at least 0.2 micron up to 1 micron.

Nanoscopic fillers are commonly used as viscosity and thixotropy modifiers. Due to their small size, high surface area, and associated hydrogen bonding, these materials may assemble into aggregated networks. Materials of this type ("nanoscopic" materials) have average particle sizes (i.e., the largest dimension, e.g., diameter) of less than 200 nanometers (nm). Preferably, the nanoscopic particulate material has an average particle size of at least 2 nanometers (nm), and more preferably at least 7 nm. Preferably, the nanoscopic particulate material has an average particle size of no greater than 50 nm, and more preferably no greater than 20 nm in size. The average surface area of such a filler is preferably at least 20 square meters per gram ($m^2/g$), more preferably, at least 50 $m^2/g$, and most preferably, at least 100 $m^2/g$. If the nanoscopic filler aggregates (i.e., forms an aggregated network as occurs in fumed silica), the particle sizes referred to above are primary particle sizes (i.e., particle sizes of the unaggregated material).

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler is also substantially insoluble in water.

Examples of suitable inorganic fillers are naturally occurring or synthetic materials including, but not limited to: quartz; nitrides (e.g., silicon nitride); glasses derived from, for example, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150," and "200" silicas from Degussa Corp., Akron, Ohio and CAB-O-SIL M5 silica from Cabot Corp., Tuscola, Ill.). Fumed silica is a preferred compound for imparting self-supporting character, due to its low cost, commercial availability, and wide range of available surface character.

Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

Other suitable fillers are disclosed in U.S. Pat. Nos. 6,387,981 (Zhang et al.) and 6,730,156 (Windisch et al.), as well as International Publication Nos. WO 01/30304 (Wu et al.), WO 01/30305 (Zhang et al.), WO 01/30306 (Windisch et al.), and WO 01/30307 (Zhang et al.). Other suitable fillers are described in references cited within these publications.

U.S. Pat. No. 6,306,926 (Bretscher et al.) discloses a number of radiopacifying fillers that can be used in both free radically polymerizable compositions, cationically polymerizable compositions, and hybrid compositions featuring both free radically and cationically polymerizable components. They are particularly advantageous for use in cationically polymerizable compositions.

One such filler is a melt-derived filler that includes 5-25% by weight aluminum oxide, 10-35% by weight boron oxide, 15-50% by weight lanthanum oxide, and 20-50% by weight silicon oxide. Another filler is a melt-derived filler that includes 10-30% by weight aluminum oxide, 10-40% by weight boron oxide, 20-50% by weight silicon oxide, and 15-40% by weight tantalum oxide. A third filler is a melt-derived filler that includes 5-30% by weight aluminum oxide, 5-40% by weight boron oxide, 0-15% by weight lanthanum oxide, 25-55% by weight silicon oxide, and 10-40% by weight zinc oxide. A fourth filler is a melt-derived filler that includes 15-30% by weight aluminum oxide, 15-30% by weight boron oxide, 20-50% by weight silicon oxide, and 15-40% by weight ytterbium oxide. A fifth filler is in the form of non-vitreous microparticles prepared by a sol-gel method in which an aqueous or organic dispersion or sol of amorphous silicon oxide is mixed with an aqueous or organic dispersion, sol, or solution of a radiopacifying metal oxide, or precursor organic or compound. A sixth filler is in the form of non-vitreous microparticles prepared by a sol-gel method in which an aqueous or organic dispersion or sol of amorphous silicon oxide is mixed with an aqueous or organic dispersion, sol, or solution of a radiopacifying metal oxide, or precursor organic or inorganic compound.

Preferably, the total amount of filler is 50 wt-% or more, more preferably, 60 wt-% or more, and most preferably, 70 wt-% or more, based on the total weight of the composition. Preferably, the total amount of filler system is no more than 95 wt-%, and more preferably, no more than 80 wt-%, based on the total weight of the composition. Significantly, such high filler loadings with the resin systems of the present invention is unexpected, particularly in providing a malleable composition.

Optional Additives

If desired, the hardenable composition of the invention can contain additives such as pigments, inhibitors, accelerators, viscosity modifiers, surfactants, and other ingredients that will be apparent to those skilled in the art. Additionally, medicaments can be optionally added to the dental compositions. Examples include anti-inflammatory agents, antimicrobial agents, whitening agents, and the like, of the type often used in dental compositions. The selection and amount of any one such additive can be selected by one of skill in the art to accomplish the desired result without undue experimentation.

Preparation and Use of the Compositions

The hardenable dental compositions of the present invention can be prepared by combining an organogelator with a polymerizable component using conventional mixing techniques. The resulting composition may optionally contain crystalline materials, fillers, and other additives as described herein. In use, the compositions may contain a photoinitiator and be hardened by photoinitiation, or may be hardened by chemical polymerization, such as in redox systems, in which the compositions contain a free-radical initiator. Combinations of such cure systems are also possible.

The hardenable compositions of the invention can be supplied in a variety of forms including one-part systems and multi-part systems, e.g., two-part powder/liquid, paste/liquid, and paste/paste systems. Other forms employing multi-part combinations (i.e., combinations of two or more parts), each of which is in the form of a powder, liquid, gel, or paste are also possible. In a redox multi-part system, one part typically contains the oxidizing agent and another part typically contains the reducing agent.

The components of the hardenable composition can be included in a kit, where the contents of the composition are packaged, as described below, to allow for storage of the components until they are needed.

When used as a dental composition, the components of the hardenable compositions can be mixed and clinically applied using conventional techniques. A curing light is generally required for the initiation of photopolymerizable compositions. The compositions can be in the form of composites or restoratives, for example, that adhere very well to dentin and/or enamel. Optionally, a primer layer can be used on the tooth tissue on which the hardenable composition is used.

The compositions of the invention are particularly well adapted for use in the form of a wide variety of dental restoratives, which include composites that are polymerized after being disposed adjacent to a tooth, such as filling materials. They can also be used in prostheses as well as in dental impression trays, orthodontic appliances (e.g., retainers, night guards), orthodontic adhesives, and the like. They can be used in crowns, bridges, veneers, inlays, onlays, implants, dentures, artificial teeth, tooth facsimiles, splints, maxillofacial prostheses, and other customized structures, which are typically shaped before being disposed on or adjacent to a tooth. Such preformed articles can be ground or otherwise formed into a custom-fitted shape by the dentist or other user. Compositions of the present invention are particularly useful in dental restoratives, particularly crowns (temporary, intermediate/interim, or permanent).

Certain embodiments of the compositions of the present invention can be shaped (e.g., molded) into a variety of forms like three-dimensional shapes, preformed sheets, arch-shaped trays, ropes, buttons, woven, or non-woven webs, and the like. The composition can be shaped (to form a first shape) in a variety of ways including, for example, extruding, injection molding, compression molding, thermoforming, vacuum forming, pressing, calendering, and web processing using rollers. Typically, a semi-finished shape is formed using a mold with a positive and negative impression.

The shaped articles can be sold individually or in multiple units, preferably packaged in a way that protects them from heat and/or light that can activate the initiator system contained in the composition.

Generally, a preformed article of appropriate size and shape (the first shape) is selected and custom shaped (to a second shape) at a temperature of 15° C. to 38° C. (preferably, 20° C. to 38° C., which encompasses typical room temperatures and body temperatures, and more preferably, at room temperature). This shaping can be done by a variety of methods including applying pressure with fingers or an instrument of choice (e.g., hand operation of dental composite instrument), trimming, cutting, sculpting, grinding, etc. Once the desired custom (second) shape has been achieved, the article is hardened (e.g., cured) by exposing it to heat/radiation to cause activation of the initiator system. This can be done either in a single step, or in multiple steps with successive steps of custom shaping being done in-between. One or more of these steps can be carried out in an oxygen-free inert atmosphere or in vacuum. After the final shaping and hardening steps, the hardened article can be further modified in shape by grinding, trimming, etc., if desired. Once the final custom (second) shape of the article has been obtained, it can be polished, painted, or otherwise surface treated, if required for the intended application. Preferably, the final custom shaped articles prepared from the compositions of the present invention do not need an additional veneering material (e.g., a second material that provides a desired appearance or property). The intended application may require mounting, bonding, or otherwise attaching the custom shaped cured article to a second object adhesively, mechanically, or by combination of both.

For the preparation of a provisional dental crown, an appropriate shape and size of a preformed crown is selected and the preformed crown is seated on the prepared tooth to determine the extent of trimming and shaping required, optionally making marks on the crown. The preformed crown is removed from the mouth, the required shape and size adjustments are made by cutting, trimming, shaping, etc., and then re-seated on the tooth preparation where additional shape adjustments are made to provide optimum custom fit, including gingival, lateral, and occlusal fit. The preformed and reshaped crown can then be hardened, for example by exposing it to a dental curing light for a few seconds, if desired, while in the mouth, and then removing it carefully from the mouth and exposing it for final cure to a curing light in a cure chamber, optionally in combination with heat. Alternatively, the crown can also be completely cured in the mouth by irradiating it with a dental curing light. Final adjustments are made by grinding, trimming, etc., if required, and the finished crown is polished and cleaned. The finished crown can then be cemented as is or lined with a suitable resin material prior to placement in the mouth.

The hardenable, self-supporting structures (e.g., dental products) of this invention can be prepackaged either individually or as an ensemble. Such packaging material should protect these products from conditions that would activate the initiator system and thus cause premature hardening, e.g., such as could result from exposure to light in the case of a photoinitiator. In addition, the packaging material optionally conforms to the surfaces of the product, thereby providing additional mechanical strength in order to resist damage during shipping. For example, a preformed crown or tray could be packaged in a layer of polyolefin on all sides. The polyolefin provides a mechanical structure and can be sealed to avoid contact with water. If the polyolefin were filled with an appropriate dye or pigment, e.g., carbon black, incident light would be absorbed before it could reach the enclosed product. If such a packaging layer is somewhat rigid, and if the packaging material is shaped similar to the preformed article of the invention, then the packaging could enhance the dimensional stability of the preformed product during shipment and storage. In certain cases, the packaging may thus form an integral part of the product system.

The invention is also useful in a number of preformed orthodontic appliances. For example, the hardenable composition may be fabricated into a custom appliance such as a lingual retainer, a space retainer, a hook, a button, or a splint. As another example, the composition may be used to make a portion of an appliance, such as a custom base for an orthodontic bracket that is adapted to closely fit the curvature of a patient's tooth, or an orthodontic bracket with tiewings that are oriented at a particular angle to avoid contact with adjacent structure in the oral cavity. The composition also may be used to make a tooth facsimile that is bonded to an archwire to hide open spaces between teeth during the course of treatment. Furthermore, the composition may be used to bond groups of adjacent teeth together to establish strong anchorage for other orthodontic appliances. Additionally, the composition may be formed into a droplet of material that is bonded to an archwire at a certain location to prevent sliding movement of the archwire or to prevent movement of another appliance. When used in orthodontic applications, the composition of the invention can be shaped to a desired configuration in vivo and then hardened in place in the oral cavity. Alternatively, the composition can be shaped to a desired configuration outside of the oral cavity using, if desired, a model of the patient's tooth structure. When the composition is shaped outside of the oral cavity, the composition is preferably hardened before placement in the oral cavity.

The invention can also be useful as orthodontic adhesives that can be applied to orthodontic appliances (including, but not limited to, orthodontic brackets, buccal tubes, lingual tubes, and cleats) to bond the appliances to teeth. Orthodontic adhesives may be applied to orthodontic brackets by the orthodontist or by the manufacturer of the brackets. Certain embodiments of the invention may be particularly useful as orthodontic adhesives that are supplied on adhesive pre-coated orthodontic brackets, such as those described in U.S. Pat. Nos. 4,978,007, 5,015,180, and 5,328,363. Adhesive pre-coated brackets include brackets upon which the manufacturer has applied a precise quantity of adhesive such as a photocurable adhesive. The adhesive can be protected from light, evaporation, oxidation, contamination, humidity, and sublimation by a release liner or outer package until use. When it is desired to mount a bracket on a tooth, the bracket is released from a release liner (if provided) and then, with the adhesive, is simply placed directly on the tooth. The adhesive can then be cured, e.g., photocured. An advantage of pre-coated brackets is that the manufacturer can control the quantity of adhesive placed on each bracket. As a result, there is sufficient adhesive to substantially fill the space between the bracket base and the tooth and yet there is not an inordinate amount of adhesive such that excessive cleanup around the perimeter of the bracket base would be necessary.

Many orthodontists prefer to use certain adhesives that are less viscous (i.e., more fluid) than other adhesives. However, some adhesives with a relatively low viscosity have been found to occasionally distort in shape or remain on the release liner as the bracket is released from the liner, such that the orthodontist may need to pause to re-shape the adhesive or apply additional adhesive to the bracket base. Certain orthodontic adhesives having a relatively high viscosity may release in a satisfactory manner from a release coating when newly mixed or newly applied to brackets. However, adhesive pre-coated brackets may not be bonded to a patient's teeth for some time. Many conventional adhesives have relatively low molecular weight components that tend to volatilize over a period of time to such a degree that the adhesive becomes too stiff, in general, for satisfactory use for precoated brackets. On the other hand, an adhesive made with relatively high molecular weight components may have a low volatility but may be too stiff to provide sufficient adhesive strength after curing. Generally, orthodontic adhesives of the present invention have rheological properties (e.g., viscosity) such that they can be easily applied to orthodontic appliances and can maintain their rheological properties in a range that is suitable for use. They can also be applied to a bracket in such a way that they remain on the bracket without slumping due to gravity during application.

The present invention provides methods of preparing dental products from the hardenable dental compositions of the present invention. For example, in certain embodiments, the hardenable dental composition is formed into a hardenable dental product, wherein the hardenable dental composition of the hardenable dental product is a self-supporting structure having a first shape and sufficient malleability to be formed into a second shape at a temperature of 15° C. to 38° C.

In certain embodiments, the present invention also provides methods of preparing dental products wherein the hardenable dental composition of the present invention is applied to a dental product. In certain embodiments, the hardenable dental composition is flowable. In certain embodiments, the hardenable dental composition is an orthodontic adhesive. In certain embodiments, the dental product is an orthodontic appliance.

The present invention also provides methods of using dental products that include the hardenable dental compositions of the present invention. In one embodiment, the method includes: providing a dental product comprising a hardenable dental composition of the present invention, wherein the hardenable dental composition has a self-supporting structure having a first shape and sufficient malleability to be formed into a second shape at a temperature of 15° C. to 38° C.; placing the dental product on a tooth surface in the mouth of a subject or on a model of a tooth surface; customizing the shape of the dental product in the mouth of a subject or on a model of a tooth surface; and hardening the hardenable dental composition of the dental product.

In one embodiment, the method of using a hardenable dental composition includes: providing a hardenable dental composition of the present invention, wherein the hardenable dental composition is flowable or packable; placing the dental product on a tooth surface in the mouth of a subject, wherein the tooth surface is optionally coated with a dental adhesive; and hardening the hardenable dental composition.

In one embodiment, the method of using a hardenable dental composition includes: providing a hardenable dental composition of the present invention, wherein the hardenable dental composition is a hardenable orthodontic adhesive; placing the hardenable orthodontic adhesive on an orthodontic bracket prior to the bracket contacting a tooth surface, wherein the tooth surface is optionally coated with a dental adhesive; and hardening the hardenable orthodontic adhesive.

In one embodiment, the method of using a hardenable dental composition includes: providing a dental product comprising an orthodontic bracket having coated thereon a hardenable dental composition of the present invention, wherein the hardenable dental composition is a hardenable orthodontic adhesive; placing the bracket on a tooth surface, wherein the tooth surface is optionally coated with a dental adhesive; and hardening the hardenable orthodontic adhesive.

EXEMPLARY EMBODIMENTS

Embodiment 1

A hardenable dental composition comprising: an organic polymerizable component; an organogelator; and a crystalline material.

Embodiment 2

A hardenable dental composition comprising: an organic polymerizable component; an organogelator; and 60% or more filler material.

Embodiment 3

A hardenable dental composition comprising: an organic polymerizable component; an organogelator; and filler material comprising nanoscopic particles.

Embodiment 4

A hardenable dental composition comprising: an organic polymerizable component; and a polymerizable organogelator.

Embodiment 5

The hardenable dental composition of embodiment 1 wherein the crystalline material comprises a reactive group.

Embodiment 6

The composition of embodiment 1 wherein the crystalline material comprises polyesters, polyethers, polyolefins, polythioethers, polyarylalkylenes, polysilanes, polyamides, polyurethanes, or combinations thereof.

Embodiment 7

The composition of embodiment 6 wherein the crystalline material comprises saturated, linear, aliphatic polyester polyols containing primary hydroxyl end groups.

Embodiment 8

The hardenable dental composition of any one of embodiments 1 or 5 through 7 further comprising a filler material.

Embodiment 9

The hardenable dental composition of embodiment 3 or embodiment 8 wherein the filler material is present in an amount of 60% or more.

Embodiment 10

The hardenable dental composition of embodiment 8 wherein the filler material comprises nanoscopic particles.

Embodiment 11

The hardenable dental composition of embodiment 3 or embodiment 10 wherein the nanoscopic particles form aggregated networks.

Embodiment 12

The hardenable dental composition of embodiment 11 wherein the nanoscopic particles comprise fumed silica.

Embodiment 13

The hardenable dental composition of any one of embodiment 1 through 3, or embodiments 5 through 12 wherein the organogelator is polymerizable.

Embodiment 14

The hardenable dental composition of any one of embodiment 1 through 13 wherein the composition is photopolymerizable.

Embodiment 15

The hardenable dental composition of embodiment 14 wherein the polymerizable component is selected from the group consisting of epoxy resins, vinyl ether resins, ethylenically unsaturated compounds, and combinations thereof.

Embodiment 16

The hardenable dental composition of any one of embodiments 1 through 13 wherein the composition is chemically polymerizable.

Embodiment 17

The hardenable dental composition of embodiment 16 wherein the chemically polymerizable component comprises an ethylenically unsaturated compound.

Embodiment 18

The hardenable dental composition of any one of embodiments 1 through 17 wherein the organogelator is a urea-type organogelator.

Embodiment 19

The hardenable dental composition of any one of embodiments 1 through 17 wherein the organogelator is of the general formula:

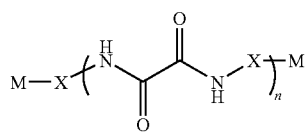

wherein each M is independently hydrogen or a polymerizable group, each X is independently an alkylene group, cycloalkylene group, arylene group, arenylene group, or combinations thereof, and n is 1 to 3.

Embodiment 20

The hardenable dental composition of embodiment 19 wherein the organogelator is selected from the group consisting of compounds of the formulas:

Embodiment 21

The hardenable dental composition of any one of embodiments 1 through 17 wherein the organogelator is an amino sugar organogelator.

Embodiment 22

The hardenable dental composition of embodiment 21 wherein the organogelator is an amino sugar organogelator of the general formula LXXV, or a pharmaceutically acceptable salt thereof:

LXXV wherein: $R^1$ and $R^2$ are independently selected from the group consisting of a hydrogen atom, an alkyl group, $C(O)R^3$, and $SO_2R^4$; $R^3$ and $R^4$ are independently selected from the group

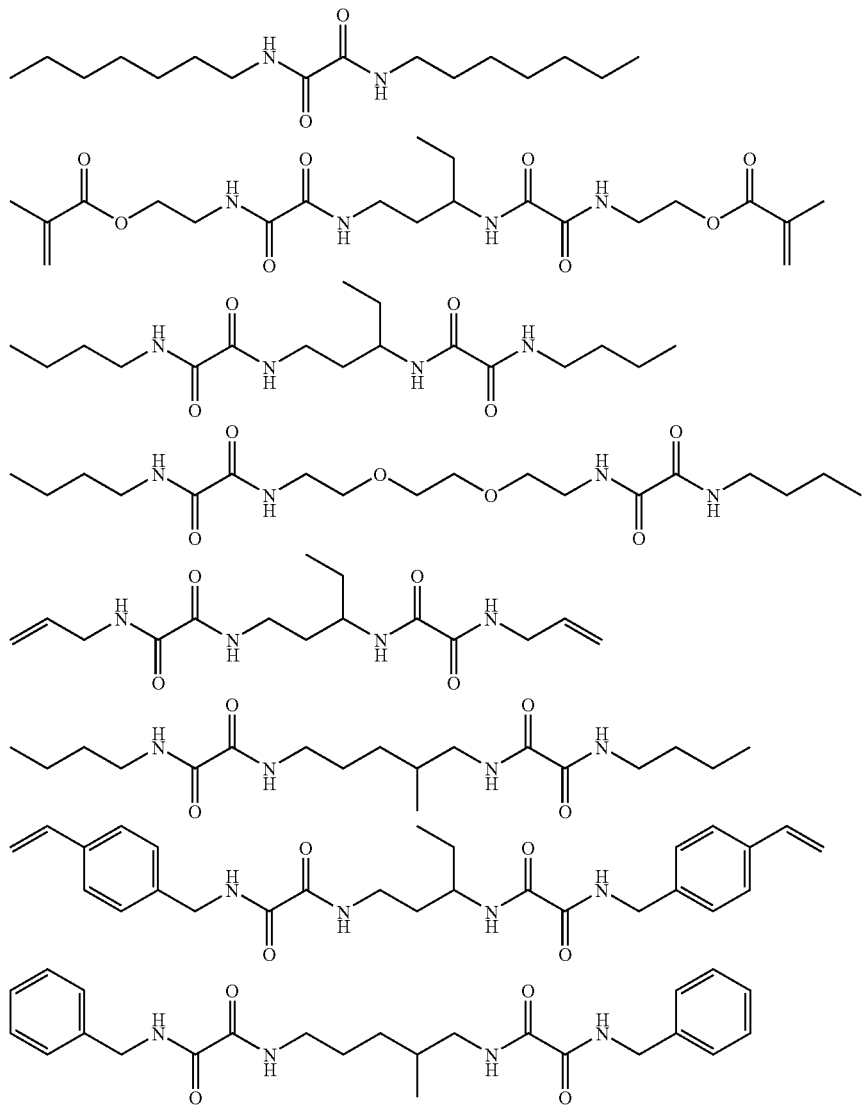

and mixtures thereof.

consisting of an alkyl group, an aryl group, and an aralkyl group; and n is an integer from about 2 to about 5.

Embodiment 23

The hardenable dental composition of embodiment 22 wherein the organogelator is selected from the group consisting of compounds of the formulas:

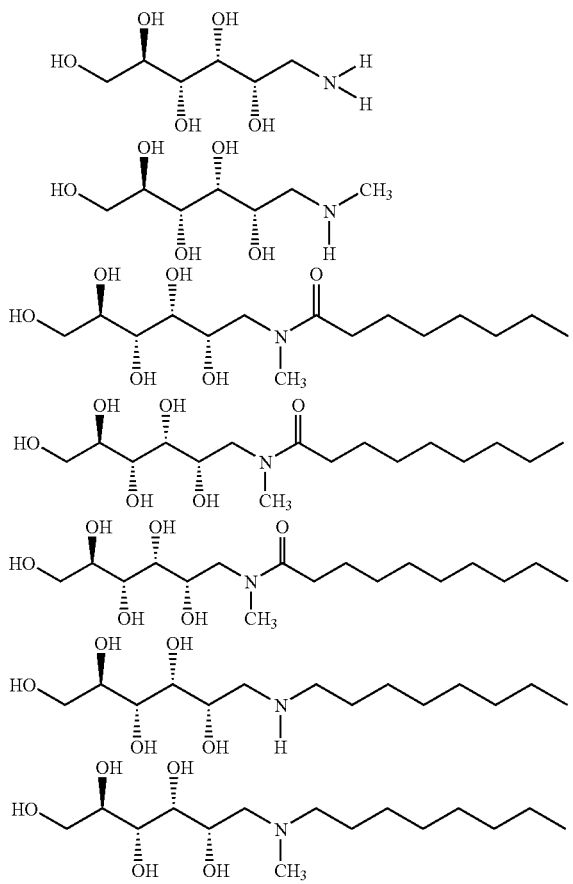

and mixtures thereof.

Embodiment 24

The hardenable dental composition of embodiment 21 wherein the organogelator is an amino sugar organogelator of the general formula LXXXIII, or a pharmaceutically acceptable salt thereof:

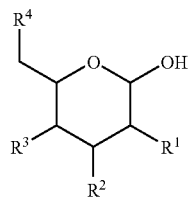

LXXXIII wherein: $R^1$, $R^2$, and $R^3$ are independently selected from the group consisting of OH and $NR^5R^6$; $R^4$ is selected from the group consisting of OH, $OP(O)(OH)_2$, $OSO_3H$, and $NR^5R^6$; $R^5$ and $R^6$ are independently selected from the group consisting of a hydrogen atom, an alkyl group, $C(O)R^7$, and $SO_2R^8$; and $R^7$ and $R^8$ are independently selected from the group consisting of an alkyl group, an aryl group, or an aralkyl group; provided that at least one of $R^1$, $R^2$, $R^3$, and $R^4$ is $NR^5R^6$.

Embodiment 25

The hardenable dental composition of embodiment 24 wherein the organogelator is selected from the group consisting of compounds of the formulas:

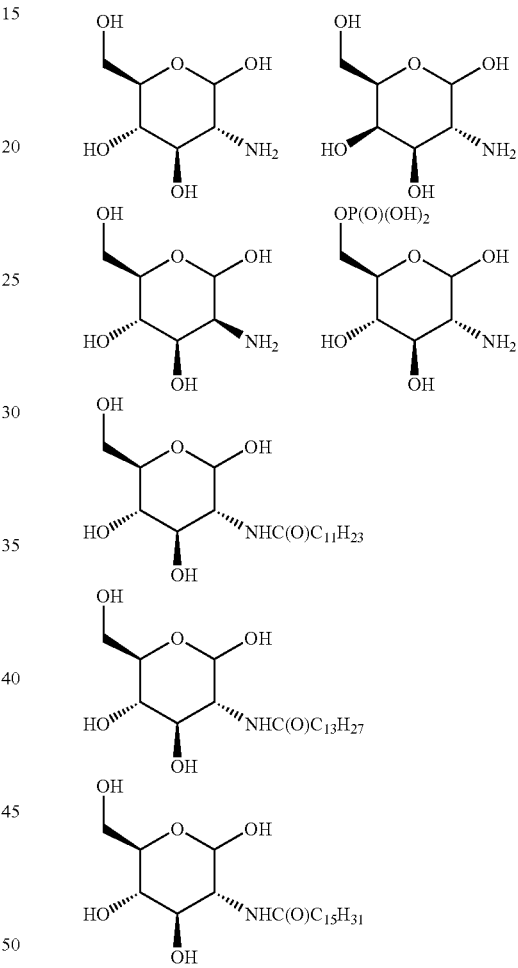

and mixtures thereof.

Embodiment 26

The hardenable dental composition of any one of embodiments 1 through 25 which is suitable for forming a dental restorative.

Embodiment 27

The hardenable dental composition of any one of embodiments 1 through 25 which is in the form of a hardenable self-supporting structure having a first shape and sufficient malleability to be formed into a second shape at a temperature of 15° C. to 38° C.

Embodiment 28

The hardenable dental composition of embodiment 27 wherein upon hardening the structure in the second shape, the hardened structure has a flexural strength of at least 25 MPa.

Embodiment 29

The hardenable dental composition of any one of embodiments 1 through 24 which is flowable.

Embodiment 30

The hardenable dental composition of any one of embodiments 1 through 24 which is an orthodontic adhesive.

Embodiment 31

The hardenable dental composition of any one of embodiments 1 through 24 which is packable.

Embodiment 32

An organogelator of the general formula:

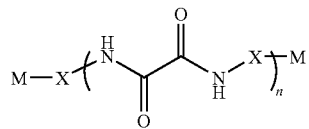

wherein each M is independently hydrogen or a polymerizable group, each X is independently an alkylene group, cycloalkylene group, arylene group, arenylene group, or a combination thereof, and n is 1 to 3.

Embodiment 33

The organogelator of embodiment 32 which is selected from the group consisting of compounds of the formulas:

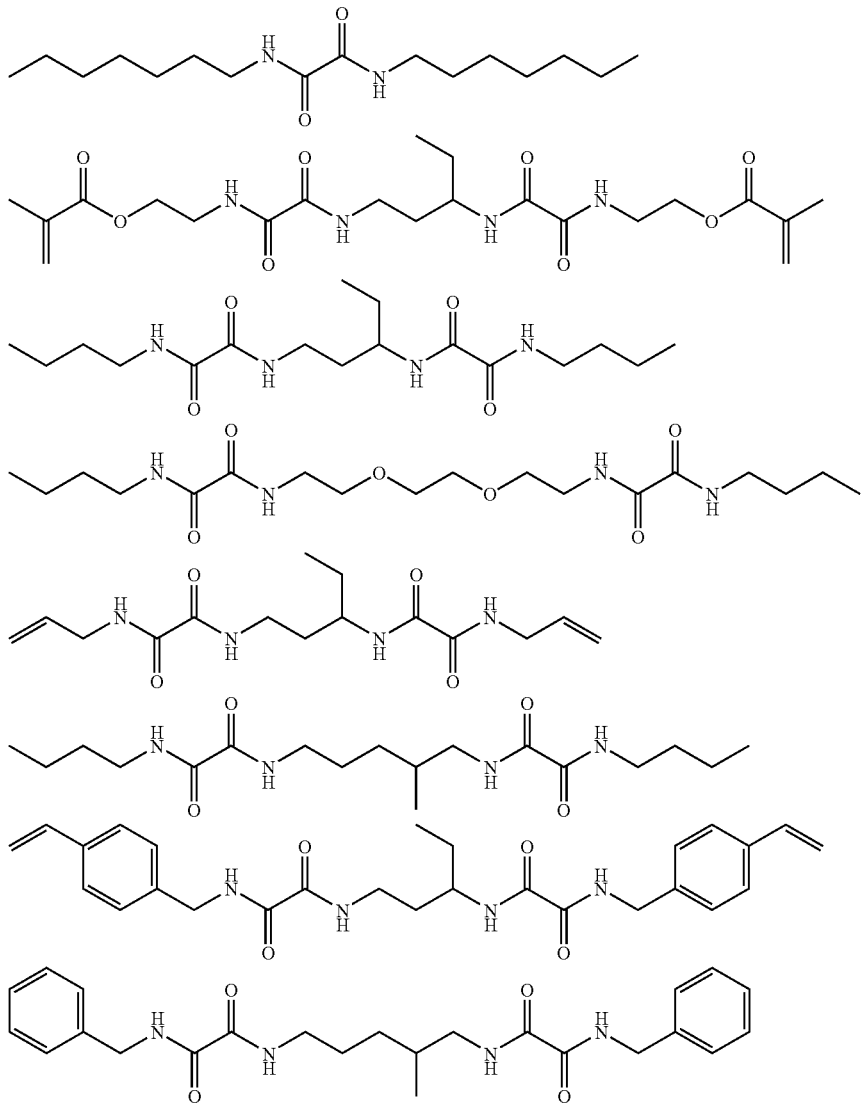

and mixtures thereof.

Embodiment 34

A dental product comprising the composition of any one of embodiments 1 through 31.

Embodiment 35

The dental product of embodiment 34 which is a preformed crown.

Embodiment 36

The dental product of embodiment 34 which is an orthodontic appliance and the composition is an orthodontic adhesive coated thereon.

Embodiment 37

A method of preparing a hardenable dental composition, the method comprising combining an organic polymerizable component, an organogelator, and a crystalline material to form a hardenable dental composition.

Embodiment 38

A method of preparing a hardenable dental composition, the method comprising combining an organic polymerizable component, an organogelator, and 60% or more filler material to form a hardenable dental composition.

Embodiment 39

A method of preparing a hardenable dental composition, the method comprising combining an organic polymerizable component, an organogelator, and filler material comprising nanoscopic particles to form a hardenable dental composition.

Embodiment 40

A method of preparing a hardenable dental composition, the method comprising combining an organic polymerizable component and a polymerizable organogelator to form a hardenable dental composition.

Embodiment 41

The method of any one of embodiments 37 through 40 wherein the hardenable dental composition is a self-supporting structure having a first shape and sufficient malleability to be formed into a second shape at a temperature of 15° C. to 38° C.

Embodiment 42

The method of any one of embodiments 37 through 40 wherein the hardenable dental composition is flowable.

Embodiment 43

The method of any one of embodiment 37 through 40 wherein the hardenable dental composition is an orthodontic adhesive.

Embodiment 44

The method of any one of embodiments 37 through 40 wherein the hardenable dental composition is packable.

Embodiment 45

A method of preparing a dental product, the method comprising: combining an organic polymerizable component, an organogelator, and a crystalline material to form a hardenable dental composition; and forming the hardenable dental composition into a dental product.

Embodiment 46

A method of preparing a dental product, the method comprising: combining an organic polymerizable component, an organogelator, and 60% or more filler material to form a hardenable dental composition; and forming the hardenable dental composition into a dental product.

Embodiment 47

A method of preparing a dental product, the method comprising: combining an organic polymerizable component, an organogelator, and filler material comprising nanoscopic particles to form a hardenable dental composition; and forming the hardenable dental composition into a dental product.

Embodiment 48

A method of preparing a dental product, the method comprising: combining an organic polymerizable component; and a polymerizable organogelator to form a hardenable dental composition; and forming the hardenable dental composition into a dental product.

Embodiment 49

The method of any one of embodiments 45 through 48 wherein the dental product is hardenable and the hardenable dental composition of the hardenable dental product is a self-supporting structure having a first shape and sufficient malleability to be formed into a second shape at a temperature of 15° C. to 38° C.

Embodiment 50

A method of preparing a dental product, the method comprising: combining an organic polymerizable component, an organogelator, and a crystalline material to form a hardenable dental composition; and applying the hardenable dental composition to a dental product.

Embodiment 51

A method of preparing a dental product, the method comprising: combining an organic polymerizable component, an organogelator, and 60% or more filler material to form a hardenable dental composition; and applying the hardenable dental composition to a dental product.

Embodiment 52

A method of preparing a dental product, the method comprising: combining an organic polymerizable component, an organogelator, and filler material comprising nanoscopic particles to form a hardenable dental composition; and applying the hardenable dental composition to a dental product.

Embodiment 53

A method of preparing a dental product, the method comprising: combining an organic polymerizable component and a polymerizable organogelator to form a hardenable dental composition; and applying the hardenable dental composition to a dental product.

Embodiment 54

The method of any one of embodiments 50 through 53 wherein the hardenable dental composition is flowable.

Embodiment 55

The method of any one of embodiments 50 through 53 wherein the hardenable dental composition is an orthodontic adhesive.

Embodiment 56

The method of any one of embodiments 50 through 53 wherein the dental product is an orthodontic appliance.

Embodiment 57

A method of using a dental product, the method comprising: providing a dental product comprising a hardenable dental composition of embodiment 26 wherein the hardenable dental composition has a self-supporting structure having a first shape and sufficient malleability to be formed into a second shape at a temperature of 15° C. to 38° C.; placing the dental product on a tooth surface in the mouth of a subject or on a model of a tooth surface; customizing the shape of the dental product in the mouth of a subject or on a model of a tooth surface; and hardening the hardenable dental composition of the dental product.

Embodiment 58

A method of using a hardenable dental composition, the method comprising: providing a hardenable dental composition of embodiments 29 or 31, wherein the hardenable dental composition is flowable or packable; placing the dental product on a tooth surface in the mouth of a subject, wherein the tooth surface is optionally coated with a dental adhesive; and hardening the hardenable dental composition.

Embodiment 59

A method of using a dental product, the method comprising: providing a hardenable dental composition of embodiment 30, wherein the hardenable dental composition is a hardenable orthodontic adhesive; placing the hardenable orthodontic adhesive on an orthodontic bracket prior to the bracket contacting a tooth surface, wherein the tooth surface is optionally coated with a dental adhesive; and hardening the hardenable orthodontic adhesive.

Embodiment 60

A method of using a dental product, the method comprising: providing a dental product comprising an orthodontic bracket having coated thereon a hardenable dental composition of embodiment 30, wherein the hardenable dental composition is a hardenable orthodontic adhesive; placing the bracket on a tooth surface, wherein the tooth surface is optionally coated with a dental adhesive; and hardening the hardenable orthodontic adhesive.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

Unless otherwise noted, all solvents and reagents were or can be obtained from Sigma-Aldrich Corp., St. Louis, Mo.

As used herein,

"IEM" refers to 2-isocyanatoethyl methacrylate;

"BHT" refers to 2,6-di-tert-butyl-4-methylphenol;

"BisGMA" refers to 2,2-bis[4-(2-hydroxy-3-methacryloyloxypropoxy)phenyl]propane;

"SR541" refers to an ethoxylated bisphenol A dimethacrylate, available under the trade designation SR541 from Sartomer Co., Exton, Pa.;

"UDMA" refers to diurethane dimethacrylate, available under the trade designation "ROHAMERE 6661-0" from Rohm America LLC, Piscataway, N.J.;

"CPQ" refers to camphorquinone;

"EDMAB" refers to ethyl 4-(N,N-dimethylamino)benzoate;

"DPIHFP" refers to diphenyl iodonium hexafluorophosphate;

"TEGDMA" refers to triethyleneglycol dimethacrylate;

"MILLITHIX" refers to an organogelator available under the trade designation "MILLITHIX 925S" from Milliken Chemical, Spartanburg, S.C.;

"M5" refers to a fumed silica available under the trade designation CAB-O-SIL M-5 from Cabot Corp., Boston, Mass.;

"TONE-IEM" refers to the reaction product of TONE 0230 (a polycaprolactone polyol available from The Dow Chemical Co., Midland, Mich.) and two equivalents of 2-isocyanatoethyl methacrylate, prepared essentially as described in U.S. Pat. No. 6,506,816;

"CAPA2200A-IEM" refers to the reaction product of CAPA2200A (a polycaprolactone polyol available from Solvay Chemical Company, Warrington, UK) and two equivalents of 2-isocyanatoethyl methacrylate, prepared essentially as described in U.S. Pat. No. 6,506,816;

"PROCRYLATE" refers to 2,2-bis-4-(3-hydroxy-propoxy-phenyl)propane dimethacrylate, CAS Number 27689-12-9, also known as PROCRYLAT, which is prepared as described in WO 2006/020760.

"TINUVIN" refers to a polymerizable UV stabilizer available under the trade designation TINUVIN R 796 from Ciba Specialty Chemicals, Tarrytown, N.Y.;

"FILLER A" refers to a silane-treated nano-sized silica having a nominal particle size of approximately 20 nanometers, prepared essentially as described for FILLER F in U.S. Patent Publication No. 2005/0252413;

"FILLER B" refers to silane-treated zirconia/silica filler prepared essentially as described in U.S. Pat. No. 6,030,606;

"FILLER C" refers to silane-treated zirconia/silica nanocluster filler prepared essentially as described in U.S. Pat. No. 6,730,156;

Glucosamine-6-Phosphate was obtained from Sigma-Aldrich Corp., St. Louis, Mo.;

D-Glucamine was obtained from TCI America, Portland, Oreg.;

N-Methyl-D-glucamine was obtained from MP Biomedicals, Solon, Ohio;

N-Methyl-N-decanoyl-D-glucamide was obtained from EMD Chemicals, Inc., San Diego, Calif.

Gelation Test

A sample of an organogelator and a resin mixture were placed in a screw cap vial to provide a mixture that was approximately 3 weight percent organogelator. Unless otherwise indicated, 30 milligrams (mg) of organogelator and 1.0 gram (g) of a mixture of 70 weight percent BisGMA and 30 weight percent TEGDMA were used. The mixture was heated until the organogelator had dissolved, and was then allowed to cool to room temperature. After 4 hours, the vial was inverted. If there was no visible flow of the liquid, it was determined that a gel had formed using the approximately 3 weight percent organogelator. If no flow was observed, a similar test was conducted using 10 mg of organogelator instead of 30 mg, to provide a mixture that was approximately 1 weight percent organogelator. If there was no visible flow of the liquid in this case, it was determined that a gel had formed using the approximately 1 weight percent organogelator.

Pre-Cure Hardness Test

Samples (approximately 3 g each) of the dental compositions were pressed to a thickness of approximately 2 millimeters, using a hydraulic press (available from Carver Inc., Wabash, Ind.) at approximately 60° C. Each pressed sample was then stored at room temperature for 7 days, after which time the pre-cure hardness was measured at 25° C. and at 37° C. using a Model TA.Xt2i texture analyzer (manufactured by Texture Technologies Corp., Scarsdale, N.Y.). The texture analyzer was fitted with a cylindrical probe having a diameter of 2 millimeters. Each sample was allowed to thermally equilibrate at 25° C. for at least 20 minutes before each analysis was carried out. The flat end of the probe was pressed into each dental composition at a rate of 1 millimeter per second to a depth of 1 millimeter.

Post-Cure Diametral Tensile Strength Test

Diametral Tensile Strength was measured according to ANSI/ADA specification No. 27 (1993). A composition sample was heated to 85° C., packed into a glass tube having an inside diameter of 4 millimeters, and then the packed tube was then capped with silicone rubber plugs. The composition was then compressed axially at approximately 0.28 MPa (approximately 40.62 pounds per square inch) for 5 minutes. The sample was then light cured for 90 seconds by exposure to two oppositely disposed VISILUX Model 2500 blue light guns (manufactured by 3M ESPE Dental Products, St. Paul, Minn.) and then irradiated for 180 seconds in a DENTA-COLOR XS light box (manufactured by Heraeus Kulzer, Hanau, Germany). The cured sample was then cut crosswise using a diamond saw to afford discs each having a length of 2.2 millimeters. The plugs were stored in distilled water at 37° C. for 24 hours prior to testing. Measurements were carried out on a Model 4505 Instron tester (manufactured by Instron Corp., Norwood, Mass.) with a 10-kilonewton (kN) load cell and at a crosshead speed of one meter per minute. Five discs of each cured composite were prepared and tested. The five measurements were averaged for the data reported in the Examples.

Preparative Example 1

Preparation of Polymerizable Composition

A bisGMA mixture was prepared by combining 100 parts by weight of bisGMA, 0.18 parts by weight CPQ, 0.52 parts by weight DPIHFP, 1.03 parts by weight EDMAB, 0.16 parts by weight BHT, and 1.55 parts by weight TINUVIN, heating the mixture to approximately 60° C., and stirring the warmed mixture with a mechanical stirrer for approximately four hours.

Preparative Example 2

Preparation of Polymerizable Composition

A bisGMA mixture was prepared by combining 13.33 parts by weight of bisGMA, 13.33 parts by weight TEGDMA, 33.6 parts by weight UDMA, 33.6 parts by weight SR541, 0.2 part by weight CPQ, 0.5 part by weight DPIHFP, 1.0 part by weight EDMAB, 0.1 part by weight BHT, and 1.5 parts by weight TINUVIN, heating the mixture to approximately 60° C., and stirring the warmed mixture with a mechanical stirrer for approximately four hours.

Preparative Example 3

Preparation of Polymerizable Composition

A TONE-IEM mixture was prepared by combining TONE-IEM (200.0 g), CPQ (0.351 g), DPIHFP (1.035 g), EDMAB (2.068 g), BHT (0.311 g), and TINUVIN (3.10 g), heating the mixture to approximately 60° C., and stirring the warmed mixture with a mechanical stirrer for approximately four hours.

Preparative Example 4

Preparation of Organogelator Precursor

A mixture of diethyl oxalate (128.72 g), ethanol (180 mL), and 1,3-diaminopentane (20.00 g) was stirred at 60° C. for 1 hour. The solvent was removed under reduced pressure to afford an oil. Excess diethyl oxalate was removed by vacuum distillation (60-70° C.; approximately 27 Pa (0.2 mmHg)) to afford 50.52 g of the product as an oil.

Preparative Example 5

Preparation of Organogelator Precursor

A mixture of diethyl oxalate (29.10 g), ethanol (40 mL), and 2,2'-(ethylenedioxy)diethylamine (7.26 g) was heated at 60° C. for 1 hour. The solvent was removed under reduced pressure to afford an oil. Excess diethyl oxalate was removed by vacuum distillation (60-70° C.; approximately 27 Pa (0.2 mmHg)) to afford 14.79 g of the product as an oil.

Preparative Example 6

Preparation of Organogelator Precursor

A mixture of diethyl oxalate (29.10 g), ethanol (40 mL), and 1,5-diamino-2-methylpentane (5.00 g) was heated at 70° C. for 2 hours. The solvent was removed under reduced pressure to afford an oil. Excess diethyl oxalate was removed by vacuum distillation (60-70° C.; approximately 27 Pa (0.2 mmHg)) to afford 11.75 g of the product as a yellow oil.

Preparative Example 7

Preparation of Polymerizable Composition

The reaction product of two equivalents of 2-hydroxyethyl methacrylate, one equivalent of pentaerythritol trimethacrylate and one equivalent of hexamethylene diisocyanate (prepared essentially as described in U.S. Pat. No. 4,648,843) (45 parts by weight) was combined with bisGMA (25 parts by weight), TEGDMA (30 parts by weight), CPQ (0.18 parts by weight), DPIHFP (0.52 parts by weight), EDMAB (1.03 parts by weight), BHT (0.16 parts by weight) and TIVUVIN (1.55 parts by weight), and this mixture was heated to approximately 50° C. and was stirred for approximately 2 hours.

Preparative Example 8

Preparation of Organogelator Precursor

Ethanolamine (6.67 g) was added dropwise to a stirring solution of the product of Preparative Example 4 (15.20 g) in ethanol (100 mL). The solution was stirred and heated to 50° C. for 2 hours. After the mixture was allowed to cool to room temperature, the precipitated solid was filtered and was washed three times with 20 milliliter portions of ethanol. The white solid was then dried under vacuum to afford 13.53 g of product.

Example 1

Preparation of Organogelator of Formula XLVIII

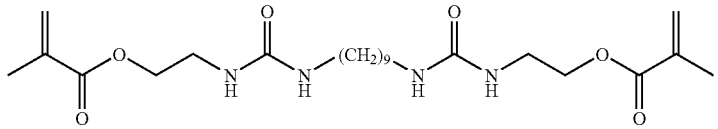

A stirring mixture of 1,9-diaminononane (2.53 g) and ethyl acetate (50 g) was heated to 70° C. 2-Isocyanatoethyl methacrylate (IEM, 5.00 g, 32) was added dropwise to the stirring mixture, and then the mixture was stirred for one hour at 70° C. The mixture was then allowed to cool to room temperature, and was then filtered. The filtered solid was dried under vacuum to give 7.24 g of the product as a white solid. This compound formed a gel according to the gelation test at approximately one weight percent organogelator.

Example 2

Preparation of Organogelator of Formula XLIX

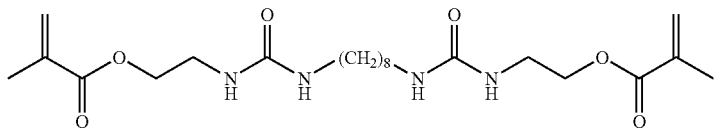

A stirring mixture of 1,8-diaminooctane (2.31 g) ethyl acetate (50 g) was heated to 70° C. 2-Isocyanatoethyl methacrylate (IEM, 5.00 g) was added dropwise to the stirring mixture, then the mixture was stirred for one hour at 70° C. The mixture was allowed to cool to room temperature, and was then filtered. The filtered solid was dried under vacuum to give 6.69 g of the product as a white solid. This compound formed a gel according to the gelation test at approximately one weight percent organogelator.

Example 3

Preparation of a Mixture of Organogelators

A mixture of organogelators comprising methacrylate groups, butyl groups, or both, was prepared as follows. To a stirring mixture of 1,12-diaminododecane (10.00 g) and toluene (100 g) at 70° C. there was added dropwise first 2-isocyanatoethyl methacrylate (9.29 g), and then butyl isocyanate (3.95 g). The mixture was then allowed to cool to room temperature. The solid that precipitated was collected by filtration and was dried under vacuum to give 21.88 g of the product as a white solid. This compound formed a gel according to the gelation test at approximately one weight percent organogelator.

Example 4

Preparation of Organogelator of Formula LX

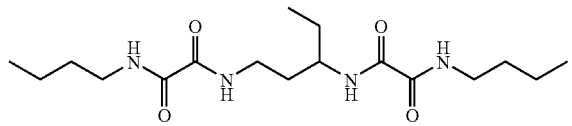 [SMILES: CCCCNC(=O)C(=O)NCCC(CC)NC(=O)C(=O)NCCCC]

n-Butylamine (6.05 g) was added dropwise to a stirring solution of the product of Preparative Example 4 (10.00 g) in ethanol (60 mL). After approximately 5 minutes, the mixture had thickened into a gel. The gel was dissolved in hot isopropanol (350 mL), and then water (350 mL) was added slowly to the mixture, which resulted in the precipitation of a solid. The solid was isolated by filtration and was then dried under vacuum to afford 9.29 g of product. This compound formed a gel according to the gelation test at approximately three weight percent organogelator.

Example 5

Preparation of Organogelator of Formula LXII

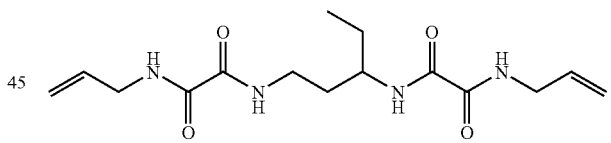

Allylamine (6.60 g) was added dropwise to a stirring solution of the product of Preparative Example 4 (13.10 g) in ethanol (90 mL). After approximately 5 minutes, the mixture was stirred and heated to approximately 50° C. for 1 hour. Water (300 mL) was added to the mixture, which was stirred and heated to approximately 80° C. for 1 hour. The precipitated solid was isolated by filtration and was then and dried under vacuum to afford 12.21 g of product. This compound formed a gel according to the gelation test at approximately one weight percent organogelator.

Example 6

Preparation of Organogelator of Formula LIX

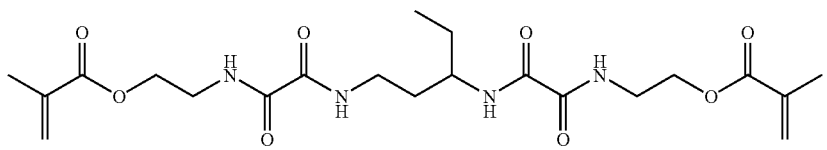 [SMILES: C=C(C)C(=O)OCCNC(=O)C(=O)NCCC(CC)NC(=O)C(=O)NCCOC(=O)C(=C)C]

A stirring mixture of the product of Preparative Example 8 (7.00 g), methacrylic anhydride (7.14 g), 4-dimethylamino pyridine (2.58 g), and tetrahydrofuran (100 mL) was heated to 65° C. for 2 hours. The mixture was then concentrated to approximately 50 mL volume under reduced pressure. After the mixture was allowed to cool to room temperature, it had thickened into a gel. The gel was dissolved in hot ethanol (100 mL), and then water (400 mL) was added. A solid precipitated from the mixture. The solid was isolated by filtration and was dried under vacuum to afford 6.25 g of product. This compound formed a gel according to the gelation test at approximately three weight percent organogelator.

Example 7

Preparation of Organogelator of Formula LVIII

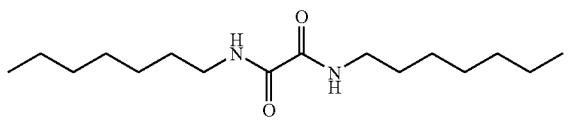 [SMILES: CCCCCCCNC(=O)C(=O)NCCCCCCC]

To a stirring mixture of diethyl oxalate (1.00 g) and ethanol (5 g) there was added n-heptylamine (1.56 g). The mixture was stirred and heated at 50° C. for 1 hour, after which time the precipitated solid was isolated by filtration. The solid was then dried under vacuum to afford the product. This compound formed a gel according to the gelation test at approximately three weight percent organogelator.

Example 8

Preparation of Organogelator of Formula LXI

Butylamine (0.53 g) was added to a stirring solution of the product of Preparative Example 5 (1.00 g) in ethanol (5 g). This mixture was stirred and heated to 60° C. for approximately 1 hour. The precipitated solid was isolated by filtration and was then washed with ethanol. The solid was dried under vacuum to afford 1.04 g of product. This compound formed a gel according to the gelation test at approximately one weight percent organogelator.

Example 9

Preparation of Organogelator of Formula LXIII

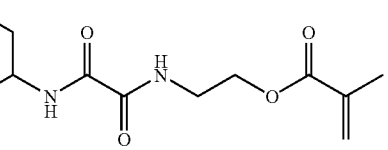

Butylamine (0.49 g, 6.6 mmol) was added to a stirring solution of the product of Preparative Example 6 (1.00 g) in ethanol (5 mL). The mixture was stirred and heated to 60° C. for approximately 1 hour. The precipitated solid was isolated by filtration and was then washed with ethanol. The solid was dried under vacuum to afford 1.03 g of product. This compound formed a gel according to the gelation test at approximately three weight percent organogelator.

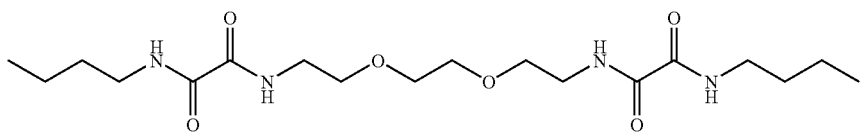 [SMILES: CCCCNC(=O)C(=O)NCCOCCOCCNC(=O)C(=O)NCCCC]

Example 10

Preparation of Organogelator of Formula LXIV

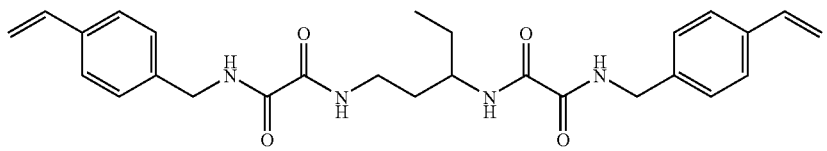 [SMILES: C=Cc1ccc(CNC(=O)C(=O)NCCC(CC)NC(=O)C(=O)NCc2ccc(C=C)cc2)cc1]

4-Vinylbenzyl amine (4.41 g, prepared according to the method described by V. Bertini et al. in *Tetrahedron*, 60, 11407 (2004)) was added dropwise to a stirring solution of the product of Preparative Example 6 (5.00 g) in ethanol (40 mL). After the mixture was stirred for 5 minutes at room temperature, it was stirred and heated to 50° C. for 1 hour and it thickened into a gel. The gel was mixed with hot isopropanol (250 mL), filtered, and dried under vacuum to afford 4.40 g of product. This compound formed a gel according to the gelation test at approximately one weight percent organogelator.

Example 11

Preparation of a Hardenable Dental Composition with Organogelator

The polymerizable composition of Preparative Example 1, in the amount shown in Table 1, was combined with MILLITHIX (in an amount shown in Table 1) and this mixture was heated to approximately 85° C. for approximately 60 minutes and was then mixed two times for one minute each using a Model DAC 150 FVZ SpeedMixer (manufactured by FlackTek, Inc., Landrum, S.C.) at 3000 rpm. To this mixture there were then added M5 and FILLER B in amounts shown in Table 1. The resultant mixture was then heated at approximately 85° C. for approximately 15 minutes and was then mixed two times for one minute each using the SpeedMixer at 3000 rpm to give a hardenable dental composition. The composition was allowed to cool to room temperature and then the pre-cure mechanical properties of the composition were evaluated as described above. At 25° C. the hardness was determined to be 3060 grams.

Comparative Examples 1-2 and Example 12

Preparation of Dental Compositions

The compositions of Comparative Examples 1-2 and Example 12 were prepared using the method essentially as described in Example 1, using the amounts of components shown in Table 1. Comparative Example 1 was prepared using FILLER B and the polymerizable composition of Preparative Example 1. Comparative Example 2 was prepared using FILLER B, M5, and the polymerizable composition of Preparative Example 1. Example 12 was prepared using MILLITHIX, FILLER B, and the polymerizable composition of Preparative Example 1. Each composition was allowed to cool to room temperature and then the pre-cure mechanical properties of a sample of each composition were evaluated as described above. At 25° C. the hardness was determined to be 244 grams (Comparative Example 1), 949 grams (Comparative Example 2), and 334 grams (Example 12). The hardness of Example 12 is not suitable for certain applications, such as crowns, but would be suitable for other applications, such as packable materials, which do not need to be as hard as crowns.

TABLE 1

Compositions of Examples 11-12 and Comparative Examples 1-2

| Example | Preparative Ex. 1 | MILLITHIX organogelator | M5 filler | FILLER B |
|---|---|---|---|---|
| 11 | 4.03 g | 0.2 g | 0.41 g | 10.49 g |
| Comparative 1 | 4.03 g | 0 g | 0 g | 10.49 g |
| Comparative 2 | 4.03 g | 0 g | 0.41 g | 10.49 g |
| 12 | 2.96 g | 0.14 g | 0 g | 7.7 g |

Example 13

Preparation of a Hardenable Dental Composition with Organogelator

The polymerizable composition of Preparative Example 2, in the amount shown in Table 2, was combined with MILLITHIX, in the amount shown in Table 2, and this mixture was heated to approximately 85° C. for approximately 60 minutes and was then mixed two times for one minute each using a Model DAC 150 FVZ SpeedMixer (manufactured by FlackTek, Inc., Landrum, S.C.) at 3000 rpm. To this mixture there were then added M5 and FILLER B in amounts shown in Table 2. The resultant mixture was then heated at approximately 85° C. for approximately 15 minutes and was then mixed two times for one minute each using the SpeedMixer at 3000 rpm to give a hardenable dental composition. The composition was allowed to cool to room temperature and then the pre-cure mechanical properties of the composition were evaluated as described above. At 25° C. the hardness was determined to be 3058 grams. The post-cure diametrical tensile strength was measured as described above and was determined to be 92.5 MPa (13,416 pounds per square inch).

Comparative Examples 4-5 and Example 14

Preparation of Dental Compositions

The compositions of Comparative Examples 4-5 and Example 14 were prepared using the method essentially as described in Example 13, using the amounts of components shown in Table 2. Comparative Example 4 was prepared using FILLER B and the polymerizable composition of Preparative Example 2. Example 14 was prepared using FILLER B, MILLITHIX, and the polymerizable composition of Preparative Example 2. Comparative Example 5 was prepared using M5, FILLER B, and the polymerizable composition of Preparative Example 2. Each composition was allowed to cool to room temperature, and then the pre-cure mechanical properties of a sample of each composition were evaluated as described above. At 25° C. the hardness was determined to be 200 grams (Comparative Example 4), 900 grams (Example 14), and 1053 grams (Comparative Example 5). The post-cure diametrical tensile strength of each composition was measured as described above and was determined to be, for Comparative Example 4, 96.7 MPa (14,025 pounds per square inch), for Example 14, 95.7 MPa (13,880 pounds per square inch), and, for Comparative Example 5, 88.7 MPa (12,865 pounds per square inch). The hardness of Example 14 is not suitable for certain applications, such as crowns, but would be suitable for other applications, such as packable materials, which do not need to be as hard as crowns.

TABLE 2

Compositions of Examples 13-14 and Comparative Examples 4-5

| Example | Preparative Ex. 2 | MILLITHIX organogelator | M5 Filler | FILLER B |
|---|---|---|---|---|
| 13 | 2.56 g | 0.14 g | 0.37 g | 11.93 g |
| Comparative 4 | 2.70 g | 0 g | 0 g | 12.30 g |
| 14 | 2.56 g | 0.14 g | 0 g | 12.31 g |
| Comparative 5 | 2.70 g | 0 g | 0.37 g | 11.93 g |

Example 15

Preparation of a Hardenable Dental Composition with TONE-IEM and Organogelator

The polymerizable composition of Preparative Example 2 was combined with the polymerizable composition of Preparative Example 3 and with MILLITHIX, in the amounts shown in Table 3, and this mixture was heated to approximately 85° C. for approximately 60 minutes and was then mixed two times for one minute each using a Model DAC 150 FVZ SpeedMixer (manufactured by FlackTek, Inc., Landrum, S.C.) at 3000 rpm. To this mixture there were then added M5 and FILLER B in amounts shown in Table 3. The resultant mixture was then heated at approximately 85° C. for approximately 15 minutes and was then mixed two times for one minute each using the SpeedMixer at 3000 rpm to give a hardenable dental composition. The composition was allowed to cool to room temperature and then the pre-cure mechanical properties of the composition were evaluated as described above. At 25° C. the hardness was determined to be 1554 grams. The post-cure diametrical tensile strength was measured as described above and was determined to be 86.5 MPa (12,546 pounds per square inch).

Example 16

Preparation of a Hardenable Dental Composition with TONE-IEM and Organogelator

The polymerizable composition of Preparative Example 2 was combined with the polymerizable composition of Preparative Example 3 and with MILLITHIX, in the amounts shown in Table 3, and this mixture was heated to approximately 85° C. for approximately 60 minutes and was then mixed two times for one minute each using a Model DAC 150 FVZ SpeedMixer (manufactured by FlackTek, Inc., Landrum, S.C.) at 3000 rpm. To this mixture there was then added FILLER B in the amount shown in Table 3. The resultant mixture was then heated at approximately 85° C. for approximately 15 minutes and was then mixed two times for one minute each using the SpeedMixer at 3000 rpm to give a hardenable dental composition. The composition was allowed to cool to room temperature and then the pre-cure mechanical properties of a sample of the composition were evaluated as described above. At 25° C. the hardness was determined to be 3804 grams. The post-cure diametrical tensile strength was measured as described above and was determined to be 83.5 MPa (12,111 pounds per square inch).

Comparative Example 6

Preparation of Dental Composition

The composition of Comparative Example 6 was prepared using the method essentially as described in Example 16. This composition was prepared using the polymerizable composition of Preparative Example 2, the polymerizable composition of Preparative Example 3, and FILLER B in the amounts given in Table 3. The composition was allowed to cool to room temperature and then the pre-cure mechanical properties of a sample of the composition were evaluated as described above. At 25° C. the hardness was determined to be 2525 grams. The post-cure diametrical tensile strength was measured as described above and was determined to be 73.9 MPa (10,718 pounds per square inch).

TABLE 3

Compositions of Examples 15-16 and Comparative Example 6

| Example | Preparative Ex. 2 | Preparative Ex. 3 | MILLITHIX Organogelator | M5 filler | FILLER B |
|---|---|---|---|---|---|
| 15 | 2.23 g | 0.41 | 0.07 g | 0.19 g | 12.12 g |
| 16 | 1.76 g | 0.81 | 0.14 g | 0 g | 12.30 g |
| Comparative 6 | 1.88 g | 0.82 | 0 g | 0 g | 12.30 g |

Examples 17-20 and Comparative Examples 7-9

Preparation of Crowns

Crowns having the shape of an upper bicuspid were molded with approximately 0.5 g of each dental composition of Examples 13-16 and of Comparative Examples 4-6 using poly(ethylene-co-vinyl acetate) film (0.076 mm (0.003 inch) thick; 19 weight percent vinyl acetate) and a four-part steel mold in the method essentially as described in U.S. Patent Publication No. 2005/0040551. Each molded crown was removed from the mold and was allowed to stand for at least 24 hours at room temperature. Each crown was then evaluated after removing the crown from the film and then placing the crown on a prepared plastic upper bicuspid tooth in a typodont. The criteria for evaluation included the ease of removal of the crown from the film, the retention of molded crown shape as the crown was removed from the film, the conformation of the crown with the prepared tooth in the typodont, and the formation of contact between the crown and teeth adjacent the crown in the typodont. The results of the evaluation of each crown are given in Table 4. In Table 4, "soft" means that that crown was considered to be too soft to be further shaped with instruments or that it did not retain its shape as it was removed from the film, "brittle" means that cracks formed in the crown as it was further shaped with instruments, and "malleable" means that the crown had sufficient hardness to be fitted in the typodont and be further shaped with instruments. Although the composition of Example 18 is not suitable for crowns, it is believed that it would be suitable for other applications, such as packable materials.

TABLE 4

Examples 17-20 and Comparative Examples 8-10

| Example | Results |
| --- | --- |
| 17 (based on Example 13) | Malleable |
| 19 (based on Example 15) | Malleable |
| 20 (based on Example 16) | Malleable |
| Comparative 7 (based on Comparative 4) | Soft |
| 18 (based on Example 14) | Soft |
| Comparative 8 (based on Comparative 5) | Soft |
| Comparative 9 (based on Comparative 6) | Brittle |

Example 21

Preparation of Dental Composition

The polymerizable composition of Preparative Example 2 (98 parts by weight) was combined with the organogelator of Example 5 (2 parts by weight) and this mixture was stirred for approximately one minute using a Model DAC 150 FVZ SpeedMixer at 3000 rpm. This resin (23 parts by weight) was combined with FILLER C (69.3 parts by weight) and FILLER A (7.7 parts by weight) and the mixture was heated to 85° C. for approximately 20 minutes and was then stirred three times for approximately one minute each using the SpeedMixer at 3000 rpm to afford a hardenable dental composition including an organogelator. The composition was allowed to cool to room temperature and then the pre-cure mechanical properties of a sample of the composition were evaluated as described above. At 25° C. the hardness was determined to be 408 grams. The post-cure diametrical tensile strength was measured as described above and was determined to be 60 MPa (8,702 pounds per square inch).

Example 22

Preparation of Dental Composition

A hardenable dental composition was prepared essentially as described in Example 19 except that the organogelator of Example 6 was used in place of the organogelator of Example 5. The composition was allowed to cool to room temperature and then the pre-cure mechanical properties of a sample of the composition were evaluated as described above. At 25° C. the hardness was determined to be 431 grams. The post-cure diametrical tensile strength was measured as described above and was determined to be 67 MPa (9718 pounds per square inch).

Example 23

Preparation of Dental Composition

A hardenable dental composition was prepared essentially as described in Example 19 except that the organogelator of Example 7 was used in place of the organogelator of Example 5. The composition was allowed to cool to room temperature and then the pre-cure mechanical properties of a sample of the composition were evaluated as described above. At 25° C. the hardness was determined to be 492 grams. The post-cure diametrical tensile strength was measured as described above and was determined to be 67 MPa (9718 pounds per square inch).

Comparative Example 10

The polymerizable composition of Preparative Example 2 (23 parts by weight) was combined with FILLER C (69.3 parts by weight) and FILLER A (7.7 parts by weight) and the mixture was heated to 85° C. for approximately 20 minutes and was then stirred three times for approximately one minute each using a Model DAC 150 FVZ SpeedMixer at 3000 rpm to afford a hardenable dental composition including an organogelator. The composition was allowed to cool to room temperature and then the pre-cure mechanical properties of a sample of the composition were evaluated as described above. At 25° C. the hardness was determined to be 308 grams. The post-cure diametrical tensile strength was measured as described above and was determined to be 68 MPa (9863 pounds per square inch).

Example 24

Preparation of Organogelator XLVI

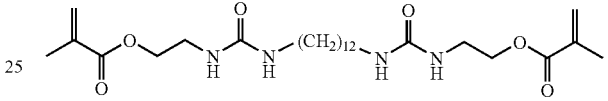

To a mechanically stirring mixture of 1,12-diaminododecane (64.57 g) and ethyl acetate (1.0 liter) at 70° C. there was added dropwise 2-isocyanatoethyl methacrylate (100.0 g) over approximately one hour. The mixture was then stirred for approximately two hours at 70° C., after which time the mixture was allowed to cool to room temperature. The white solid that had formed was isolated by filtration. The filtered white solid was dried at room temperature to afford 159.8 g of the product.

Example 25

Preparation of Organogelator XLVII

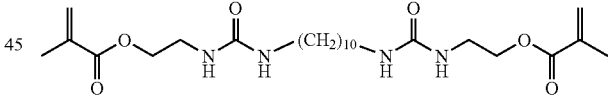

To a mechanically stirring mixture of 1,10-diaminodecane (55.48 g) and ethyl acetate (1 liter) at 70° C. there was added dropwise 2-isocyanatoethyl methacrylate (100.00 g) over approximately one hour. The mixture was then stirred for approximately one hour at 70° C., after which time the mixture was allowed to cool to room temperature. The white solid that had formed was isolated by filtration. The filtered solid was dissolved in hot methanol (800 mL), and the resultant hot solution was then filtered. The filtrate was allowed to cool to room temperature, and then the precipitated solid was filtered. The solid was dried under vacuum to give 130.0 g of the product as a white solid.

Example 26

Preparation of Dental Composition

The polymerizable composition of Preparative Example 2 (2.24 g) was combined with the organogelator of Example 24

(0.06 g) and this mixture was heated to approximately 85° C. for approximately 20 minutes and was then mixed using a Model DAC 150 FVZ SpeedMixer at 3000 rpm for one minute. To this mixture there was added FILLER C (6.93 g) and FILLER A (0.77 g). The resultant composition was then mixed using the SpeedMixer three times for one minute each to afford a hardenable dental composition including a polymerizable organogelator. The composition was allowed to cool to room temperature and then the pre-cure mechanical properties of a sample of the composition were evaluated as described above. At 25° C. the hardness was determined to be 757 grams. The post-cure diametrical tensile strength was measured as described above and was determined to be 68.1 MPa (9877 pounds per square inch).

Example 27

Preparation of Dental Composition

The composition of Example 27 was prepared essentially as described in Example 26, except that 2.18 g of the polymerizable composition of Preparative Example 2 and 0.12 g of the organogelator of Example 24 were used. At 25° C. the hardness was determined to be 1071 grams. The post-cure diametrical tensile strength was measured as described above and was determined to be 75.1 MPa (10,892 pounds per square inch).

Example 28

Preparation of Dental Composition

The composition of Example 28 was prepared essentially as described in Example 26, except that 0.06 g of the organogelator of Example 25 was used in place of the product of Example 22. At 25° C. the hardness was determined to be 755 grams. The post-cure diametrical tensile strength was measured as described above and was determined to be 71.5 MPa (10,370 pounds per square inch).

Comparative Example 11

The polymerizable composition of Preparative Example 2 (2.24 g) was heated to approximately 85° C. and was then combined with FILLER C (6.93 g) and FILLER A (0.77 g). The resultant composition was then mixed using a Model DAC 150 FVZ SpeedMixer three times for one minute each to afford a hardenable dental composition. The composition was allowed to cool to room temperature and then the pre-cure mechanical properties of a sample of the composition were evaluated as described above. At 25° C. the hardness was determined to be 448 grams. The post-cure diametrical tensile strength was measured as described above and was determined to be 77.4 MPa (11,226 pounds per square inch).

Example 29

Preparation of Dental Composition

The polymerizable composition of Preparative Example 7 (2.16 g) was combined with the organogelator of Example 24 (0.14 g) and this mixture was heated to approximately 85° C. for approximately 20 minutes and was then mixed using a Model DAC 150 FVZ SpeedMixer at 3000 rpm for one minute. To this mixture there was added FILLER C (6.93 g) and FILLER A (0.77 g). The resultant composition was then mixed using the SpeedMixer two times for one minute each to afford a hardenable dental composition including a polymerizable organogelator. The post-cure diametrical tensile strength was measured as described above and was determined to be 63.2 MPa (9166 pounds per square inch).

Example 30

Preparation of Dental Composition

The product of Example 28 was prepared essentially as described in Example 29, except that 0.14 g of the organogelator of Example 25 was used in place of the organogelator of Example 24. The post-cure diametrical tensile strength was measured as described above and was determined to be 66.8 MPa (9689 pounds per square inch).

Comparative Example 12

The polymerizable composition of Preparative Example 7 (2.24 g) was heated to approximately 85° C. and was then combined with FILLER C (6.93 g) and FILLER A (0.77 g). The resultant composition was then mixed using a Model DAC 150 FVZ SpeedMixer three times for one minute each to afford a hardenable dental composition. The post-cure diametrical tensile strength was measured as described above and was determined to be 71.3 MPa (10,341 pounds per square inch).

Examples 31-32 and Comparative Examples 13-14

Crowns were molded using each of the compositions of Examples 29 and 30 and Comparative Example 11 and 12 by the procedure essentially as described in Examples 17-20 and Comparative Examples 7-9. The criteria for evaluation included the ease of removal of the crown from the film, the retention of molded crown shape as the crown was removed from the film, the conformation of the crown with the prepared tooth in the typodont, and the formation of contact between the crown and teeth adjacent the crown in the typodont. The results of the evaluation of each crown are given in Table 5. In Table 5, "soft" means that that crown was considered to be too soft to be further shaped with instruments or that it did not retain its shape as it was removed from the film, and "malleable" means that the crown had sufficient hardness to be fitted in the typodont and be further shaped with instruments.

TABLE 5

Examples 31-32 and Comparative Examples 13-14

| Example | Results |
| --- | --- |
| 31 (based on Example 29) | Malleable |
| 32 (based on Example 30) | Malleable |
| Comparative 13 (based on Comparative 11) | Soft |
| Comparative 14 (based on Comparative 12) | Soft |

Examples 33-36 and Comparative Example 15

The Gelation Test was performed as above using several different amino sugar organogelators and a resin mixture of UDMA and PROCRYLATE as follows. A sample of an amino sugar organogelator (90 mg) as listed in Table 6, 2.0 g of UDMA, and 1.0 g PROCRYLATE were placed in a screw cap vial to provide a resin mixture containing 3% organogelator. The mixture was heated to a temperature of about 70° C. until the organogelator had dissolved, and then the mixture was allowed to cool to room temperature. After 4 hours, the vial was inverted. If there was no visible flow of the liquid, it was determined that a gel had formed.

TABLE 6

Gelation Test Using an Amino Sugar Organogelator

| Example | UDMA (grams) | PROCRYLATE (grams) | Organogelator (grams) | Results |
|---|---|---|---|---|
| 33 | 2.0 g | 1.0 g | D-Glucamine | Gelled |
| Comp. 15 | 2.0 g | 1.0 g | None | Not Gelled |
| 34 | 2.0 g | 1.0 g | N-Methyl Glucamine | Gelled |
| 35 | 2.0 g | 1.0 g | N-Methyl-N-Decanoylglucamide | Gelled |
| 36 | 2.0 g | 1.0 g | Glucosamine-6-phosphate | Gelled |

Examples 37-41 and Comparative Examples 16-20

Dental composite formulations were prepared by following the general procedure described in Example 13, with specific resin, filler, and organogelator compositions described in the following Tables 7, 9, 11, and 13. The Pre-Cure Hardness Test was conducted by following the procedure described above. Data are provided in Tables 8, 10, 12, and 14.

TABLE 7

Dental Composite Formulations with Glucamine Gelator

| Ex. | UDMA (g) | PRO-CRYLATE (grams) | CAPA-2200A-IEM (g) | Filler C (grams) | Filler A (grams) | M5 (grams) | D-Glucamine (grams) |
|---|---|---|---|---|---|---|---|
| 37 | 2.1263 | 0.9113 | 0.3375 | 5.6963 | 5.6963 | 0.2325 | 0.1350 |
| Comp. 16 | 2.1263 | 0.9113 | 0.3375 | 5.6963 | 5.6963 | 0.2325 | N/A |
| 38 | 2.1263 | 0.9113 | 0.3375 | 5.6963 | 5.6963 | 0.4650 | 0.1350 |
| Comp. 17 | 2.1263 | 0.9113 | 0.3375 | 5.6963 | 5.6963 | 0.4650 | N/A |

TABLE 8

Pre-Cure Hardness Testing Data

| Ex. | 25° C. test, after 1 Day @CTH Condition | Standard Deviation | 25° C. test, after 7 Days @CTH Condition | Standard Deviation | 37° C. test, after 7 Days @CTH Condition | Standard Deviation |
|---|---|---|---|---|---|---|
| 37 | 1069 g | 62 | 1062 g | 106 | 541 g | 65 |
| Comp. 16 | 873 g | 24 | 777 g | 25 | 302 g | 75 |
| 38 | 2724 g | 202 | 2266 g | 92 | 1162 g | 49 |
| Comp. 17 | 1852 g | 354 | 1679 g | 14 | 948 g | 28 |

CTH = Constant Temperature and Humidity; i.e., 50% Relative Humidity, 23° C.

TABLE 9

Dental Composite Formulations with N-Methyl Glucamine Gelator

| Ex. | UDMA (g) | PRO-CRYLATE (g) | CAPA-2200A-IEM (g) | Filler B (g) | N-Methyl Glucamine (g) | M5 (g) |
|---|---|---|---|---|---|---|
| 39 | 1.7663 | 0.8831 | 0.6750 | 14.6756 | 0.0665 | 0.4670 |
| Comp. 18 | 1.7663 | 0.8831 | 0.6750 | 14.6756 | 0 | 0.4670 |

TABLE 10

Pre-Cure Hardness Testing Data

| Ex. | 25° C. test, after 1 Day @CTH Condition | Standard Deviation | 25° C. test, after 7 Days @CTH Condition | Standard Deviation | 37° C. test, after 7 Days @CTH Condition | Standard Deviation |
|---|---|---|---|---|---|---|
| 39 | 2779 g | 46 | 2625 g | 249 | 1938 g | 116 |
| Comp. 18 | 1366 g | 164 | 1956 g | 23 | 1147 g | 67 |

CTH = Constant Temperature and Humidity; i.e., 50% Relative Humidity, 23° C.

TABLE 11

Dental Composite Formulations with N-Methyl Glucamine Gelator

| Ex. | PROCRYLATE (g) | Filler B (g) | N-Methyl Glucamine (g) |
|---|---|---|---|
| 40 | 3.00 | 12.00 | 0.060 |
| Comp. 19 | 3.00 | 12.00 | 0 |

TABLE 12

Pre-Cure Hardness Testing Data

| Ex. | 25° C. test, after 1 Day @CTH Condition | Standard Deviation | 25° C. test, after 7 Days @CTH Condition | Standard Deviation | 37° C. test, after 7 Days @CTH Condition | Standard Deviation |
|---|---|---|---|---|---|---|
| 40 | 270 g | 9 | 333 g | 6 | 277 g | 15 |
| Comp. 19 | 151 g | 10 | 181 g | 12 | 162 g | 10 |

TABLE 13

Dental Composite Formulations with N-Methyl Glucamine Gelator

| Ex. | Bis-GMA (g) | Filler B (g) | N-Methyl Glucamine (g) |
|---|---|---|---|
| 41 | 3.00 g | 12.00 g | 0.060 g |
| Comp. 20 | 3.00 g | 12.00 g | 0 g |

TABLE 14

Pre-Cure Hardness Testing Data

| Ex. | 25° C. test, after 1 Day @CTH Condition | Standard Deviation | 25° C. test, after 7 Days @CTH Condition | Standard Deviation | 37° C. test, after 7 Days @CTH Condition | Standard Deviation |
|---|---|---|---|---|---|---|
| 41 | 1563 g | 110 | 1383 g | 37 | 796 g | 36 |
| Comp. 20 | 803 g | 29 | 667 g | 121 | 401 g | 79 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A hardenable dental composition comprising:
   (a) an organic chemically polymerizable component comprising an ethylenically unsaturated compound;
   (b) 0.01 wt-% to 10 wt-% of an oxamide compound organogelator; and
   (c) a filler material in an amount of 60% or more, wherein the filler comprises nanoscopic particles.

2. The hardenable dental composition of claim 1 wherein the hardenable dental composition further comprises a crystalline material comprising a reactive group.

3. The composition of claim 1 wherein the hardenable dental composition further comprises a crystalline material comprising polyesters, polyethers, polyolefins, polythioethers, polyarylalkylenes, polysilanes, polyamides, polyurethanes, or combinations thereof.

4. The composition of claim 3 wherein the hardenable dental composition comprises a crystalline material comprising saturated, linear, aliphatic polyester polyols containing primary hydroxyl end groups.

5. The hardenable dental composition of claim 1 wherein the nanoscopic particles form aggregated networks.

6. The hardenable dental composition of claim 1 wherein the nanoscopic particles comprise fumed silica.

7. The hardenable dental composition of claim 1 wherein the organogelator is polymerizable.

8. The hardenable dental composition of claim 1 wherein the composition is photopolymerizable.

9. The hardenable dental composition of claim 1 wherein the organogelator is of the general formula:

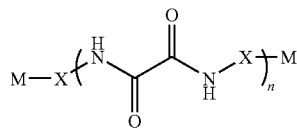

wherein each M is independently hydrogen or a polymerizable group, each X is independently an alkylene group, cycloalkylene group, arylene group, arenylene group, or combinations thereof, and n is 1 to 3.

10. The hardenable dental composition of 9 wherein the organogelator is selected from the group consisting of compounds of the formulas:

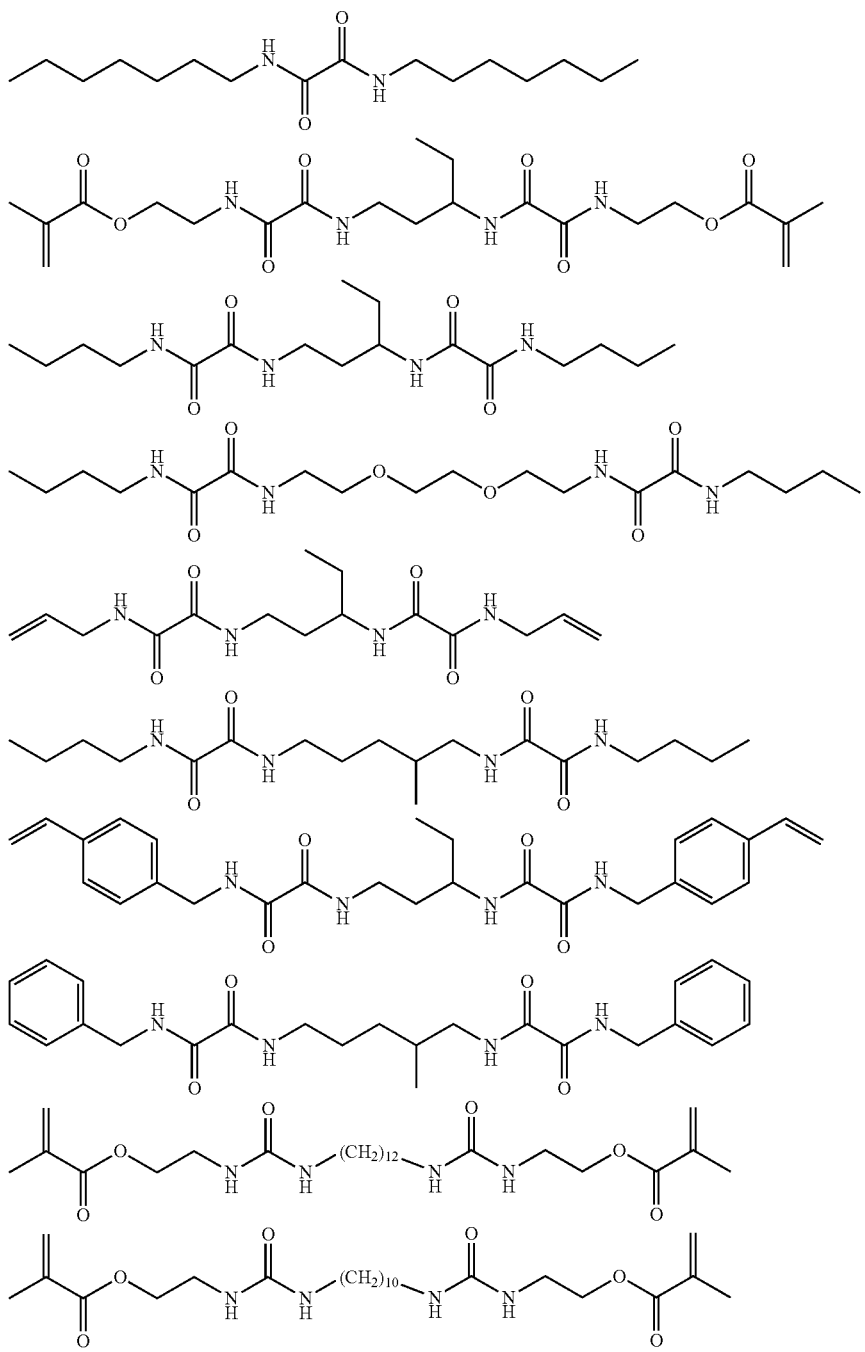

and mixtures thereof.

11. The hardenable dental composition of claim 1 which is in the form of a hardenable self-supporting structure having a first shape and sufficient malleability to be formed into a second shape at a temperature of 15° C. to 38° C.

12. The hardenable dental composition of claim 11 wherein upon hardening the structure in the second shape, the hardened structure has a flexural strength of at least 25 MPa.

13. A dental product comprising a hardenable dental composition comprising:
(a) an organic polymerizable component;
(b) 0.01 wt-% to 10 wt-% of an oxamide compound organogelator; and
(c) a filler material in an amount of 60% or more, wherein the filler comprises nanoscopic particles.

14. The dental product of claim 13 which is a preformed crown.

15. A method of using a dental product, the method comprising:
providing a dental product comprising a hardenable dental composition of claim 13 wherein the hardenable dental composition has a self-supporting structure having a first shape and sufficient malleability to be formed into a second shape at a temperature of 15° C. to 38° C.;
placing the dental product on a tooth surface in the mouth of a subject or on a model of a tooth surface;
customizing the shape of the dental product in the mouth of a subject or on a model of a tooth surface; and
hardening the hardenable dental composition of the dental product.

16. The dental product of claim 13 wherein the hardenable dental composition comprises a crystalline material comprising a reactive group.

17. The dental product of claim 13 wherein the hardenable dental composition comprises a crystalline material comprising polyesters, polyethers, polyolefins, polythioethers, polyarylalkylenes, polysilanes, polyamides, polyurethanes, or combinations thereof.

18. The dental product of claim 17 wherein the hardenable dental composition comprises a crystalline material comprising saturated, linear, aliphatic polyester polyols containing primary hydroxyl end groups.

19. The dental product of claim 13 wherein the nanoscopic particles form aggregated networks.

20. The dental product of claim 13 wherein the nanoscopic particles comprise fumed silica.

21. The dental product of claim 13 wherein the organogelator is polymerizable.

22. The dental product of claim 13 wherein the composition is photopolymerizable.

23. The dental product of claim 13 wherein the composition is chemically polymerizable.

24. The dental product of claim 23 wherein the organic polymerizable component comprises an ethylenically unsaturated compound.

25. The dental product of claim 13 wherein the organogelator is of the general formula:

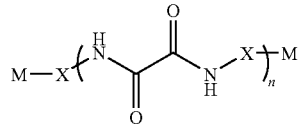

wherein each M is independently hydrogen or a polymerizable group, each X is independently an alkylene group, cycloalkylene group, arylene group, arenylene group, or combinations thereof, and n is 1 to 3.

26. The dental product of claim 25 wherein the organogelator is selected from the group consisting of compounds of the formulas:

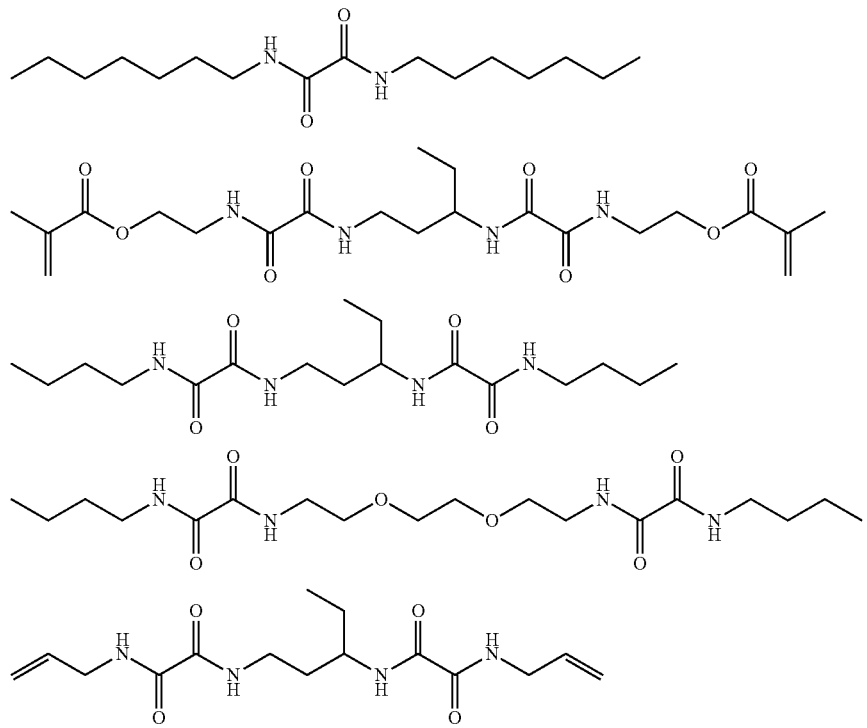

-continued

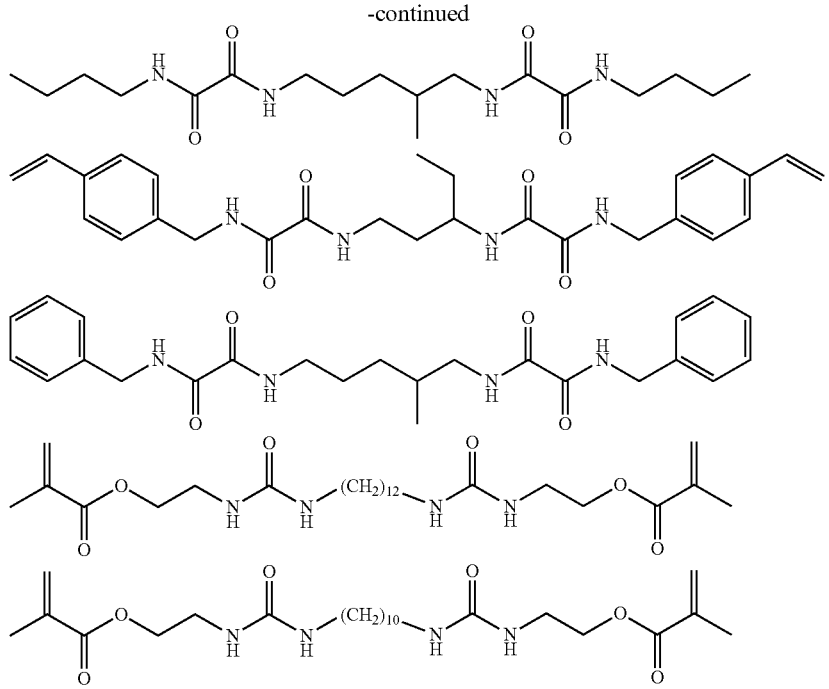

and mixtures thereof.

27. The dental product of claim 13 which is in the form of a hardenable self-supporting structure having a first shape and sufficient malleability to be formed into a second shape at a temperature of 15° C. to 38° C.

28. The dental product of claim 27 wherein upon hardening the structure in the second shape, the hardened structure has a flexural strength of at least 25 MPa.

* * * * *

UNITED STATES PATENT AND TRADEMARK OFFICE
CERTIFICATE OF CORRECTION

PATENT NO. : 8,445,558 B2
APPLICATION NO. : 12/441011
DATED : May 21, 2013
INVENTOR(S) : Naimul Karim It is certified that error appears in the above-identified patent and that said Letters Patent is hereby corrected as shown below:

Title Page
Column 2 (Other Publications), line 9, Delete "Interatction" and insert -- Interaction --, therefor.

In the Specification
Column 7
Line 62, Delete "coexistance" and insert -- coexistence --, therefor.

Column 23
Line 52, Delete "dibenzilidine" and insert -- dibenzylidene --, therefor.

Column 27
Line 7, Delete "methacylates" and insert -- methacrylates --, therefor.

Column 28
Line 32, Delete "thereof," and insert -- thereof; --, therefor.

Column 72
Line 58, Delete "that that" and insert -- that --, therefor.

Column 76
Line 41, Delete "that that" and insert -- that --, therefor.

In the Claims
Column 82
Line 7, In Claim 10, delete "of 9" and insert -- of claim 9 --, therefor.

Signed and Sealed this
Twenty-fourth Day of September, 2013

Teresa Stanek Rea
*Deputy Director of the United States Patent and Trademark Office*